United States Patent
Brentjens et al.

(10) Patent No.: US 11,103,531 B2
(45) Date of Patent: Aug. 31, 2021

(54) COMPOSITIONS AND METHODS FOR IMMUNOTHERAPY

(71) Applicant: MEMORIAL SLOAN-KETTERING CANCER CENTER, New York, NY (US)

(72) Inventors: Renier J. Brentjens, Short Hills, NJ (US); Hollie J. Jackson, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 259 days.

(21) Appl. No.: 16/148,687

(22) Filed: Oct. 1, 2018

(65) Prior Publication Data
US 2019/0083534 A1    Mar. 21, 2019

Related U.S. Application Data

(60) Division of application No. 14/835,264, filed on Aug. 25, 2015, now Pat. No. 10,124,023, which is a continuation of application No. PCT/US2014/018667, filed on Feb. 26, 2014.

(60) Provisional application No. 61/769,543, filed on Feb. 26, 2013.

(51) Int. Cl.
| | |
|---|---|
| *A61K 35/17* | (2015.01) |
| *C07K 14/725* | (2006.01) |
| *C07K 16/28* | (2006.01) |
| *A61K 35/545* | (2015.01) |
| *A61K 35/12* | (2015.01) |

(52) U.S. Cl.
CPC ............ *A61K 35/17* (2013.01); *A61K 35/12* (2013.01); *A61K 35/545* (2013.01); *C07K 14/7051* (2013.01); *C07K 16/2803* (2013.01); *C07K 2317/622* (2013.01)

(58) Field of Classification Search
CPC ............... A61K 35/17; C07K 14/7051; C12N 5/0636–0638; C12N 2510/00
See application file for complete search history.

(56) References Cited

U.S. PATENT DOCUMENTS

| | | |
|---|---|---|
| 8,389,282 B2 | 3/2013 | Sadelain et al. |
| 2010/0178276 A1 | 7/2010 | Sadelain et al. |
| 2011/0044953 A1 | 2/2011 | Allison et al. |
| 2011/0293610 A1 | 12/2011 | Ruben et al. |

FOREIGN PATENT DOCUMENTS

| | | |
|---|---|---|
| JP | 2009-532030 A | 9/2009 |
| WO | WO 1999/014353 A2 | 3/1999 |
| WO | WO 2003/106498 A2 | 12/2003 |
| WO | WO 2007/123737 A2 | 11/2007 |
| WO | WO 2008/121420 A1 | 10/2008 |
| WO | WO 2011/119979 A2 | 9/2011 |
| WO | WO 2012/079000 A1 | 6/2012 |
| WO | WO 2012/082841 A2 | 6/2012 |
| WO | WO 2012/123755 A1 | 9/2012 |
| WO | WO 2012/129514 A1 | 9/2012 |
| WO | WO 2013/019615 A2 | 2/2013 |
| WO | WO 2014/055668 A1 | 4/2014 |
| WO | WO 2014/134165 A1 | 9/2014 |

OTHER PUBLICATIONS

Sadelain et al., Cancer Disc 3:388-98 (Year: 2013).*
U.S. Appl. No. 14/835,264 (U.S. Pat. No. 10,124,023), filed Aug. 25, 2015 (Nov. 13, 2018).
U.S. Appl. No. 14/835,264, Sep. 28, 2018 Issue Fee Payment.
U.S. Appl. No. 14/835,264, Jun. 29, 2018 Notice of Allowance.
U.S. Appl. No. 14/835,264, May 22, 2018 Response to Non-Final Office Action.
U.S. Appl. No. 14/835,264, Jan. 22, 2018 Non-Final Office Action.
U.S. Appl. No. 14/835,264, Dec. 20, 2017 Response to Restriction Requirement.
U.S. Appl. No. 14/835,264, Jul. 20, 2017 Restriction Requirement.
Condomines et al., "Attenuated CTLA-4 Inhibition in CD19-Targeted T Cells Expressing a Second-Generation CD28-Based Chimeric Antigen Receptor," Molecular Therapy 20(Suppl. 1): S181, paragraph 466 (2012).
Darcy et al., "Anti-PD-1 therapy potently enhances rejection of established tumors by genetically modified T cells," International Journal of Molecular Medicine, S44, paragraph 257 (2012).
Demirtzoglou et al., "Cytolytic and Cytotoxic Activity of a Human Natural Killer Cell Line Genetically Modified to Specifically Recognize HER-2/neu Overexpressing Tumor Cells," Immunopharmacology and Immunotoxicology, 28:571-590 (2006).
Extended European Search Report dated Sep. 5, 2016 in Application No. EP14756894.
Grupp et al., "Chimeric Antigen Receptor-Modified T Cells for Acute Lymphoid Leukemia," N Engl J Med, 368:1509-1518 (2013).
Higham et al., "Activation of Tolerogenic Dendritic Cells in the Tumor Draining Lymph Nodes by CD8+ T Cells Engineered to Express CD40 Ligand," J. Immunol. 184:3394-3400 (2010).
Hudecek et al., "The B-cell tumor-associated antigen ROR1 can be targeted with T cells modified to express a ROR1-specific chimeric antigen receptor," Blood 116(22):4532-4541 (2010).
International Search Report dated Jul. 29, 2014 in International Application No. PCT/US2014/018667.

(Continued)

*Primary Examiner* — Jessica H Roark
(74) *Attorney, Agent, or Firm* — Baker Botts L.L.P.

(57) ABSTRACT

The present invention provides for methods and compositions for enhancing the immune response toward cancers and pathogens. It relates to immunoresponsive cells bearing antigen receptors, which can be chimeric antigen receptors (CARs), which express introduced ligands for immunomodulatory molecules. In particular embodiments, engineered immunoresponsive cells are antigen-directed and resist immunosuppression and/or have enhances immune-activating properties.

19 Claims, 43 Drawing Sheets

Specification includes a Sequence Listing.

(56) References Cited

OTHER PUBLICATIONS

Mihara et al, "Synergistic and persistent effect of T-cell immunotherapy with anti-CD19 or anti-CD38 chimeric receptor in conjunction with rituximab on B-cell non-Hodgkin lymphoma," British Journal of Haematology, 151:37-46 (2010).

Peggs et al., "Cancer Immunotherapy: co-stimulatory agonists and co-inhibitory antagonists," Clinical & Experimental Immunology 157:9-19 (2009).

Porter et al, "Chimeric Antigen Receptor-Modified T Cells in Chronic Lymphoid Leukemia," N Engl J Med, 365:725-733 (2011).

Singh et al., "Redirecting Specificity of T-cell Populations for CD19 Using the Sleeping Beauty System," Cancer Res., 68(8):2961-2971 (2008).

Cartellieri et al., "Chimeric Antigen Receptor-Engineered T Cells for Immunotherapy of Cancer," Journal of Biomedicine and Biotechnology 2010 (13 pages).

Curran, K. J., et al. "Constitutive Expression of CD40L by CAR Modified Tumor Targeted T Cells Enhances Anti-Tumor Efficacy Both in Vitro and in Vivo" Blood 120(21):4120 (2012).

Ramos et al., "Chimeric Antigen Receptor (CAR)-Engineered Lymphocytes for Cancer Therapy," Expert Opin Biol Ther.,11(7):855-873 (2011).

Brentjens et al., "Novel cellular therapies for leukemia: CAR-modified T cells targeted to the CD19 antigen," American Society of Hematology, pp. 143-151 (2012).

Celia et al., "Ligation Of CD40 on Dendritic Cells Triggers Production Of High Levels Of Interleukin-12 And Enhances T Cell Stimulatory Capacity: T-T Help Via APC Activation," The Journal Of Experimental Medicine 184(2):747-752 (1996).

Curran et al., "Enhancing Antitumor Efficacy of Chimeric Antigen Receptor T Cells Through Constitutive CD40L Expression," Mol. Ther 23(4):769-778 (2015).

Extended European Search Report dated Mar. 30, 2021 in European Application No. EP20179020.

Kowolik et al., "CD28 Costimulation Provided through a CD19-Specific Chimeric Antigen Receptor Enhances In vivo Persistence and Antitumor Efficacy of Adoptively Transferred T Cells," Cancer Research 66(22): 10995-11004 (2006).

Pegram et al., "Tumor-targeted T cells modified to secrete IL-12 eradicate systemic tumors without need for prior conditioning," Blood 119(18):4133-4141 (2012).

Wierda et al., "CD40-ligand (CD154) gene therapy for chronic lymphocytic leukemia," Blood 96:2917-2924 (2000).

\* cited by examiner

B6H12.2 scFv with kappa leader sequence

```
                    Kappa leader sequence
cc atg gag aca gac aca ctc ctg cta ctg ctc tgg gtt cca ggt tcc act ggt gac gag gtg cag ctg gtg gag tcc ggg gga ggc tta gtg
    M   E   T   D   T   L   L   L   L   W   V   P   G   S   T   G   D   E   V   Q   L   V   E   S   G   G   D   L   V
                                                                        B6H12.2 VH sequence
aag cct gga ggg tcc ctg aaa ctc tcc tgt gca gcc tct gga ttc act ttc agt ggc tat ggc atg tct tgg gtt cgc cag act cca gac aag agg ctg
 K   P   G   G   S   L   K   L   S   C   A   A   S   G   F   T   F   S   G   Y   G   M   S   W   V   R   Q   T   P   D   K   R   L
gag tgg gtc gca acc att agt ggt ggt act tac acc tac tat cca gac agt gtg aag ggg cga ttc acc atc tcc aga gac aat gcc aag aac acc ctg
 E   W   V   A   T   I   S   G   G   T   Y   T   Y   Y   P   D   S   V   K   G   R   F   T   I   S   R   D   N   A   K   N   T   L
tac ctg caa ata gac agc ctg aag tct gag gat aca gcc ata tat ttc tgt gca aga tcc ctc gcg gga aat gct atg gac tac tgg ggt caa gga acc
 Y   L   Q   I   D   S   L   K   S   E   D   T   A   I   Y   F   C   A   R   S   L   A   G   N   A   M   D   Y   W   G   Q   G   T
                     Serine Glycine linker sequence
tca gtc acc gtc tcc tca ggt gga ggc ggt tca gga gga ggt ggg tct ggc gga ggt ggg tct gac att gtg atg act cag tct cca gcc acc ctg tct
 S   V   T   V   S   S   G   G   G   G   S   G   G   G   G   S   G   G   G   G   S   D   I   V   M   T   Q   S   P   A   T   L   S
                                                                        B6H12.2 VL sequence
gtg act cca gga gat aga gtc tct ctt tcc tgc agg gcc agc cag act att agc gac tac tta cac tgg tat caa caa aaa tca cat gag tct cca agg ctt
 V   T   P   G   D   R   V   S   L   S   C   R   A   S   Q   T   I   S   D   Y   L   H   W   Y   Q   Q   K   S   H   E   S   P   R   L
ctc atc aaa ttt gct tcc caa tcc att tct ggg atc ccc tcc agg ttc agt ggc agt gga tca ggg aca gat ttc act ctc agt atc aac agt gtg gaa
 L   I   K   F   A   S   Q   S   I   S   G   I   P   S   R   F   S   G   S   G   S   G   T   D   F   T   L   S   I   N   S   V   E
cct gaa gat gtt ggc gtg tat tac tgt cag cag aat ggt cac ggc ttt cct cgg acg ttc ggt gga ggc acc aag ctg gaa atc aaa cgg gct gat gca gaa
 P   E   D   V   G   V   Y   Y   C   Q   Q   N   G   H   G   F   P   R   T   F   G   G   G   T   K   L   E   I   K
                                                          c-myc tag sequence
                                                          gaa caa aaa ctc atc
                                                           E   Q   K   L   I
tca gag gag gat ctg TAA ctc gag
 S   E   E   D   L   *   L   E
```

FIG. 3

B6H12.2scFv with CD8 leader sequence

```
cc atg gcc tta cca gtg acc ttg ctc ctg ccg ctc ctc cac gcc agg ccg gag gtg cag ctg gtg gag tcc ggg gga ggc tta gtg
   M   A   L   P   V   T   L   L   L   P   L   L   H   A   R   P   E   V   Q   L   V   E   S   G   G   D   L   V
                   [CD8 leader sequence]                              [B6H12.2 VH sequence → aag cct ggg ggg tcc ctg aaa ctc tcc tgt gca gcc tct gga ttc act ttc agt ggc tat ggc atg tct tgg gtt cgc cag act cca gag agg ctg
 K   P   G   G   S   L   K   L   S   C   A   A   S   G   F   T   F   S   G   Y   G   M   S   W   V   R   Q   T   P   D   K   R   L gag tgg gtc gca acc att act agt ggt ggt act tac acc tac tat cca gac agt gtg aag ggg cga ttc acc atc tcc aga gac aat gcc aag aac acc ctg
 E   W   V   A   T   I   T   S   G   G   T   Y   T   Y   Y   P   D   S   V   K   G   R   F   T   I   S   R   D   N   A   K   N   T   L tac ctg caa ata gac agc ctg aag tct gag gac aca gcc ata tat ttc tgt gca aga agt cta gct gga aat gct atg gac tac tgg ggt caa gga acc
 Y   L   Q   I   D   S   L   K   S   E   D   T   A   I   Y   F   C   A   R   S   L   A   G   N   A   M   D   Y   W   G   Q   G   T tca gtc acc gtc tcc tca ggt gga ggt ggg tca ggt gga ggt ggg tct ggt gga ggt ggg tct gac att gtg atg act cag tct cca gcc acc ctg tct
 S   V   T   V   S   S   G   G   G   G   S   G   G   G   G   S   G   G   G   G   S   D   I   V   M   T   Q   S   P   A   T   L   S
 ← B6H12.2 VH sequence]  [Serine glycine linker sequence]            [B6H12.2 VL sequence → gtg act cca gga gat aga gtc tct ctt tcc tgc agg gcc agc cag act att agc gac tac tta cac tgg tat caa caa aaa tca cat gag tct cca agg ctt
 V   T   P   G   D   R   V   S   L   S   C   R   A   S   Q   T   I   S   D   Y   L   H   W   Y   Q   Q   K   S   H   E   S   P   R   L ctc atc aaa ttt gct tcc caa tcc atc tct ggg atc ccc tcc agg ttc agt ggc agt gga tca ggg tca gat ttc act ctc agt atc aac agt gtg gaa
 L   I   K   F   A   S   Q   S   I   S   G   I   P   S   R   F   S   G   S   G   S   G   S   D   F   T   L   S   I   N   S   V   E cct gaa gat gtt ggt gtg tat tac tgt caa aat ggt cac cag ttt cct cgg acg ttc ggt gga ggc acc aag ctg gaa atc aaa gaa caa aaa ctc atc
 P   E   D   V   G   V   Y   Y   C   Q   N   G   H   Q   F   P   R   T   F   G   G   G   T   K   L   E   I   K   E   Q   K   L   I
                                                           ← B6H12.2 VL sequence]               [c-myc tag sequence → tca gaa gag gat ctg TAA ctc gag
 S   E   E   D   L   *   L   E
 ← c-myc tag sequence]
```

FIG. 4

1928z-2A-B6H12.2 (kappa leader) sequence

```
atggctctcccagtgactgccctactgcttccccctagcgcttctcctgcatgcagaggtgaagctgcagcagtctggg
gctgagctggtgaagcctgggtcctcagtgaagatttcctgcaaggcttctggctatgcattcagtagctactggatgaa
ctgggtgaagcagaggcctggacagggtcttgagtggattggacagatttatcctggagatggtgatactaactacaat
ggaaagttcaagggtcaagccacactgactgcagacaaatcctccagcacagcctacatgcagctcagcggcctaacat
ctgaggactctgcggtctatttctgtgcaagaaagaccattagttcggtagtagatttctactttgactactggggccaagg
gaccacggtcaccgtctcctcaggtggaggtggatcaggtggaggtggatctggtggaggtggatctgacattgagc
tcacccagtctccaaaattcatgtccacatcagtaggagacagggtcagcgtcacctgcaaggccagtcagaatgtgggt
actaatgtagcctggtatcaacagaaaccaggacaatctcctaaaccactgatttactcggcaacctaccggaacagtgg
agtccctgatcgcttcacaggcagtggatctgggacagatttcactctcaccatcactaacgtgcagtctaaagacttggc
agactatttctgtcaacaatataacaggtatccgtacacgtccggaggggggaccaagctggagatcaaacgggcggc
cgcaattgaagttatgtatcctcctccttacctagacaatgagaagagcaatggaaccattatccatgtgaagggaaaca
cctttgtccaagtcccctatttcccggaccttctaagccctttgggtgctggtggtggttggtggagtcctggcttgctata
gcttgtagtaacagtggcctttattattttctgggtgaggagtaagaggagcaggctcctgcacagtgactacatgaac
atgactccccgccgcccgggcccaccccgcaagcattaccagccctatgccccaccacgcgacttcgcagcctatcgctc
cagagtgaagttcagcaggagcgcagagccccccgcgtaccagcagggccagaaccagctctataacgagctcaatct
aggacgaagagaggagtacgatgtttttggacaagagacgtggccgggaccctgagatggggggaaagccgagaag
gaagaccctcaggaaggcctgtacaatgaactgcagaaagataagatggcggaggcctacagtgagattgggatga
aaggcgagcgccggaggggcaaggggcacgatggcctttaccagggtctcagtacagccaccaaggacacctacga
cgccctccacatgcaggccctgcccccctcgcggatctggagcaacaaacttctcactactcaaacaagcaggtgacgtgg
aggagaatcccggacccatggagacagacacactcctgctatgggtactgctgctctgggttccaggttccactggtgac
gaggtgcagctggtggagtccggggggagacttagtgaagcctggagggtccctgaaactctcctgtgcagcctctgga
ttcactttcagtggctatggcatgtcttgggttcgccagactccagacaagaggctggagtgggtcgcaaccattactagt
ggtggtacttacacctactatccagacagtgtgaaggggcgattcaccatctccagagacaatgccaagaacaccctgta
cctgcaaatagacagtctgaagtctgaggatacagccatatatttctgtgcaagatccctcgcgggaaatgctatggacta
ctggggtcaaggaacctcagtcaccgtctcctcaggtggaggtggatcaggtggaggtggatctggtggaggtggatc
tgacattgtgatgactcagtctccagccaccctgtctgtgactccaggagatagagtctctctttcctgcagggccagccag
actattagcgactacttacactggtatcaacaaaaatcacatgagtctccaaggcttctcatcaaatttgcttcccaatccattt
ctgggatcccctccaggttcagtggcagtggatcaggctcagatttcactctcagtatcaacagtgtggaacctgaagatg
ttggagtgtattactgtcaaaatggtcacggcttcctcggacgttcggtggaggcaccaagctggaaatcaaagaacaa
aaactcatctcagaagaggatctgtaa
```

— 1928z CAR
— P2A
— B6H12.2 scFv

FIG. 5

4H1128z-2A-B6H12.2 (kappa leader) sequence

```
CATGGCTCTCCCAGTGACTGCCCTACTGCTTCCCCTAGCGCTTCTCCTGCATGCAGAGGTGAAG
CTGCAGGAGTCAGGGGGAGGCTTCGTGAAGCCTGGAGGGTCCCTCAAAGTCTCCTGTGCAGC
CTCTGGATTCACTTTCAGTAGCTATGCCATGTCCTGGGTTCGCCTGAGTCCGGAGATGAGGCTG
GAGTGGGTCGCAACCATTAGCAGTGCTGGTGGTTACATCTTCTATTCTGACAGTGTGCAGGGA
CGATTCACCATTTCCAGAGACAATGCCAAGAACACCCTGCACCTGCAAATGGGCAGTCTGAGG
TCTGGGGACACGGCCATGTATTACTGTGCAAGGCAGGGATTTGGTAACTACGGTGATTACTATG
CTATGGACTACTGGGGCCAAGGGACCACGGTCACCGTCTCCTCAGGTGGAGGTGGATCAGGT
GGAGGTGGATCTGGTGGAGGTGGATCTGACATTGAGCTCACCCAGTCTCCATCCTCCCTGGCT
GTGTCAGCAGGAGAGAAGGTCACTATGAGCTGCAAATCCAGTCAGAGTCTGCTCAACAGTAG
AACCCGAAAGAACCAGTTGGCTTGGTACCAGCAAAAACCAGGACAGTCTCCTGAACTGCTG
ATCTACTGGGCATCCACTAGGCAATCTGGAGTCCCTGATCGCTTCACAGGCAGTGGATCTGGG
ACAGATTTCACTCTCACCATCAGCAGTGTGCAGGCTGAAGACCTGGCAGTTTATTACTGCCAG
CAATCTTATAATCTACTgcaacaaacttctcactactcaaacaagcaggtgacgtggaggagaatcccggacccat-
ggagacagacacactcctgctatgggtactgctgctctgggttccaggttccactggtgacgaggtgcagctggtggag
tccggggagacttagtgaagcctggagggtccctgaaactctcctgtgcagcctctggattcactttcagtggctatgg
catgtcttgggttcgccagactccagacaagaggctggagtgggtcgcaaccattactagtggtggtacttacacctact
atccagacagtgtgaaggggcgattcaccatctccagagacaatgccaagaacacccgtacctgcaaatagacagtct
gaagtctgaggatacagccatatatttctgtgcaagatcccctcgcgggaaatgctatggactactggggtcaaggaacc
tcagtcaccgtctcctcaggtggaggtggatcaggtggaggtggatctggtggaggtggatctgacattgtgatgact
cagtctccagccaccctgtctgtgactccaggagatagagtctctctttcctgcagggccagccagactattagcgacta
cttacactggtatcaacaaaaatcacatgagtctccaaggcttctcatcaaatttgcttcccaatccatttctgggatccct
ccaggttcagtggcagtggatcaggctcagatttcactctcagtatcaacagtgtggaacctgaagatgttggagtgtat
tactgtcaaaatggtcacggctttcctcggacgttcggtggaggcaccaagctggaaatcaaagaacaaaaactcatct
cagaagaggatctgtaa
```

(Annotations on right margin: 4H1128z CAR, P2A, B6H12.2 scFv)

FIG. 6

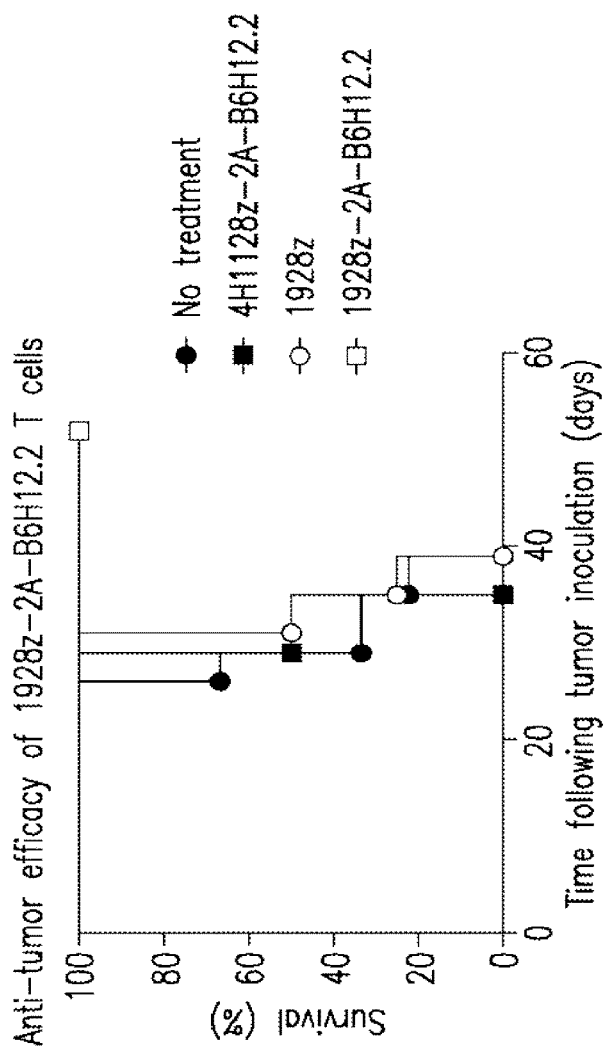
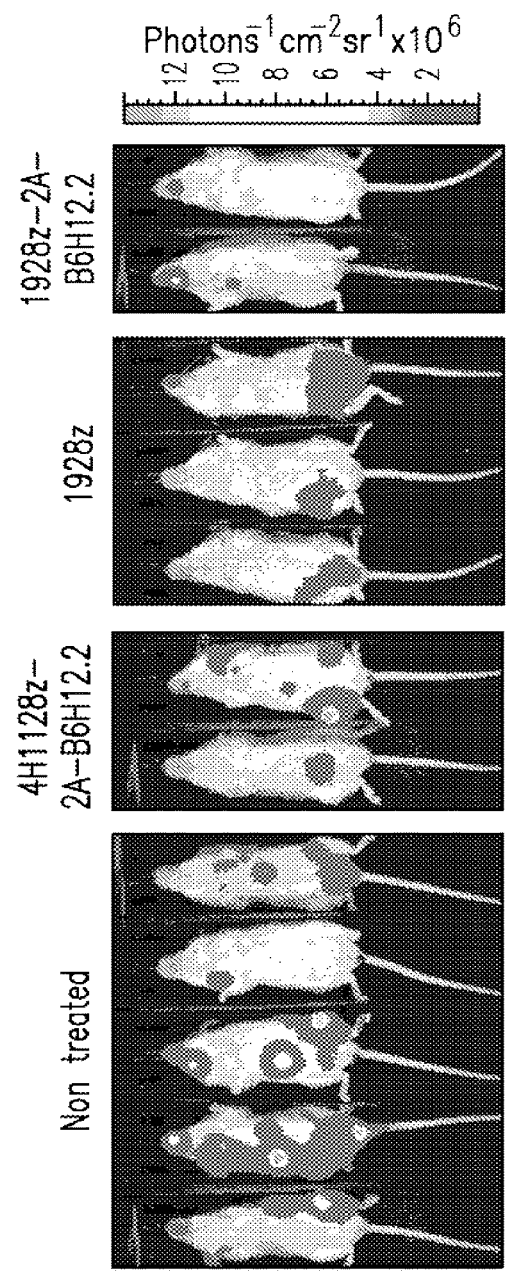
FIG. 10A
FIG. 10B

5C4scFv with Kappa leader sequence

Kappa leader sequence:
ATG GAG ACA GAC ACA CTC CTG CTA TGG GTA CTG CTG CTC TGG GTT CCA GGT TCC ACT GGT GAC
 M   E   T   D   T   L   L   L   W   V   L   L   L   W   V   P   G   S   T   G   D CAG GTG CAG CTG GTG GAG TCT GGG GGA GGC GTG GTC
 Q   V   Q   L   V   E   S   G   G   G   V   V CAG CCT GGG AGG TCC CTG AGA CTC TCC TGT AAA GCG TCT GGA ATC ACC TTC AGT AAC TCT GGC ATG CAC TGG GTC CGC CAG GCT CCA GGC AAG GGG CTG
 Q   P   G   R   S   L   R   L   S   C   K   A   S   G   I   T   F   S   N   S   G   M   H   W   V   R   Q   A   P   G   K   G   L 5C4 VH sequence GAG TGG GTG GCA GTT ATT TGG TAT GAT GGA AGT AAT AAA TAC TAT GCA GAC TCC GTG AAG GGC CGA TTC ACC ATC TCC AGA GAC AAC TCC AAG AAC ACG
 E   W   V   A   V   I   W   Y   D   G   S   N   K   Y   Y   A   D   S   V   K   G   R   F   T   I   S   R   D   N   S   K   N   T CTG TTT CTG CAA ATG AAC AGC CTG AGA GCC GAG GAC ACG GCT GTG TAT TAC TGT GCG ACA AAT GAC GAC GAC TAC TGG GGC CAG GGA ACC CTG GTC ACC GTC
 L   F   L   Q   M   N   S   L   R   A   E   D   T   A   V   Y   Y   C   A   T   N   D   D   D   Y   W   G   Q   G   T   L   V   T   V Serine glycine linker sequence
TCC TCA GGT GGA GGC GGT TCA GGC GGA GGT GGC TCT GGC GGT GGC GGA TCG
 S   S   G   G   G   G   S   G   G   G   G   S   G   G   G   G   S GAA ATT GTG TTG ACA CAG TCT CCA GCC ACC CTG TCT TTG TCT CCA GGG
 E   I   V   L   T   Q   S   P   A   T   L   S   L   S   P   G 5C4 VL sequence GAA AGA GCC ACC CTC TCC TGC AGG GCC AGT CAG AGT GTT AGT AGT TAC TTA GCC TGG TAC CAA CAG AAA CCT GGC CAG GCT CCC AGG CTC CTC ATC TAT GAT
 E   R   A   T   L   S   C   R   A   S   Q   S   V   S   S   Y   L   A   W   Y   Q   Q   K   P   G   Q   A   P   R   L   L   I   Y   D GCA TCC AAC AGG GCC ACT GGC ATC CCA GCC AGG TTC AGT GGC AGT GGG TCT GGG ACA GAC TTC ACT CTC ACC ATC AGC AGC CTA GAG CCT GAA GAT TTT GCA
 A   S   N   R   A   T   G   I   P   A   R   F   S   G   S   G   S   G   T   D   F   T   L   T   I   S   S   L   E   P   E   D   F   A GTT TAT TAC TGT CAG CAG AGT AAC AAC TGG CCT CGG ACG TTC GGC CAA GGG ACC AAG GTG GAA ATC AAA GAA CAA AAA CTC ATC TCA GAA GAG GAT CTG TAA
 V   Y   Y   C   Q   Q   S   N   N   W   P   R   T   F   G   Q   G   T   K   V   E   I   K   E   Q   K   L   I   S   E   E   D   L   * c-myc tag sequence

FIG. 11

1928z-2A-5C4 (kappa leader) sequence

```
atggctctcccagtgactgccctactgcttcccctagcgcttctcctgcatgcagaggtgaagctgcagcagtctggg
gctgagctggtgaggcctgggtcctcagtgaagatttcctgcaaggcttctggctatgcattcagtagctactggatgaa
ctgggtgaagcagaggcctggacagggtcttgagtggattggacagatttatcctggagatggtgatactaactacaat
ggaaagttcaagggtcaagccacactgactgcagacaaatcctccagcacagcctacatgcagctcagcggcctaacat
ctgaggactctgcggtctatttctgtgcaagaaagaccattagttcggtagtagatttctactttgactactggggccaagg
gaccacggtcaccgtctcctcaggtggaggtggatcaggtggaggtggatctggtggaggtggatctgacattgagc
tcacccagtctccaaaattcatgtccacatcagtaggagacagggtcagcgtcacctgcaaggccagtcagaatgtgggt
actaatgtagcctggtatcaacagaaaccaggacaatctcctaaaccactgatttactcggcaacctaccggaacagtgg
agtccctgatcgcttcacaggcagtggatctgggacagatttcactctcaccatcactaacgtgcagtctaaagacttggc
agactatttctgtcaacaatataacaggtatccgtacacgtccggaggggggaccaagctggagatcaaacgggcggc
cgcaattgaagttatgtatcctcctccttacctagacaatgagaagagcaatggaaccattatccatgtgaaagggaaaca
cctttgtccaagtccccctatttccggaccttctaagcccttttgggtgctggtggtggttggtggagtcctggcttgctata
gcttgctagtaacagtggcctttattatttctgggtgaggagtaagaggagcaggctcctgcacagtgactacatgaac
atgactccccgccgccccgggccccaccgcaagcattaccagccctatgccccaccacgcgacttcgcagcctatcgctc
cagagtgaagttcagcaggagcgcagagccccccgcgtaccagcagggccagaaccagctctataacgagctcaatct
aggacgaagagaggagtacgatgttttggacaagagacgtggccgggaccctgagatggggggaaagccgagaag
gaagaaccctcaggaaggcctgtacaatgaactgcagaaagataagatggcggaggcctacagtgagattgggatga
aaggcgagcgccggaggggcaaggggcacgatggcctttaccagggtctcagtacagccaccaaggacacctacga
cgccttcacatgcaggccctgccccctcgcggatctggagcaacaaattctcactactcaaacaagcaggtgacgtgg
aggagaatcccggacccATGGAGACAGACACACTCCTGCTATGGGTACTGCTGCTCTGGGTTCCAGG
TTCCACTGGTGACCAGGTGCAGCTGGTGGAGTCTGGGGGAGGCGTGGTCCAGCCTGGGAGGT
CCCTGAGACTCGACTGTAAAGCGTCTGGAATCACCTTCAGTAACTCTGGCATGCACTGGGTCCG
CCAGGCTCCAGGCAAGGGGCTGGAGTGGGTGGCAGTTATTTGGTATGATGGAAGTAAAAGATA
CTATGCAGACTCCGTGAAGGGCCGATTCACCATCTCCAGAGACAATTCCAAGAACACGCTGTTT
CTGCAAATGAACAGCCTGAGAGCCGAGGACACGGCTGTGTATTACTGTGCGACAAACGACGAC
TACTGGGGCCAGGGAACCCTGGTCACCGTCTCCTCAGGTGGAGGTGGATCAGGTGGAGGTGGA
TCTGGTGGAGGTGGATCTGAAATTGTGTTGACACAGTCTCCAGCCACCCTGTCTTTGTCTCCAGG
GGAAAGAGCCACCCTCTCCTGCAGGGCCAGTCAGAGTGTTAGTAGTTACTTAGCCTGGTACCAA
CAGAAACCTGGCCAGGCTCCCAGGCTCCTCATCTATGATGCATCCAACAGGGCCACTGGCATCC
CAGCCAGGTTCAGTGGCAGTGGGTCTGGGACAGACTTCACTCTCACCATCAGCAGCCTAGAGC
CTGAAGATTTTGCAGTTTATTACTGTCAGCAGAGTAGCAACTGGCCTCGGACGTTCGGCCAAGG
GACCAAGGTGGAAATCAAAGAACAAAAACTCATCTCAGAAGAGGATCTGTAACTCGAGGATCC
```

1928z CAR · P2A · sC4 scFv

FIG. 12

4H1128Z-2A-5C4 (kappa leader) sequence

```
CATGGCTCTCCCAGTGACTGCCCTACTGCTTCCCCTAGCGCTTCTCCTGCATGCAGAGGTGAAG  ┐
CTGCAGGAGTCAGGGGGAGGCTTCGTGAAGCCTGGAGGGTCCCTCAAAGTCTCCTGTGCAGC    │
CTCTGGATTCACTTTCAGTAGCTATGCCATGTCCTGGGTTCGCCTGAGTCCGGAGATGAGGCTG  │
GAGTGGGTCGCAACCATTAGCAGTGCTGGTGGTTACATCTTCTATTCTGACAGTGTGCAGGGA   │
CGATTCACCATTTCCAGAGACAATGCCAAGAACACCCTGCACCTGCAAATGGGCAGTCTGAGG   │
TCTGGGGACACGGCCATGTATTACTGTGCAAGGCAGGGATTTGGTAACTACGGTGATTACTATG  │ 4H1128z CAR
CTATGGACTACTGGGGCCAAGGGACCACGGTCACCGTCTCCTCAGGTGGAGGTGGATCAGGT    │
GGAGGTGGATCTGGTGGAGGTGGATCTGACATTGAGCTCACCCAGTCTCCATCCTCCCTGGCT   │
GTGTCAGCAGGAGAGAAGGTCACTATGAGCTGCAAATCCAGTCAGAGTCTGCTCAACAGTAG    │
AACCCGAAAGAACCAGTTGGCTTGGTACCAGCAAAAACCAGGACAGTCTCCTGAACTGCTG     │
ATCTACTGGGCATCCACTAGGCAATCTGGAGTCCCTGATCGCTTCACAGGCAGTGGATCTGGG   │
ACAGATTTCACTCTCACCATCAGCAGTGTGCAGGCTGAAGACCTGGCAGTTTATTACTGCCAG   │
CAATCTTATAATCTACTgcaacaaacttctcactactcaaacaagcaggtgacgtggaggagaatcccggaccc  ┘ — P2A
ATGGAGACAGACACACTCCTGCTATGGGTACTGCTGCTCTGGGTTCCAGGTTCCACTGGTGA    ┐
CCAGGTGCAGCTGGTGGAGTCTGGGGGAGGCGTGGTCCAGCCTGGGAGGTCCCTGAGACT      │
CGACTGTAAAGCGTCTGGAATCACCTTCAGTAACTCTGGCATGCACTGGGTCCGCCAGGCTC    │
CAGGCAAGGGGCTGGAGTGGGTGGCAGTTATTTGGTATGATGGAAGTAAAAGATACTATGC     │
AGACTCCGTGAAGGGCCGATTCACCATCTCCAGAGACAATTCCAAGAACACGCTGTTTCTGC    │
AAATGAACAGCCTGAGAGCCGAGGACACGGCTGTGTATTACTGTGCGACAAACGACGACTA     │
CTGGGGCCAGGGAACCCTGGTCACCGTCTCCTCAGGTGGAGGTGGATCAGGTGGAGGTGGA     │ SC4 scFv
TCTGGTGGAGGTGGATCTGAAATTGTGTTGACACAGTCTCCAGCCACCCTGTCTTTGTCTCCA   │
GGGGAAAGAGCCACCCTCTCCTGCAGGGCCAGTCAGAGTGTTAGTAGTTACTTAGCCTGGTA    │
CCAACAGAAACCTGGCCAGGCTCCCAGGCTCCTCATCTATGATGCATCCAACAGGGCCACTG    │
GCATCCCAGCCAGGTTCAGTGGCAGTGGGTCTGGGACAGACTTCACTCTCACCATCAGCAG     │
CCTAGAGCCTGAAGATTTTGCAGTTTATTACTGTCAGCAGAGTAGCAACTGGCCTCGGACGT    │
TCGGCCAAGGGACCAAGGTGGAAATCAAAGAACAAAAACTCATCTCAGAAGAGGATCTGTA     │
ACTCGAGGATCC                                                       ┘
```

```
                                           J43 VL sequence
ACA GCC ACC TTG ACC ATC AGA GAT GTC CGG CCT GAG GAT GAA GGT GAC TGT TTC TCA GGA TAT GTT GAT AGT GAT AGC AAA TTG TAT GTT TTT GGC
 T   A   T   L   T   I   R   D   V   R   P   E   D   E   G   D   C   F   S   G   Y   V   D   S   D   S   K   L   Y   V   F   G AGC GGA ACC CAG CTC ACC GTC CTA GGT GGA CCC AAA GTC ACA GTG TTT CCA CCT TCA CCT GAG GAG CTC CGG ACA AAC AAA GCC ACA
 S   G   T   Q   L   T   V   L   G   G   P   K   V   T   V   F   P   P   S   P   E   E   L   R   T   N   K   A   T CTG GTG TGT CTG GTT AAT GAC TTC TAC CCG GGT TCT GCA ACA GTG ACC TGG AAG GCA AAT GGA ACT ATC AAT GAT GGG GTG AAG ACT ACA AAG CCT
 L   V   C   L   V   N   D   F   Y   P   G   S   A   T   V   T   W   K   A   N   G   A   T   I   N   D   G   V   K   T   T   K   P TCC AAA CAG GGC CAA AAC TAC ATG AGC AGC TAC CTA AGT TTG ACA GAC CAG TGG AAA TCT CAC AAC AGG GTT TCC TGC CAA GTT ACC CAT GAA
 S   K   Q   G   Q   N   Y   M   S   S   Y   L   S   L   T   D   Q   W   K   S   H   N   R   V   S   C   Q   V   T   H   E c-myc tag sequence
GGG GAA ACT GTG GAG AAG AGT TTG TCC CCT GCA GAA CTC CAA GAA CAA AAA CTC ATC TCA GAA GAG GAT CTG TAA
 G   E   T   V   E   K   S   L   S   P   A   E   C   L   E   Q   K   L   I   S   E   E   D   L   *
```

FIG. 18 continued

19m28mzIRESJ43(mouse Kappa leader)sequence

```
CATGGCTCTCCCAGTGACTGCCCTACTGCTTCCCCTAGCGCTTCTCCTGCATGCAGAGGTGAAGCTGCAGCAGTCTGGGG
CTGAGCTGGTGAGGCCTGGGTCCTCAGTGAAGATTTCCTGCAAGGCTTCTGGCTATGCATTCAGTAGCTACTGGATGAAC
TGGGTGAAGCAGAGGCCTGGACAGGGTCTTGAGTGGATTGGACAGATTTATCCTGGAGATGGTGATACTAACTACAATGG
AAAGTTCAAGGGTCAAGCCACACTGACTGCAGACAAATCCTCCAGCACAGCCTACATGCAGCTCAGCGGCCTAACATCTG
AGGACTCTGCCGTCTATTTCTGTGCAAGAAAGACCATTAGTTCGGTAGTAGATTTCTACTTTGACTACTGGGGCCAAGGG
ACCACGGTCACCGTCTCCTCAGGTGGAGGTGGATCAGGTGGAGGTGGATCTGGTGGAGGTGGATCTGACATTGAGCTCAC
CCAGTCTCCAAAATTCATGTCCACATCAGTAGGAGACAGGGTCAGCGTCACCTGCAAGGCCAGTCAGAATGTGGGTACTA
ATGTAGCCTGGTATCAACAGAAACCAGGACAATCTCCTAAACCACTGATTTACTCGGCAACCTACCGGAACAGTGGAGTC
CCTGATCGCTTCACAGGCAGTGGATCTGGGACAGATTTCACTCTCACCATCACTAACGTGCAGTCTAAAGACTTGGCAGA
CTATTTCTGTCAACAATATAACAGGTATCCGTACACGTCCGGAGGGGGGACCAAGCTGGAGATCAAACGGGCGGCCCCAA
TTGAGTTCATGTACCCTCCGCCTTACCTAGACAACGAGAGGAGCAATGGAACTATTATTCACATAAAAGAGAAACATCTT
TGTCATACTCAGTCATCTCCTAAGCTGTTTTGGGCACTGGTCGTGGTTGCTGGAGTCCTGTTTTGTTATGGCTTGCTAGT
GACAGTGGCTCTTTGTGTTATCTGGACAAATAGTAGAAGGAACAGACTCCTTCAAAGTGACTACATGAACATGACTCCCC
GGAGGCCTGGGCTCACTCGAAAGCCTTACCAGCCCTACGCCCCTGCCAGAGACTTTGCAGCGTACCGCCCCAGAGCAAAA
TTCAGCAGGAGTGCAGAGACTGCTGCCAACCTGCAGGACCCCAACCAGCTCTACAATGAGCTCAATCTAGGGCGAAGAGA
GGAATATGACGTCTTGGAGAAGAAGCGGGCTCGGGATCCAGAGATGGGAGGCAAACAGCAGAGGAGGAGGAACCCCCAGG
AAGGCGTATACAATGCACTGCAGAAAGACAAGATGGCAGAAGCCTACAGTGAGATCGGCACAAAAGCCGAGAGACGGAGA
GGCAAGGGGCACGATGGCCTTTACCAGGGTCTCAGCACTGCCACCAAGGACACCTATGATGCCCTGCATATGCAGACCCT
GGCCCCTCGCTAACAGCCA
```

19m28mzCAR

```
```

IRES

```
CCATGGAGACAGACACACTCC
TGCTATGGGTACTGCTGCTCTGGGTTCCAGGTTCCACTGGTGACATGGGATTGGGACTGCAGTGGGTTTTCTTTGTTGCT
CTTTTAAAGGTGTCCACTGTGAGGTGCGGCTTCTGGAGTCTGGTGGAGGATTAGTGAAGCCTGAGGGGTCACTGAAACT
CTCCTGTGTGGCCTCTGGATTCACCTTCAGTGACTATTTCATGAGCTGGGTCCGCCAGGCTCCAGGGAAGGGGCTGGAGT
GGGTTGCTCACATATACACGAAAAGTTATAATTATGCAACTTATTACTCGGGTTCGGTGAAAGGCAGATTCACCATCTCC
AGAGATGATTCCCGAAGCATGGTCTACCTGCAAATGAACAACCTGAGAACTGAGGACACGGCCACTTATTACTGTACAAG
AGATGGAAGCGGATATCCCTCTCTGGATTTCTGGGGTCAAGGGACCCAAGTCACTGTCTCCTCAGCCACAACAACAGCCC
CATCTGTCTATCCCTTGGCCCCTGCCTGTGACAGCACAACCAAATCGGGTGGAGGTGGATCAGGTGGAGGTGGATCTGGT
GGAGGTGGATCTTATGAGCTGACTCAGCCACCTTCAGCATCAGTCAATGTAGGAGAGACTGTCAAAATCACCTGCTCTGG
GGACCAATTGCCGAAATATTTTGCAGATTGGTTTCATCAAAGGTCAGACCAGACCATTTTGCAAGTGATATATGATGATA
ATAAGCGCCCCTCGGGGATCCCTGAAAGAATCTCTGGGTCCAGCTCAGGGACAACAGCCACCTTGACCATCAGAGATGTC
CGGGCTGAGGATGAAGGTGACTATTACTGTTTCTCAGGATATGTTGATAGTGATAGCAAATTGTATGTTTTGGCAGCGG
AACCCAGCTCACCGTCCTAGGTGGACCCAAGTCTTCTCCCAAAGTCACAGTGTTTCCACCTTCACCTGAGGAGCTCCGGA
CAAACAAAGCCACACTGGTGTGTCTGGTTAATGACTTCTACCCGGGTTCTGCAACAGTGACCTGGAAGGCAAATGGAGCA
ACTATCAATGATGGGGTGAAGACTACAAAGCCTTCCAAACAGGGCCAAAACTACATGACCAGCAGCTACCTAAGTTTGAC
AGCAGACCAGTGGAAATCTCACAACAGGGTTTCCTGCCAAGTTACCCATGAAGGGGAAACTGTGGAGAAGAGTTTGTCCC
CTGCAGAATGTCTCGAACAAAAACTCATCTCAGAAGAGGATCTGTAACTCGAG
```

J43 scFv

FIG. 19

4H11m28mzIRESJ43(mouse Kappa leader)sequence

```
CTCTCCCAGTGACTGCCCTACTGCTTCCCCTAGCGCTTCTCCTGCATGCAGAGGTGAAGCTGCAGGAGTCAGGGGGAGGC
TTCGTGAAGCCTGGAGGGTCCCTCAAAGTCTCCTGTGCAGCCTCTGGATTCACTTTCAGTAGCTATGCCATGTCCTGGGT
TCGCCTGAGTCCGGAGATGAGGCTGGAGTGGGTCGCAACCATTAGCAGTGCTGGTGGTTACATCTTCTATTCTGACAGTG
TGCAGGGACGATTCACCATTTCCAGAGACAATGCCAAGAACACCCTGCACCTGCAAATGGGCAGTCTGAGGTCTGGGGAC
ACGGCCATGTATTACTGTGCAACGCAGGGATTTGGTAACTACGGTGATTACTATGCTATGGACTACTGGGGCCAAGGGAC
CACGGTCACCGTCTCCTCAGGTGGAGGTGGATCAGGTGGAGGTGGATCTGGTGGAGGTGGATCTGACATTGAGCTCACCC
AGTCTCCATCCTCCCTGGCTGTGTCAGCAGGAGAGAAGGTCACTATGAGCTGCAAATCCAGTCAGAGTCTGCTCAACAGT
AGAACCCGAAAGAACCAGTTGGCTTGGTACCAGCAAAAACCAGGACAGTCTCCTGAACTGCTGATCTACTGGGCATCCAC
TAGGCAATCTGGAGTCCCTGATCGCTTCACAGGCAGTGGATCTGGGACAGATTTCACTCTCACCATCAGCAGTGTGCAGG
CTGAAGACCTGGCAGTTTATTACTGCCAGCAATCTTATAATCTACTGGGACCAAGCTGGAGATCAAACGGGCGGCCGCAA
TTGAGTTCATGTACCCTCCGCCTTACCTAGACAACGAGAGGAGCAATGGAACTATTATTCACATAAAAGAGAAACATCTT
TGTCATACTCAGTCATCTCCTAAGCTGTTTTGGGCACTGGTCGTGGTTGCTGGAGTCCTGTTTTGTTATGCCTTGCTAGT
GACAGTGGCTCTTTGTGTTATCTGGACAAATAGTAGAAGGAACAGACTCCTTCAAAGTGACTACATGAACATGACTCCCC
GGAGGCCTGGGCTCACTCGAAAGCCTTACCAGCCCTACGCCCCTGCCAGAGACTTTGCAGCGTACCGCCCCAGAGCAAAA
TTCAGCAGGAGTGCAGAGACTGCTGCCAACCTGCAGGACCCCAACCAGCTCTACAATGAGCTCAATCTAGGGCCAAGAGA
GGAATATGACGTCTTGGAGAAGAAGCGGGCTCGGGATCCAGAGATGGGAGGCAAACAGCAGAGGAGGAGGAACCCCCAGG
AAGGCGTATACAATGCACTGCAGAAAGACAAGATGGCAGAAGCCTACAGTGAGATCGGCACAAAAGGCGAGAGGCGGAGA
GGCAAGGGGCACGATGGCCTTTACCAGGGTCTCAGCACTGCCACCAAGGACACCTATGATGCCCTGTATATGCAGACCCT
GGCCCCTCGCTAACAGCCACTCCACCA_____
_____
_____
_____
_____
_____
_____
_____CCATGGAGACAGACACACTCC
TGCTATGGGTACTGCTGCTCTGGGTTCCAGGTTCCACTGGTGACATGGGATTGGGACTGCAGTGGGTTTTCTTTGTTGCT
CTTTTAAAGGTGTCCACTGTGAGGTGCGGCTTCTGGAGTCTGGTGGAGGATTAGTGAAGCCTGAGGGGTCACTGAAACT
CTCCTGTGTGGCCTCTGGATTCACCTTCAGTGACTATTTCATGAGCTGGGTCCGCCAGGCTCCAGGGAAGGGGCTCGAGT
GGGTTGCTCACATATACACGAAAAGTTATAATTATGCAACTTATTACTCGGGTTCGGTGAAAGGCAGATTCACCATCTCC
AGAGATGATTCCCGAAGCATGGTCTACCTGCAAATGAACAACCTGAGAACTGAGGACACGGCCACTTATTACTGTACAAG
AGATGGAAGCGGATATCCCTCTCTGGATTTCTGGGGTCAAGGGACCCAAGTCACTGTCTCCTCAGCCACAACAACAGCCC
CATCTGTCTATCCCTTGGCCCCTGCCTGTGACAGCACAACCAAATCGGTGGAGGTGGATCAGGTGGAGGTGGATCTGGT
GGAGGTGGATCTTATGAGCTGACTCAGCCACCTTCAGCATCAGTCAATGTAGGAGAGACTGTCAAAATCACCTGCTCTGG
GGACCAATTGCCCGAAATATTTTGCAGATTGGTTTCATCAAAGGTCAGACCAGACCATTTTGCAAGTGATATATGATGATA
ATAAGCGCCCCTCGGGGATCCCTGAAAGAATCTCTGGGTCCAGCTCAGGGACAACAGCCACCTTGACCATCAGAGATGTC
CGGGCTGAGGATGAAGGTGACTATTACTGTTTCTCAGGATATGTTGATAGTGATAGCAAATTGTATGTTTTTGGCAGCGG
AACCCAGCTCACCGTCCTAGGTGGACCCAAGTCTCTCCCAAAGTCACAGTGTTTCCACCTTCACCTGAGGAGCTCCGGA
CAAACAAAGCCACACTGGTGTGTCTGGTTAATGACTTCTACCCGGGTTCTGCAACAGTGACCTGGAAGGCAAATGGAGCA
ACTATCAATGATGGGGTGAAGACTACAAAGCCTTCCAAACAGGGCCAAAACTACATGACCAGCAGCTACCTAAGTTTGAC
AGCAGACCAGTGGAAATCTCACAACAGGGTTTCCTGCCAAGTTACCCATGAAGGGGAAACTGTGGAGAAGAGTTTGTCCC
CTGCAGAATGTCTCGAACAAAAAACTCATCTCAGAAGAGGATCTGTAACTCGAG
```

4H11m28mz CAR / IRES / J43 scFv

FIG. 20

SEQUENCE LISTING

```
<160> NUMBER OF SEQ ID NOS: 56

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 220
<212> TYPE: PRT
<213> ORGANISM: Homo sapiens

<400> SEQUENCE: 2

Met Leu Arg Leu Leu Leu Ala Leu Asn Leu Phe Pro Ser Ile Gln Val
1               5                   10                  15
```

Thr Gly Asn Lys Ile Leu Val Lys Gln Ser Pro Met Leu Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacgtgcatg atcgaaacat acaaccaaac ttctccccga tctgc            45

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcgagggat cctcagagtt tgagtaagcc aaagga                      36

<210> SEQ ID NO 5
<211> LENGTH: 255
<212> TYPE: PRT
<213> ORGANISM: Homo sapiens

<400> SEQUENCE: 5

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

```
Ala Gly Thr Phe Cys Asp Asn Asn Arg Asn Gln Ile Cys Ser Pro Cys
            35                  40                  45
Pro Pro Asn Ser Phe Ser Ser Ala Gly Gly Gln Arg Thr Cys Asp Ile
 50                  55                  60
Cys Arg Gln Cys Lys Gly Val Phe Arg Thr Arg Lys Glu Cys Ser Ser
 65                  70                  75                  80
Thr Ser Asn Ala Glu Cys Asp Cys Thr Pro Gly Phe His Cys Leu Gly
                 85                  90                  95
Ala Gly Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
            180                 185                 190
Ala Leu Thr Ser Thr Ala Leu Leu Phe Leu Leu Phe Phe Leu Thr Leu
            195                 200                 205
Arg Phe Ser Val Val Lys Arg Gly Arg Lys Lys Leu Leu Tyr Ile Phe
            210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255

<210> SEQ ID NO 6
<211> LENGTH: 183
<212> TYPE: PRT
<213> ORGANISM: Homo sapiens

<400> SEQUENCE: 6

Met Glu Arg Val Gln Pro Leu Glu Glu Asn Val Gly Asn Ala Ala Arg
 1               5                  10                  15
Pro Arg Phe Glu Arg Asn Lys Leu Leu Leu Val Ala Ser Val Ile Gln
                20                  25                  30
Gly Leu Gly Leu Leu Leu Cys Phe Thr Tyr Ile Cys Leu His Phe Ser
             35                  40                  45
Ala Leu Gln Val Ser His Arg Tyr Pro Arg Ile Gln Ser Ile Lys Val
 50                  55                  60
Gln Phe Thr Glu Tyr Lys Lys Glu Lys Gly Phe Ile Leu Thr Ser Gln
 65                  70                  75                  80
Lys Glu Asp Glu Ile Met Lys Val Gln Asn Asn Ser Val Ile Ile Asn
                 85                  90                  95
Cys Asp Gly Phe Tyr Leu Ile Ser Leu Lys Gly Tyr Phe Ser Gln Glu
            100                 105                 110
Val Asn Ile Ser Leu His Tyr Gln Lys Asp Glu Glu Pro Leu Phe Gln
            115                 120                 125
Leu Lys Lys Val Arg Ser Val Asn Ser Leu Met Val Ala Ser Leu Thr
            130                 135                 140
Tyr Lys Asp Lys Val Tyr Leu Asn Val Thr Thr Asp Asn Thr Ser Leu
145                 150                 155                 160
```

-continued

Asp Asp Phe His Val Asn Gly Glu Leu Ile Leu Ile His Gln Asn
                165                 170                 175

Pro Gly Glu Phe Cys Val Leu
            180

<210> SEQ ID NO 7
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (486)..(486)
<223> OTHER INFORMATION: Any amino acid

<400> SEQUENCE: 7

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
290                 295                 300

```
Pro Phe Trp Val Leu Val Val Gly Gly Val Leu Ala Cys Tyr Ser
305                 310                 315                 320

Leu Leu Val Thr Val Ala Phe Ile Ile Phe Trp Val Arg Ser Lys Arg
            325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
            355                 360                 365

Ala Ala Tyr Arg Ser Arg Val Lys Phe Ser Arg Ser Ala Glu Pro Pro
            370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg Xaa
            485

<210> SEQ ID NO 8
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ccatggctct cccagtgact gccctactgc ttcccctagc gcttctcctg catgcagagg    60
tgaagctgca gcagtctggg gctgagctgg tgaggcctgg gtcctcagtg aagatttcct   120
gcaaggcttc tggctatgca ttcagtagct actggatgaa ctgggtgaag cagaggcctg   180
gacagggtct tgagtggatt ggacagattt atcctggaga tggtgatact aactacaatg   240
gaaagttcaa gggtcaagcc acactgactg cagacaaatc ctccagcaca gcctacatgc   300
agctcagcgg cctaacatct gaggactctg cggtctattt ctgtgcaaga agaccattag   360
ttcggtagta gatttctact ttgactactg gggccaagga ccacggtc accgtctcct    420 caggtggagg tggatcaggt ggaggtggat ctggtggagg tggatctgac attgagctca   480
cccagtctcc aaaattcatg tccacatcag taggagacag ggtcagcgtc acctgcaagg   540
ccagtcagaa tgtgggtact aatgtagcct ggtatcaaca gaaaccagga caatctccta   600
aaccactgat ttactcggca acctaccgga acagtggagt ccctgatcgc ttcacaggca   660
gtggatctgg gacagatttc actctcacca tcactaacgt gcagtctaaa gacttggcag   720
actatttctg tcaacaatat aacaggtatc cgtacacgtc cggaggggggg accaagctgg   780 agatcaaacg ggcggccgca attgaagtta tgtatcctcc tccttaccta gacaatgaga   840
agagcaatgg aaccattatc catgtgaaag ggaaacacct ttgtccaagt cccctatttc   900
ccggaccttc taagcccttt tgggtgctgg tggtggttgg tggagtcctg gcttgctata   960
```

```
gcttgctagt aacagtggcc tttattattt tctgggtgag gagtaagagg agcaggctcc    1020
tgcacagtga ctacatgaac atgactcccc gccgccccgg gcccacccgc aagcattacc    1080
agccctatgc cccaccacgc gacttcgcag cctatcgctc agagtgaag ttcagcagga    1140 gcgcagagcc ccccgcgtac cagcagggcc agaaccagct ctataacgag ctcaatctag    1200
gacgaagaga ggagtacgat gttttggaca agagacgtgg ccgggaccct gagatggggg    1260
gaaagccgag aaggaagaac cctcaggaag gcctgtacaa tgaactgcag aaagataaga    1320
tggcggaggc ctacagtgag attgggatga aggcgagcg ccggagggc aagggcacg    1380 atggccttta ccagggtctc agtacagcca ccaaggacac ctacgacgcc cttcacatgc    1440
aggccctgcc ccctcgcg                                                  1458
```

<210> SEQ ID NO 9
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ala Leu Pro Val Thr Ala Leu Leu Leu Pro Leu Ala Leu Leu Leu
1               5                   10                  15

His Ala Glu Val Lys Leu Gln Glu Ser Gly Gly Gly Phe Val Lys Pro
            20                  25                  30

Gly Gly Ser Leu Lys Val Ser Cys Ala Ala Ser Gly Phe Thr Phe Ser
        35                  40                  45

Ser Tyr Ala Met Ser Trp Val Arg Leu Ser Pro Glu Met Arg Leu Glu
    50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Thr
                85                  90                  95

Leu His Leu Gln Met Gly Ser Leu Arg Ser Gly Asp Thr Ala Met Tyr
            100                 105                 110

Tyr Cys Ala Arg Gln Gly Phe Gly Asn Tyr Gly Asp Tyr Tyr Ala Met
        115                 120                 125

Asp Tyr Trp Gly Gln Gly Thr Thr Val Thr Val Ser Ser Gly Gly Gly
    130                 135                 140

Gly Ser Gly Gly Gly Gly Ser Gly Gly Gly Gly Ser Asp Ile Glu Leu
145                 150                 155                 160

Thr Gln Ser Pro Ser Ser Leu Ala Val Ser Ala Gly Glu Lys Val Thr
                165                 170                 175

Met Ser Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
        195                 200                 205

Leu Ile Tyr Trp Ala Ser Thr Arg Gln Ser Gly Val Pro Asp Arg Phe
    210                 215                 220

Thr Gly Ser Gly Ser Gly Thr Asp Phe Thr Leu Thr Ile Ser Ser Val
225                 230                 235                 240

Gln Ala Glu Asp Leu Ala Val Tyr Tyr Cys Gln Gln Ser Tyr Asn Leu
                245                 250                 255

Leu Thr Phe Gly Pro Gly Thr Lys Leu Glu Ile Lys Arg Ala Ala Ala
            260                 265                 270
```

Ile Glu Val Met Tyr Pro Pro Tyr Leu Asp Asn Glu Lys Ser Asn
    275                 280                 285

Gly Thr Ile Ile His Val Lys Gly Lys His Leu Cys Pro Ser Pro Leu
290                 295                 300

Phe Pro Gly Pro Ser Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Val Lys Phe Ser
370                 375                 380

Arg Ser Ala Glu Pro Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 10
<211> LENGTH: 1475
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ccatggctct cccagtgact gccctactgc ttcccctagc gcttctcctg catgcagagg    60
tgaagctgca ggagtcaggg ggaggcttcg tgaagcctgg agggtccctc aaagtctcct   120
gtgcagcctc tggattcact ttcagtagct atgccatgtc ctgggttcgc ctgagtccgg   180
agatgaggct ggagtgggtc gcaaccatta gcagtgctgg tggttacatc ttctattctg   240
acagtgtgca gggacgattc accatttcca gagacaatgc caagaacacc ctgcacctgc   300
aaatgggcag tctgaggtct ggggacacgg ccatgtatta ctgtgcaagg cagggatttg   360
gtaactacgg tgattactat gctatggact actggggcca aggaccacgg tcaccgtctc   420
cctcaggtgg aggtggatca ggtggaggtg gatctggtgg aggtggatct gacattgagc   480
tcacccagtc tccatcctcc ctggctgtgt cagcaggaga aaggtcact atgagctgca   540 aatccagtca gagtctgctc aacagtagaa cccgaaagaa ccagttggct tggtaccagc   600
aaaaaccagg acagtctcct gaactgctga tctactgggc atccactagg caatctggag   660
tccctgatcg cttcacaggc agtggatctg ggacagattt cactctcacc atcagcagtg   720
tgcaggctga agacctggca gtttattact gccagcaatc ttataatcta ctcacgttcg   780

```
gtcctgggac caagctggag atcaaacggg cggccgcaat tgaagttatg tatcctcctc    840
cttacctaga caatgagaag agcaatgaaa ccattatcca tgtgaaaggg aaacaccttt    900
gtccaagtcc cctatttccc ggaccttcta agccctttg ggtgctggtg gtggttggtg     960
gagtcctggc ttgctatagc ttgctagtaa cagtggcctt tattatttc tgggtgagga   1020 gtaagaggag caggctcctg cacagtgact acatgaacat gactccccgc cgccccgggc  1080
ccacccgcaa gcattaccag ccctatgccc caccacgcga cttcgcagcc tatcgctcca  1140
gagtgaagtt cagcaggagc gcagagcccc ccgcgtacca gcagggccag aaccagctct  1200
ataacgagct caatctagga cgaagagagg agtacgatgt tttggacaag agacgtggcc  1260
gggaccctga gatgggggga aagccgagaa ggaagaaccc tcaggaaggc ctgtacaatg  1320
aactgcagaa agataagatg gcggaggcct acagtgagat tgggatgaaa ggcgagcgcc  1380
ggaggggcaa ggggcacgat ggcctttacc agggtctcag tacagccacc aaggacacct  1440
acgacgccct tcacatgcag gccctgcccc ctcgc                               1475
```

<210> SEQ ID NO 11
<211> LENGTH: 250
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser Gly Gly Gly Ser Gly Gly Gly Gly Ser
        115                 120                 125

Gly Gly Gly Gly Ser Asp Ile Val Met Thr Gln Ser Pro Ala Thr Leu
    130                 135                 140

Ser Val Thr Pro Gly Asp Arg Val Ser Leu Ser Cys Arg Ala Ser Gln
145                 150                 155                 160

Thr Ile Ser Asp Tyr Leu His Trp Tyr Gln Gln Lys Ser His Glu Ser
                165                 170                 175

Pro Arg Leu Leu Ile Lys Phe Ala Ser Gln Ser Ile Ser Gly Ile Pro
            180                 185                 190

Ser Arg Phe Ser Gly Ser Gly Ser Gly Ser Asp Phe Thr Leu Ser Ile
        195                 200                 205

Asn Ser Val Glu Pro Glu Asp Val Gly Val Tyr Tyr Cys Gln Asn Gly
    210                 215                 220

His Gly Phe Pro Arg Thr Phe Gly Gly Gly Thr Lys Leu Glu Ile Lys
```

```
225                 230                 235                 240

Glu Gln Lys Leu Ile Ser Glu Glu Asp Leu
                245                 250

<210> SEQ ID NO 12
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Glu Ile Val Leu Thr Gln Ser Pro Ala Thr Leu Ser Leu Ser Pro Gly
    130                 135                 140

Glu Arg Ala Thr Leu Ser Cys Arg Ala Ser Gln Ser Val Ser Ser Tyr
145                 150                 155                 160

Leu Ala Trp Tyr Gln Gln Lys Pro Gly Gln Ala Pro Arg Leu Leu Ile
                165                 170                 175

Tyr Asp Ala Ser Asn Arg Ala Thr Gly Ile Pro Ala Arg Phe Ser Gly
            180                 185                 190

Ser Gly Ser Gly Thr Asp Phe Thr Leu Thr Ile Ser Ser Leu Glu Pro
        195                 200                 205

Glu Asp Phe Ala Val Tyr Tyr Cys Gln Gln Ser Ser Asn Trp Pro Arg
    210                 215                 220

Thr Phe Gly Gln Gly Thr Lys Val Glu Ile Lys
225                 230                 235

<210> SEQ ID NO 13
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Thr Asp Thr Leu Leu Leu Trp Val Leu Leu Leu Trp Val Pro
1               5                   10                  15

Gly Ser Thr Gly Asp Met Gly Leu Gly Leu Gln Trp Val Phe Phe Val
            20                  25                  30

Ala Leu Leu Lys Gly Val His Cys Glu Val Arg Leu Leu Glu Ser Gly
```

```
            35                  40                  45
Gly Gly Leu Val Lys Pro Glu Gly Ser Leu Lys Leu Ser Cys Val Ala
 50                  55                  60

Ser Gly Phe Thr Phe Ser Asp Tyr Phe Met Ser Trp Val Arg Gln Ala
 65                  70                  75                  80

Pro Gly Lys Gly Leu Glu Trp Val Ala His Ile Tyr Thr Lys Ser Tyr
                 85                  90                  95

Asn Tyr Ala Thr Tyr Tyr Ser Gly Ser Val Lys Gly Arg Phe Thr Ile
            100                 105                 110

Ser Arg Asp Asp Ser Arg Ser Met Val Tyr Leu Gln Met Asn Asn Leu
        115                 120                 125

Arg Thr Glu Asp Thr Ala Thr Tyr Tyr Cys Thr Arg Asp Gly Ser Gly
130                 135                 140

Tyr Pro Ser Leu Asp Phe Trp Gly Gln Gly Thr Gln Val Thr Val Ser
145                 150                 155                 160

Ser Ala Thr Thr Thr Ala Pro Ser Val Tyr Pro Leu Ala Pro Ala Cys
                165                 170                 175

Asp Ser Thr Thr Lys Ser Gly Gly Gly Ser Gly Gly Gly Gly Gly Ser
            180                 185                 190

Gly Gly Gly Gly Ser Tyr Glu Leu Thr Gln Pro Ser Ala Ser Val
        195                 200                 205

Asn Val Gly Glu Thr Val Lys Ile Thr Cys Ser Gly Asp Gln Leu Pro
210                 215                 220

Lys Tyr Phe Ala Asp Gln Phe His Gln Arg Ser Asp Gln Thr Ile Leu
225                 230                 235                 240

Gln Val Ile Tyr Asp Asp Asn Lys Arg Pro Ser Gly Ile Pro Glu Arg
                245                 250                 255

Ile Ser Gly Ser Ser Ser Gly Thr Thr Ala Thr Leu Thr Ile Arg Asp
            260                 265                 270

Val Arg Ala Glu Asp Glu Gly Asp Tyr Tyr Cys Phe Ser Gly Tyr Val
        275                 280                 285

Asp Ser Asp Ser Lys Leu Tyr Val Phe Gly Ser Gly Thr Gln Leu Thr
290                 295                 300

Val Leu Gly Gly Pro Lys Ser Ser Pro Lys Val Thr Val Phe Pro Pro
305                 310                 315                 320

Ser Pro Glu Glu Leu Arg Thr Asn Lys Ala Thr Leu Val Cys Leu Val
                325                 330                 335

Asn Asp Phe Tyr Pro Gly Ser Ala Thr Val Thr Trp Lys Ala Asn Gly
            340                 345                 350

Ala Thr Ile Asn Asp Gly Val Lys Thr Thr Lys Pro Ser Lys Gln Gly
        355                 360                 365

Gln Asn Tyr Met Thr Ser Ser Tyr Leu Ser Leu Thr Ala Asp Gln Trp
370                 375                 380

Lys Ser His Asn Arg Val Ser Cys Gln Val Thr His Glu Gly Glu Thr
385                 390                 395                 400

Val Glu Lys Ser Leu Ser Pro Ala Glu Cys Leu Glu Gln Lys Leu Ile
                405                 410                 415

Ser Glu Glu Asp Leu
            420

<210> SEQ ID NO 14
<211> LENGTH: 1274
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 14

| | | | | | |
|---|---|---|---|---|---|
| ccatggagac | agacacactc | ctgctatggg | tactgctgct | ctgggttcca | ggttccactg | 60 |
| gtgacatggg | attgggactg | cagtgggttt | tctttgttgc | tcttttaaaa | ggtgtccact | 120 |
| gtgaggtgcg | gcttctggag | tctggtggag | gattagtgaa | gcctgagggg | tcactgaaac | 180 |
| tctcctgtgt | ggcctctgga | ttcaccttca | gtgactattt | catgagctgg | gtccgccagg | 240 |
| ctccagggaa | ggggctggag | tgggttgctc | acatatacac | gaaaagttat | aattatgcaa | 300 |
| cttattactc | gggttcggtg | aaaggcagat | tcaccatctc | cagagatgat | tcccgaagca | 360 |
| tggtctacct | gcaaatgaac | aacctgagaa | ctgaggacac | ggccacttat | tactgtacaa | 420 |
| gagatggaag | cggatatccc | tctctggatt | tctggggtca | agggacccaa | gtcactgtct | 480 |
| cctcagccac | aacaacagcc | ccatctgtct | atcccttggc | ccctgcctgt | gacagcacaa | 540 |
| ccaaatcggg | tggaggtgga | tcaggtggag | gtggatctgg | tggaggtgga | tcttatgagc | 600 |
| tgactcagcc | accttcagca | tcagtcaatg | taggagagac | tgtcaaaatc | acctgctctg | 660 |
| gggaccaatt | gccgaaatat | tttgcagatt | ggtttcatca | aggtcagac | cagaccattt | 720 |
| tgcaagtgat | atatgatgat | aataagcgcc | cctcggggat | ccctgaaaga | atctctgggt | 780 |
| ccagctcagg | gacaacagcc | accttgacca | tcagagatgt | ccgggctgag | gatgaaggtg | 840 |
| actattactg | tttctcagga | tatgttgata | gtgatagcaa | attgtatgtt | tttggcagcg | 900 |
| gaacccagct | caccgtccta | ggtggaccca | agtcttctcc | caaagtcaca | gtgtttccac | 960 |
| cttcacctga | ggagctccgg | acaaacaaag | ccacactggt | gtgtctggtt | aatgacttct | 1020 |
| acccgggttc | tgcaacagtg | acctggaagg | caaatgagc | aactatcaat | gatggggtga | 1080 |
| agactacaaa | gccttccaaa | cagggccaaa | actacatgac | cagcagctac | ctaagtttga | 1140 |
| cagcagacca | gtggaaatct | cacaacaggg | tttcctgcca | agttacccat | gaaggggaaa | 1200 |
| ctgtggagaa | gagtttgtcc | cctgcagaat | gtctcgaaca | aaaactcatc | tcagaagagg | 1260 |
| atctgtaact | cgag | | | | | 1274 |

<210> SEQ ID NO 15
<211> LENGTH: 21
<212> TYPE: PRT
<213> ORGANISM: Homo sapiens

<400> SEQUENCE: 15

Met Glu Thr Asp Thr Leu Leu Leu Trp Val Leu Leu Leu Trp Val Pro
1               5                   10                  15
Gly Ser Thr Gly Asp
            20

<210> SEQ ID NO 16
<211> LENGTH: 21
<212> TYPE: PRT
<213> ORGANISM: Mus sp.

<400> SEQUENCE: 16

Met Glu Thr Asp Thr Leu Leu Leu Trp Val Leu Leu Leu Trp Val Pro
1               5                   10                  15
Gly Ser Thr Gly Asp
            20

```
<210> SEQ ID NO 17
<211> LENGTH: 21
<212> TYPE: PRT
<213> ORGANISM: Unknown
<220> FEATURE:
<223> OTHER INFORMATION: Description of Unknown:
      CDS leader peptide

<400> SEQUENCE: 17

Met Ala Leu Pro Val Thr Ala Leu Leu Leu Pro Leu Ala Leu Leu Leu
1               5                   10                  15

His Ala Ala Arg Pro
            20

<210> SEQ ID NO 18
<211> LENGTH: 824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ccatggagac agacacactc ctgctatggg tactgctgct ctgggttcca ggttccactg      60
gtgacgaggt gcagctggtg gagtccgggg gagacttagt gaagcctgga gggtccctga     120
aactctcctg tgcagcctct ggattcactt tcagtggcta tggcatgtct tgggttcgcc     180
agactccaga caagaggctg gagtgggtcg caaccattac tagtggtggt acttacacct     240
actatccaga cagtgtgaag gggcgattca ccatctccag agacaatgcc aagaacaccc     300
tgtacctgca aatagacagt ctgaagtctg aggatacagc catatatttc tgtgcaagat     360
ccctcgcggg aaatgctatg gactactggg gtcaaggaac ctcagtcacc gtctcctcag     420
gtggaggtgg atcaggtgga ggtggatctg gtggaggtgg atctgacatt gtgatgactc     480
agtctccagc caccctgtct gtgactccag gagatagagt ctctctttcc tgcagggcca     540
gccagactat tagcgactac ttacactggt atcaacaaaa atcacatgag tctccaaggc     600
ttctcatcaa atttgcttcc caatccattt ctgggatccc ctccaggttc agtggcagtg     660
gatcaggctc agatttcact ctcagtatca acagtgtgga acctgaagat gttggagtgt     720
attactgtca aaatggtcac ggcttttcct cggacgttcg gtggaggcacc aagctggaaa     780 tcaaagaaca aaaactcatc tcagaagagg atctgtaact cgag                      824

<210> SEQ ID NO 19
<211> LENGTH: 824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ccatggcctt accagtgacc gccttgctcc tgccgctggc cttgctgctc cacgccgcca      60
ggccggaggt gcagctggtg gagtccgggg gagacttagt gaagcctgga gggtccctga     120
aactctcctg tgcagcctct ggattcactt tcagtggcta tggcatgtct tgggttcgcc     180
agactccaga caagaggctg gagtgggtcg caaccattac tagtggtggt acttacacct     240
actatccaga cagtgtgaag gggcgattca ccatctccag agacaatgcc aagaacaccc     300
tgtacctgca aatagacagt ctgaagtctg aggatacagc catatatttc tgtgcaagat     360
ccctcgcggg aaatgctatg gactactggg gtcaaggaac ctcagtcacc gtctcctcag     420
```

```
gtggaggtgg atcaggtgga ggtggatctg gtggaggtgg atctgacatt gtgatgactc      480
agtctccagc cacoctgtct gtgactccag gagatagagt ctctctttcc tgcagggcca      540
gccagactat tagcgactac ttacactggt atcaacaaaa atcacatgag tctccaaggc      600
ttctcatcaa atttgcttcc caatccattt ctgggatccc ctccaggttc agtggcagtg      660
gatcaggctc agatttcact ctcagtatca acagtgtgga acctgaagat gttggagtgt      720
attactgtca aaatggtcac ggcttttcctc ggacgttcgg tggaggcacc aagctggaaa      780
tcaaagaaca aaaactcatc tcagaagagg atctgtaact cgag                       824
```

<210> SEQ ID NO 20
<211> LENGTH: 2337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atggctctcc cagtgactgc cctactgctt ccoctagcgc ttctcctgca tgcagaggtg      60
aagctgcagc agtctggggc tgagctggtg aggcctgggg cctcagtgaa gatttcctgc      120
aaggcttctg gctatgcatt cagtagctac tggatgaact gggtgaagca gaggcctgga      180
cagggtcttg agtggattgg acagatttat cctggagatg tgatactaa ctacaatgga      240 aagttcaagg gtcaagccac actgactgca gacaaatcct ccagcacagc ctacatgcag      300
ctcagcggcc taacatctga ggactctgcg gtctatttct gtgcaagaaa gaccattagt      360
tcggtagtag atttctactt tgactactgg ggccaaggga ccacggtcac cgtctcctca      420 ggtgaggtg gatcaggtgg aggtggatct ggtggaggtg gatctgacat tgagctcacc      480
cagtctccaa aattcatgtc cacatcagta ggagacaggg tcagcgtcac ctgcaaggcc      540
agtcagaatg tgggtactaa tgtagcctgg tatcaacaga accaggaca atctcctaaa      600 ccactgattt actcggcaac ctaccggaac agtggagtcc ctgatcgctt cacaggcagt      660
ggatctggga cagatttcac tctcaccatc actaacgtgc agtctaaaga cttggcagac      720
tatttctgtc aacaatataa caggtatccg tacacgtccg aggggggggac caagctggag      780 atcaaacggg cggccgcaat tgaagttatg tatcctcctc cttacctaga caatgagaag      840
agcaatggaa ccattatcca tgtgaaaggg aaacaccttt gtccaagtcc cctatttccc      900
ggaccttcta agccctttttg ggtgctggtg gtggttggtg gagtcctggc ttgctatagc      960
ttgctagtaa cagtggcctt tattattttc tgggtgagga gtaagaggag caggctcctg      1020
cacagtgact acatgaacat gactccccgc cgccccgggc ccacccgcaa gcattaccag      1080
ccctatgccc caccacgcga cttcgcagcc tatcgctcca gagtgaagtt cagcaggagc      1140
gcagagcccc ccgcgtacca gcagggccag aaccagctct ataacgagct caatctagga      1200
cgaagagagg agtacgatgt tttggacaag agacgtggcc gggaccctga gatgggggga      1260
aagccgagaa ggaagaaccc tcaggaaggc ctgtacaatg aactgcagaa agataagatg      1320
gcggaggcct acagtgagat tgggatgaaa ggcgagcgcc ggaggggcaa ggggcacgaa      1380
ggcctttacc agggtctcag tacagccacc aaggacacct cgacgccct tcacatgcag      1440 gccctgcccc ctcgcggatc tgagcaacaa aacttctcac tactcaaaca agcaggtgac      1500
gtggaggaga atcccggacc catggagaca gacacactcc tgctatgggt actgctgctc      1560
tgggttccag gttccactgg tgacgaggtg cagctggtgg agtccggggg agacttagtg      1620
```

```
aagcctggag ggtccctgaa actctcctgt gcagcctctg gattcacttt cagtggctat    1680
ggcatgtctt gggttcgcca gactccagac aagaggctgg agtgggtcgc aaccattact    1740
agtggtggta cttacaccta ctatccagac agtgtgaagg ggcgattcac catctccaga    1800
gacaatgcca agaacaccct gtacctgcaa atagacagtc tgaagtctga ggatacagcc    1860
atatatttct gtgcaagatc cctcgcggga aatgctatgg actactgggg tcaaggaacc    1920
tcagtcaccg tctcctcagg tggaggtgga tcaggtggag gtggatctgg tggaggtgga    1980
tctgacattg tgatgactca gtctccagcc accctgtctg tgactccagg agatagagtc    2040
tctcttccct gcagggccag ccagactatt agcgactact acactggtat caacaaaaa    2100 tcacatgagt ctccaaggct tctcatcaaa tttgcttccc aatccatttc tgggatcccc    2160
tccaggttca gtggcagagg atcaggctca gatttcactc tcagtatcaa cagtgtggaa    2220
cctgaagatg ttggagtgta ttactgtcaa aatggtcacg gctttcctcg gacgttcggt    2280
ggaggcacca agctggaaat caaagaacaa aaactcatct cagaagagga tctgtaa      2337
```

<210> SEQ ID NO 21
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
catggctctc ccagtgactg ccctactgct tccctagcg cttctcctgc atgcagaggt      60
gaagctgcag gagtcagggg gaggcttcgt gaagcctgga gggtccctca agtctcctg     120 tgcagcctct ggattcactt tcagtagcta tgccatgtcc tgggttcgcc tgagtccgga    180
gatgaggctg gagtgggtcg caaccattag cagtgctggt ggttacatct ctattctga    240 cagtgtgcag ggacgattca ccatttccag agacaatgcc aagaacaccc tgcacctgca    300
aatgggcagt ctgaggtctg gggacacggc catgtattac tgtgcaaggc agggatttgg    360
taactacggt gattactatg ctatggacta ctggggccaa gggaccacgg tcaccgtctc    420
ctcaggtgga ggtggatcag gtggaggtgg atctggtgga ggtggatctg acattgagct    480
cacccagtct ccatcctccc tggctgtgtc agcaggagag aaggtcacta tgagctgcaa    540
atccagtcag agtctgctca acagtagaac ccgaaagaac cagttggctt ggtaccagca    600
aaaaccagga cagtctcctg aactgctgat ctactgggca tccactaggc aatctggagt    660
ccctgatcgc ttcacaggca gtggatctgg gacagatttc actctcacca tcagcagtgt    720
gcaggctgaa gacctggcag tttattactg ccagcaatct tataatctac tgcaacaaac    780
ttctcactac tcaaacaagc aggtgacgtg gaggagaatc ccggacccat ggagacagac    840
acactcctgc tatgggtact gctgctctgg gttccaggtt ccactggtga cgaggtgcag    900
ctggtggagt ccgggggaga cttagtgaag cctgagggt ccctgaaact ctcctgtgca    960
gcctctggat tcactttcag tggctatggc atgtcttggg ttcgccagac tccagacaag    1020
aggctggagt gggtcgcaac cattactagt ggtggtactt acacctacta tccagacagt    1080 gtgaagggc gattcaccat ctccagagac aatgccaaga acaccctgta cctgcaaata    1140
gacagtctga agtctgagga tacagccata tatttctgtg caagatccct cgcgggaaat    1200
gctatggact actggggtca aggaacctca gtcaccgtct cctcaggtgg aggtggatca    1260
ggtggaggtg gatctggtgg aggtggatct gacattgtga tgactcagtc tccagccacc    1320
```

```
ctgtctgtga ctccaggaga tagagtctct ctttcctgca gggccagcca gactattagc    1380
gactacttac acaggtatca acaaaaatca catgagtctc caaggcttct catcaaattt    1440
gcttcccaat ccatttctgg gatcccctcc aggttcagtg gcagtggatc aggctcagat    1500
ttcactctca gtatcaacag tgtggaacct gaagatgttg gagtgtatta ctgtcaaaat    1560
ggtcacggct ttcctcggac gttcggtgga ggcaccaagc tggaaatcaa gaacaaaaa    1620 ctcatctcag aagaggatct gtaa                                           1644

<210> SEQ ID NO 22
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggagacag acacactcct gctatgggta ctgctgctct gggttccagg ttccactggt     60
gaccaggtgc agctggtgga gtctggggga ggcgtggtcc agcctgggag gtccctgaga    120
ctcgactgta aagcgtctgg aatcaccttc agtaactctg gcatgcactg ggtccgccag    180
gctccaggca aggggctgga gtgggtggca gttatttggt atgatggaag taaaagatac    240
tatgcagact ccgtgaaggg ccgattcacc atctccagag acaattccaa gaacacgctg    300
tttctgcaaa tgaacagcct gagagccgag gacacggctg tgtattactg tgcgacaaac    360
gacgactact ggggccaggg aaccctggtc accgtctcct caggtggagg tggatcaggt    420
ggaggtggat ctggtggagg tggatctgaa attgtgttga cacagtctcc agccaccctg    480
tctttgtctc caggggaaag agccaccctc tcctgcaggg ccagtcagag tgttagtagt    540
tacttagcct ggtaccaaca gaaacctggc caggctccca ggctcctcat ctatgatgca    600
tccaacaggg ccactggcat cccagccagg ttcagtggca gtgggtctgg gacagacttc    660
actctcacca tcagcagcct agagcctgaa gattttgcag tttattactg tcagcagagt    720
agcaactggc ctcggacgtt cggccaaggg accaaggtgg aaatcaaaga caaaaactc    780 atctcagaag aggatctgta a                                              801

<210> SEQ ID NO 23
<211> LENGTH: 2332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atggctctcc cagtgactgc cctactgctt cccctagcgc ttctcctgca tgcagaggtg     60
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtctag agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat cgagctcacc    480
```

| | |
|---|---|
| cagtctccaa aattcatgtc cacatcagta ggagacaggg tcagcgtcac ctgcaaggcc | 540 |
| agtcagaatg tgggtactaa tgtagcctgg tatcaacaga aaccaggaca atctcctaaa | 600 |
| ccactgattt actcggcaac ctaccggaac agtggagtcc ctgatcgctt cacaggcagt | 660 |
| ggatctggga cagattccac tctcaccatc actaacgtgc agtctaaaga cttggcagac | 720 |
| tatttctgtc aacaatataa caggtatccg tacacgtccg gagggggac caagctggag | 780 |
| atcaaacggg cggccgcaat tgaagttatg tatcctcctc cttacctaga caatgagaag | 840 |
| agcaatggaa ccattatcca tgtgaaaggg aaacaccttt gtcccaagtc ccctatttcc | 900 |
| cggaccttct aagccctttg ggtgctggtg gtggttggtg gagtcctggc ttgctatagc | 960 |
| cgctagtaac agtggccttt attattttct gggtgaggag taagaggagc aggctcctgc | 1020 |
| acagtgacta catgaacatg actccccgcc gccccgggcc cacccgcaag cattaccagc | 1080 |
| cctatgcccc accacgcgac ttcgcagcct atcgctccag agtgaagttc agcaggagcg | 1140 |
| cagagccccc cgcgtaccag cagggccaga accagctcta taacgagctc aatctaggac | 1200 |
| gaagagagga gtacgatgtt ttggacaaga gacgtggccg ggaccctgag atgggggaa | 1260 |
| agccgagaag gaagaaccct caggaaggcc tgtacaatga actgcagaaa gataagatgg | 1320 |
| cggaggccta cagtgagatt gggatgaaag gcgagcgccg gaggggcaag gggcacgatg | 1380 |
| gcctttacca gggtctcagt acagccacca aggacaccta cgacgccctt cacatgcagg | 1440 |
| ccctgccccc tcgcggatct ggagcaacaa acttctcact actcaaacaa gcaggtgacg | 1500 |
| tggaggagaa tcccggaccc atggagacag acacactcct gctatgggta ctgctgctct | 1560 |
| gggttccagg ttccactggt gaccaggtgc agctggtgga gtctggggga ggcgtggtcc | 1620 |
| agcctgggag gtccctgaga ctcgactgta aagcgtctgg aatcaccttc agtaactctg | 1680 |
| gcatgcactg gtccgccag gctccaggca aggggctgga gtgggtggca gttatttggt | 1740 |
| atgatggaag taaaagatac tatgcagact ccgtgaaggg ccgattcacc atctccagag | 1800 |
| acaattccaa gaacacgctg tttctgcaaa tgaacagcct gagagccgag gacacggctg | 1860 |
| tgtattactg tgcgacaaac gacgactact ggggccaggg aaccctggtc accgtctcct | 1920 |
| caggtggagg tggatcaggt ggaggtggat ctggtggagg tggatctgaa attgtgttga | 1980 |
| cacagtctcc agccaccctg tctttgtctc caggggaaag agccaccctc tcctgcaggg | 2040 |
| ccagtcagag tgttagtagt tacttagcct ggtaccaaca gaaacctggc caggctccca | 2100 |
| ggctcctcat ctatgatgca tccaacaggg ccactggcat cccagccagg ttcagtggca | 2160 |
| gtgggtctgg gacagacttc actctcacca tcagcagcct agagcctgaa gattttgcag | 2220 |
| tttattactg tcagcagagt agcaactggc ctcggacgtt cggccaaggg accaaggtgg | 2280 |
| aaatcaaaga acaaaaactc atctcagaag aggatctgta actcgaggat cc | 2332 |

<210> SEQ ID NO 24
<211> LENGTH: 1640
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | |
|---|---|
| catggctctc ccagtgactg ccctactgct tcccctagcg cttctcctgc atgcagaggt | 60 |
| gaagctgcag gagtcagggg gaggcttcgt gaagcctgga gggtccctca agtctcctg | 120 |
| tgcagcctct ggattcactt tcagtagcta tgccatgtcc tgggttcgcc tgagtccgga | 180 |

| | |
|---|---|
| gatgaggctg gagtgggtcg caaccattag cagtgctggt ggttacatct tctattctga | 240 |
| cagtgtgcag ggacgattca ccatttccag agacaatgcc aagaacaccc tgcacctgca | 300 |
| aatgggcagt ctgaggtctg ggacacggc catgtattac tgtgcaaggc agggatttgg | 360 |
| taactacggt gattactatg ctatggacta ctggggccaa gggaccacgg tcaccgtctc | 420 |
| ctcaggtgga ggtggatcag gtggaggtgg atctggtgga ggtggatctg acattgagct | 480 |
| cacccagtct ccatcctccc tggctgtgtc agcaggagag aaggtcacta tgagctgcaa | 540 |
| atccagtcag agtctgctca acagtagaac ccgaaagaac cagttggctt ggtaccagca | 600 |
| aaaaccagga cagtctcctg aactgctgat ctactgggca tccactaggc aatctggagt | 660 |
| ccctgatcgc ttcacaggca gtggatctgg gacagatttc actctcacca tcagcagtgt | 720 |
| gcaggctgaa gacctggcag tttattactg ccagcaatct tataatctac tgcaacaaac | 780 |
| ttctcactac tcaaacaagc aggtgacgtg gaggagaatc ccggacccat ggagacagac | 840 |
| acactcctgc tatgggtact gctgctctgg gttccaggtt ccactggtga ccaggtgcag | 900 |
| ctggtggagt ctggggagg cgtggtccag cctggggagg ccctgagact cgactgtaaa | 960 |
| gcgtctggaa tcaccttcag taactctggc atgcactggg tccgccaggc tccaggcaag | 1020 |
| gggctggagt gggtggcagt tatttggtat gatggaagta aaagatacta tgcagactcc | 1080 |
| gtgaagggcc gattcaccat ctccagagac aattccaaga acacgctgtt tctgcaaatg | 1140 |
| aacagcctga gagccgagga cacggctgtg tattactgtg cgacaaacga cgactactgg | 1200 |
| ggccagggaa ccctggtcac cgtctcctca ggtggaggtg gatcaggtgg aggtggatct | 1260 |
| ggtggaggtg gatctgaaat tgtgttgaca cagtctccag ccaccctgtc tttgtctcca | 1320 |
| ggggaaagag ccaccctctc ctgcagggcc agtcagagtg ttagtagtta cttagcctgg | 1380 |
| taccaacaga aacctggcca ggctcccagg ctcctcatct atgatgcatc caacagggcc | 1440 |
| actggcatcc cagccaggtt cagtggcagt gggtctggga cagacttcac tctcaccatc | 1500 |
| agcagcctag agcctgaaga ttttgcagtt tattactgtc agcagagtag caactggcct | 1560 |
| cggacgttcg gccaagggac caaggtggaa atcaaagaac aaaaactcat ctcagaagag | 1620 |
| gatctgtaac tcgaggatcc | 1640 |

<210> SEQ ID NO 25
<211> LENGTH: 1266
<212> TYPE: DNA
<213> ORGANISM: Artificial Sequence
<220> FEATURE:
<223> OTHER INFORMATION: Description of Artificial Sequence: Synthetic
 polynucleotide

<400> SEQUENCE: 25

| | |
|---|---|
| atggagacag acacactcct gctatgggta ctgctgctct gggttccagg ttccactggt | 60 |
| gacatgggat tgggactgca gtgggttttc tttgttgctc tttttaaagg tgtccactgt | 120 |
| gaggtgcggc ttctggagtc tgtggagga ttagtgaagc ctgagggtc actgaaactc | 180 |
| tcctgtgtgg cctctggatt caccttcagt gactatttca tgagctgggt ccgccaggct | 240 |
| ccagggaagg ggctggagtg ggttgctcac atatacacga aaagttataa ttatgcaact | 300 |
| tattactcgg gttcggtgaa aggcagattc accatctcca gagatgattc cgaagcatg | 360 |
| gtctacctgc aaatgaacaa cctgagaact gaggacacgg ccacttatta ctgtacaaga | 420 |
| gatggaagcg gatatccctc tctggatttc tggggtcaag ggaccccaagt cactgtctcc | 480 |
| tcagccacaa caacagcccc atctgtctat cccttggccc ctgcctgtga cagcacaacc | 540 |

-continued

```
aaatcgggtg gaggtggatc aggtggaggt ggatctggtg gaggtggatc ttatgagctg      600
actcagccac cttcagcatc agtcaatgta ggagagactg tcaaaatcac ctgctctggg      660
gaccaattgc cgaaatattt tgcagattgg tttcatcaaa ggtcagacca gaccattttg      720
caagtgatat atgatgataa taagcgcccc tcggggatcc ctgaaagaat ctctgggtcc      780
agctcaggga caacagccac cttgaccatc agagatgtcc gggctgagga tgaaggtgac      840
tattactgtt tctcaggata tgttgatagt gatagcaaat tgtatgtttt tggcagcgga      900
acccagctca ccgtcctagg tggacccaag tcttctccca aagtcacagt gtttccacct      960
tcacctgagg agctccggac aaacaaagcc acactggtgt gtctggttaa tgacttctac     1020 ccggggttctg caacagtgac ctggaaggca aatggagcaa ctatcaatga tggggtgaag     1080
actacaaagc cttccaaaca gggccaaaac tacatgacca gcagctacct aagtttgaca     1140
gcagaccagt ggaaatctca aacagggtt tcctgccaag ttacccatga aggggaaact      1200
gtggagaaga gtttgtcccc tgcagaatgt ctcgaacaaa aactcatctc agaagaggat     1260
ctgtaa                                                                1266
```

<210> SEQ ID NO 26
<211> LENGTH: 3325
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
catggctctc ccagtgactc ccctactgct accctagcg ttctcctgca tgcagaggtg       60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgc ggccaaggga ccacggtcac cgtctcctca     420
ggtggaggtg gcaggggag gtggatctgg ggaggtggat ctgacattga gctcacccag     480
tctccaaaat tcatgtccac atcagtagga cacagggtca cgtcacctg caaggccagt     540 cagaatgtgg gtactaatgt agcctggtat caacagaaac caggacaatc tcctaaacca     600
ctgatttact cggcaaccta ccggaacagt ggagtccctg agcgcttcac aggcagtgga     660
tctgggacag atttcactct caccatcact aacgtgcagt ctaaagactt ggcagactat     720
ttctgtcaac aatataacag gtagccgtac acgtccggag ggggaccaa gctggagatc      780 aaacgggcgg ccgcaattga gttcatgtac cctccgcctt acctagacaa cgagaggagc     840
aatggaacta ttattcacat aaaagagaaa catctttgtc atactcagtc atctcctaag     900
ctgttttggg cactggtcgt ggttgtggag tcctgttttg ttatggcttg ctagtgacag     960
tggctcttgt gttatctgga caaatagtag aaggaacaga ctccttcaaa gtgactacat    1020
gaacatgact ccccggaggg cagggctcac tcgaaagcct accagccct acgcccctgc     1080 cagagacttt gcagcgtacc gcccagagc aaaattcagc aggagtgcag agactgctgc     1140
caacctgcag gaccccaacc agctctacaa tgagctcaat ctaggcgaa gagaggaata    1200 tgacgtcttg gagaagaagc cggctcggga tccagagatg gcagccaaac agcagaggag     1260
```

```
caggaaccccc caggaaggcg tatacaatgc actgcagaaa gacaagatgg cagaagccta    1320
cagtgagatc ggcacaaaag gcgagaggcg gagaggcaag gggcacgatg gcctttacca    1380
gggtctcagc actgccacca aggacaccta tgatgggctg catatgcaga ccctggcccc    1440
tcgctaacag ccactcgagg atccgcccct ctccctcccc cccccctaac gttactggcc    1500
gaagccgctt ggaataaggc cggtgtgcgt ttgactatat gttatttcc accatattgc     1560 cgtcttttgg caatgtgagg gcccggaaac ctggccctgt cttcttgacg agcattccta    1620
ggggtctttc ccctctcgcc aaaggaatgc agggtctgtt gaatgtcgtg aaggaagcag    1680
ttcctctgga agcttcttga agacaaacaa cgtctgtagc gacccttgc aggcagcgga    1740 accccccacc tggcgacagg tgcctcagcg accaaaggcc acgtgtataa gatacaccag    1800
caaaggcggc acaaccccag tgccacgttg tgagttggat agttgtggaa agagtcaaat    1860
ggctctcctc aagcgtattc aacaaggggc tgaaggatgc ccagaaggta ccccattgta    1920
tgggatctga tctggggcct cggtcacatg ctttacatgt gtttagtcga ggttaaaaaa    1980
acgtctaggc cccccgaacc acggggacgt ggttttcctt tgaaaaacac gatgataata    2040
tggccacaaa ctgccatgga gacagacaca ctcctgctaa gggtactgct gctctgggtt    2100
ccaggttcca ctggagacat gggattggga ctgcagaggg ttttctttgt tgctcttta    2160 aaaggtgtcc actgtgaggt gcggcttctg gagtctggtg gaggattagt gaagcctgag    2220
gggtcactga aatctcctgt gtggcctcag gattcacctt cagagactat ttcatgagct    2280
gggtccgcca ggctccaggg aaggggctgg agtgggttgc tcacatatac acgaaaagtt    2340
ataattatgc aacttattac tcgggttcgg tgaaaggcag attcaccatc tccagagatg    2400
attcccgaag catggtctac cgcaaatgaa caacctgaga actgaggaca cggccactta    2460
ttactgtaca agagatggaa gcggatatcc ctctctggat ttctggggtc aagggaccca    2520
agtcactgtc tcctcagcca caacaacagc cccatctgtc tatcccttgg ccctgcctg     2580 tgacagcaca accaaatcgg gtggaggtgg atcaggtgga ggtggatctg gtggaggtgg    2640
atcttatgag ctgactcagc caccttcagc atcagtcaat gtaggagaga ctgtcaaaat    2700
cacctgctct ggggaccaat tgccgaaata ttttgcagat tggtttcatc aaaggtcaga    2760
ccagaccatt ttgcaagtga tatatgatga taataagcgc ccctcgggga tccctgaaag    2820
aatctctggg tccagctcag gacaacagc caccttgacc atcagagatg tccgggctga    2880
ggatgaaggt gactattact gtttctcagg atatgttgat agtgatagca aattgtatgt    2940
ttttggcagc ggaacccagc tcaccgtcct aggtggaccc aagtcttctc ccaaagtcac    3000
agtgtttcca ccttcacctg aggagctccg gacaaacaaa gccacactgg tgtgtctggt    3060
taatgacttc tacccgggtt ctgcaacagt gacctgaag gcaaatggag caactatcaa    3120
tgatggggtg aagactacaa agccttccaa acaggccaa aactacatga ccagcagcta    3180
cctaagtttg acagcagacc agtggaaatc tcaacagg gtttcctgcc aagttaccca    3240
tgaaggggaa actgtggaga agtttgtc ccctgcagaa tgtctcgaac aaaaactcat    3300
ctcagaagag gatctgtaac tggag                                         3325
```

<210> SEQ ID NO 27
<211> LENGTH: 3333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
ctctcccagt gactgcccta ctgcttcccc tagcgctact cctgcatgca gaggtgaagc      60
tgcaggagtc aggggaggc ttcgtgaagc ctggagggtc cctcaaagtc tcctgtgcag     120
cctctggatt cactttcagt agctatgcca tgtcctgggt tcgcctgagt ccggagatga     180
ggctggagtg ggtcgcaacc attagcagtg ctggtggtta catcttctat tctgacagtg     240
tgcagggacg attcaccatt tccagagaca atgccaagaa caccctgcac ctgcaaatgg     300
gcagtctgag gtctggggac agggccatgt attactgtgc aaggcaggga tttggtaact     360
acggtgatta ctatgctatg gactactggg gccaagggac cacggtcacc gtctcctcag     420
gtggaggtgg atcaggtgga ggtggatctg gtggaggtgg atctgacatt gagctcaccc     480
agtctccatc ctccctggct gtgtcagcag gagagaaggt cactatgagc tgcaaatcca     540
gtcagagtct gctcaacagt agaacccgaa agaaccagtt ggcttggtac cagcaaaaac     600
caggacagtc tcctgaactg ctgatctact gggcatccac taggcaatct ggagtccctg     660
atcgcttcac aggcagtgga tctgggacag atttcactct caccatcagc agtgtgcagg     720
ctgaagacct ggcagtttat tactgccagc aatcttataa tctactggga ccaagctgga     780
gatcaaacgg cggccgcaa ttgagttcat gtaccctccg ccttacctag acaacgagag     840
gagcaatgga actattattc acataaaaga gaaacatctt tgtcatactc agtcatctcc     900
taagctgttt tgggcactgg tcgtggttgc tggagtccag ttttgttatg gcttgctagt     960
gacagtggct ctttgtgtta tctggacaaa tagtagaagg aacagactcc ttcaaagtga    1020
ctacatgaac atgactcccc ggaggcctgg gctcactcga aagccttacc agccctacgc    1080
ccctgccaga gactttgcag cgtaccggcc cagagcaaaa ttcagcagga gtgcagagac    1140
tgctgccaac ctgcaggacc ccaaccagct ctacaatgag ctcaatctag ggcgaagaga    1200
ggaatatgac gtcttggaga agaagcggcc tcgggatcca gagatgggag caaacagca     1260
gaggaggagc aaccccagg aaggcgtata caatgcactg cagaaagaca agatggcaga    1320
agcctacagt gagatcggca caaaggcga gaggcggaga ggcaaggggc acgatggcct    1380
ttaccagggt ctcagcactg ccaccaagga cacctatgat gccctgcata tgcagaccct    1440
ggcccctcgc taacagccac tcgaggatcc gcccctctcc ctccccccc cctaacgtta     1500
ctggccgaag ccgcttggaa taaggccggt gtgcgtttgt ctatatgtta ttttccacca    1560
tattgccgtc ttttggcaat gtgagggccc ggaaacctgg ccctgtcttc ttgacgagca    1620
ttcctagggg tctttcccct ctcgccaaag gaatgcaggg tctgttgaat gtcgtgaagg    1680
aagcagttcc tctggaagct tcttgaagac aaacaacgtc tgtagcgacc ctttgcaggc    1740
agcggaaccc cccacctggc gacaggtgcc tctgcgacca aaggccacgt gtataagata    1800
cacctgcaaa ggcggcacaa ccccagtgcc acgttgtgag ttggatagtt gtggaaagag    1860
tcaaatggct ctcctcaagc gtattcaaca aggggctgaa ggatgcccag aaggtacccc    1920
attgtatggg atctgatctg gggcctcggt cacatgcttt acatgtgttt agtcgaggtt    1980
aaaaaaacgt ctaggccccc cgaaccacgg ggacgtggtt ttcctttgaa aaacacgatg    2040
ataatatggc cacaaactgc catggagaca gacacactcc tgctatgggt actgctgctc    2100
tgggttccag gttccactgg tgacatggga ttgggactgc agtgggtttt ctttgttgct    2160
cttttaaaag gtgtccactg tgaggtgcgg cttctggagt ctggtggagg attagtgaag    2220
cctgaggggt cactgaaact ctcctgtgtg gcctctggat tcaccttcag tgactatttc    2280
atgagctggg tccgccaggc tccagggaag gggctggagt gggttgctca catatacacg    2340
```

```
aaaagttata attatgcaac ttattactcg ggttcggtga aaggcagatt caccatctcc    2400
agagatgatt cccgaagcat ggtctacctg caaatgaaca acctgagaac tgaggacacg    2460
gccacttatt actgtacaag agatggaagc ggatatccct ctctggattt ctggggtcaa    2520
gggacccaag tcactgtctc ctcagccaca acaacagccc catctgtcta tcccttggcc    2580
cctgcctgtg acagcacaac caaatcgggt ggaggtggat caggtggagg tggatctggt    2640
ggaggtggat cttatgagct gactcagcca ccttcagcat cagtcaatgt aggagagact    2700
gtcaaaatca cctgctctgg ggaccaattg ccgaaatatt ttgcagattg gtttcatcaa    2760
aggtcagacc agaccatttt gcaagtgata tatgatgata ataagcgccc ctcggggatc    2820
cctgaaagaa tctctgggtc cagctcaggg acaacagcca ccttgaccat cagagatgtc    2880
cgggctgagg atgaaggtga ctattactgt ttctcaggat atgttgatag tgatagcaaa    2940
ttgtatgttt ttggcagcgg aacccagctc accgtcctag gtggacccaa gtcttctccc    3000
aaagtcacag tgtttccacc ttcacctgag gagctccgga caaacaaagc cacactggtg    3060
tgtctggtta atgacttcta cccgggttct gcaacagtga cctggaaggc aaatggagca    3120
actatcaatg atggcgtgaa gactacaaag ccttccaaac agggccaaaa ctacatgacc    3180
agcagctacc taagtttgac agcagaccag tggaaatctc acaacagggt tcctgccaa     3240 gttacccatg aaggggaaac tgtggagaag agtttgtccc ctgcagaatg tctcgaacaa    3300
aaactcatct cagaagagga tctgtaactc gag                                 3333
```

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgaggagacg gtgaccgtgg tcccttggcc ccag                                34

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aggtsmarct gcagsagtcw gg                                             22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttagatctc cagcttggtc cc                                             22

<210> SEQ ID NO 31
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 31
gacattcagc tgacccagtc tcca                                            24

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggctgcagst tcagtggcag tggrtcwggr ac                                   32

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctcattcctg ttgaagctct tgacaatggg                                      30

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atatccatgg cagacgtcca gatgatccag tctcca                               36

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atatccatgg cagacattgt gctgactcag tctcc                                35

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atatccatgg cagatgttgt gatgacccaa actcca                               36

<210> SEQ ID NO 37
<211> LENGTH: 35
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 37
atatccatgg cacaaattgt tctcacccag tctcc                               35

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atatccatgg cagacattgt gatgacacag tctcca                              36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atatccatgg cagatattgt gatgacgcag gctgca                              36

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atatccatgg cagacattgt gatgacccag tctc                                34

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcttcaacag gaatgagtgt taactcgagg tag                                 33

<210> SEQ ID NO 42
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccatggagac agacacactc ctgctatggg tactgctgct ctgggttcca ggttccactg    60
gtgacgaggt gctgcagctg gtggagtccg ggg                                 93

<210> SEQ ID NO 43
<211> LENGTH: 75
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 43
agatccacct ccaccagatc cacctccacc tgatccacct ccacctgagg agacggtgac    60
tgaggttcct tgacc                                                    75

<210> SEQ ID NO 44
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtggaggtg gatcaggtgg aggtggatct ggtggaggtg gatctgacat tgtgatgact    60
cagtctccag ccacc                                                    75

<210> SEQ ID NO 45
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctcgagttac agatcctctt ctgagatgag tttttgttgt ttgatttcca gcttggtgcc    60
tccaccgaac g                                                        71

<210> SEQ ID NO 46
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tataccatgg ccttaccagt gaccgccttg ctcctgccgc tggccttgct gctccacgcc    60
gccaggccgg aggtgcagct ggtggagtcc ggg                                93

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cacgtgccat ggatgaggat atttgctgtc tttatat                            37

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctcgagttac gtctcctcca aatgtgtatc acttt 35

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tattacacgt gttacatgag gatatttgct gtcttt 36

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tataggatcc tcgaggatgt tacgtctcct ccaaatgtgt a 41

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser
1               5

<210> SEQ ID NO 53
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Asp Leu
            20                  25                  30

Val Lys Pro Gly Gly Ser Leu Lys Leu Ser Cys Ala Ala Ser Gly Phe
        35                  40                  45

Thr Phe Ser Gly Tyr Gly Met Ser Trp Val Arg Gln Thr Pro Asp Lys
    50                  55                  60

```
Arg Leu Glu Trp Val Ala Thr Ile Thr Ser Gly Gly Thr Tyr Thr Tyr
 65                  70                  75                  80

Tyr Pro Asp Ser Val Lys Gly Arg Phe Thr Ile Ser Arg Asp Asn Ala
                 85                  90                  95

Lys Asn Thr Leu Tyr Leu Gln Ile Asp Ser Leu Lys Ser Glu Asp Thr
            100                 105                 110

Ala Ile Tyr Phe Cys Ala Arg Ser Leu Ala Gly Asn Ala Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Ser Asp Ile Val Met Thr Gln
145                 150                 155                 160

Ser Pro Ala Thr Leu Ser Val Thr Pro Gly Asp Arg Val Ser Leu Ser
                165                 170                 175

Cys Arg Ala Ser Gln Thr Ile Ser Asp Tyr Leu His Trp Tyr Gln Gln
            180                 185                 190

Lys Ser His Glu Ser Pro Arg Leu Leu Ile Lys Phe Ala Ser Gln Ser
        195                 200                 205

Ile Ser Gly Ile Pro Ser Arg Phe Ser Gly Ser Gly Ser Gly Ser Asp
210                 215                 220

Phe Thr Leu Ser Ile Asn Ser Val Glu Pro Glu Asp Val Gly Val Tyr
225                 230                 235                 240

Tyr Cys Gln Asn Gly His Gly Phe Pro Arg Thr Phe Gly Gly Gly Thr
                245                 250                 255

Lys Leu Glu Ile Lys Glu Gln Lys Leu Ile Ser Glu Glu Asp Leu
            260                 265                 270

<210> SEQ ID NO 54
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ala Leu Pro Val Thr Ala Leu Leu Leu Pro Leu Ala Leu Leu Leu
  1               5                  10                  15

His Ala Ala Arg Pro Glu Val Gln Leu Val Glu Ser Gly Gly Asp Leu
             20                  25                  30

Val Lys Pro Gly Gly Ser Leu Lys Leu Ser Cys Ala Ala Ser Gly Phe
         35                  40                  45

Thr Phe Ser Gly Tyr Gly Met Ser Trp Val Arg Gln Thr Pro Asp Lys
 50                  55                  60

Arg Leu Glu Trp Val Ala Thr Ile Thr Ser Gly Gly Thr Tyr Thr Tyr
 65                  70                  75                  80

Tyr Pro Asp Ser Val Lys Gly Arg Phe Thr Ile Ser Arg Asp Asn Ala
                 85                  90                  95

Lys Asn Thr Leu Tyr Leu Gln Ile Asp Ser Leu Lys Ser Glu Asp Thr
            100                 105                 110

Ala Ile Tyr Phe Cys Ala Arg Ser Leu Ala Gly Asn Ala Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Gly Ser Asp Ile Val Met Thr Gln
145                 150                 155                 160
```

```
Ser Pro Ala Thr Leu Ser Val Thr Pro Gly Asp Arg Val Ser Leu Ser
            165                 170                 175

Cys Arg Ala Ser Gln Thr Ile Ser Asp Tyr Leu His Trp Tyr Gln Gln
            180                 185                 190

Lys Ser His Glu Ser Pro Arg Leu Leu Ile Lys Phe Ala Ser Gln Ser
            195                 200                 205

Ile Ser Gly Ile Pro Ser Arg Phe Ser Gly Ser Gly Ser Gly Ser Asp
            210                 215                 220

Phe Thr Leu Ser Ile Asn Ser Val Glu Pro Glu Asp Val Gly Val Tyr
225                 230                 235                 240

Tyr Cys Gln Asn Gly His Gly Phe Pro Arg Thr Phe Gly Gly Gly Thr
            245                 250                 255

Lys Leu Glu Ile Lys Glu Gln Lys Leu Ile Ser Glu Glu Asp Leu
            260                 265                 270

<210> SEQ ID NO 55
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Thr Asp Thr Leu Leu Leu Trp Val Leu Leu Leu Trp Val Pro
1               5                   10                  15

Gly Ser Thr Gly Asp Gln Val Gln Leu Val Glu Ser Gly Gly Gly Val
            20                  25                  30

Val Gln Pro Gly Arg Ser Leu Arg Leu Asp Cys Lys Ala Ser Gly Ile
            35                  40                  45

Thr Phe Ser Asn Ser Gly Met His Trp Val Arg Gln Ala Pro Gly Lys
        50                  55                  60

Gly Leu Glu Trp Val Ala Val Ile Trp Tyr Asp Gly Ser Lys Arg Tyr
65                  70                  75                  80

Tyr Ala Asp Ser Val Lys Gly Arg Phe Thr Ile Ser Arg Asp Asn Ser
                85                  90                  95

Lys Asn Thr Leu Phe Leu Gln Met Asn Ser Leu Arg Ala Glu Asp Thr
            100                 105                 110

Ala Val Tyr Tyr Cys Ala Thr Asn Asp Asp Tyr Trp Gly Gln Gly Thr
            115                 120                 125

Leu Val Thr Val Ser Ser Gly Gly Gly Gly Ser Gly Gly Gly Gly Ser
        130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Gln
                165                 170                 175

Ser Val Ser Ser Tyr Leu Ala Trp Tyr Gln Gln Lys Pro Gly Gln Ala
            180                 185                 190

Pro Arg Leu Leu Ile Tyr Asp Ala Ser Asn Arg Ala Thr Gly Ile Pro
            195                 200                 205

Ala Arg Phe Ser Gly Ser Gly Ser Gly Thr Asp Phe Thr Leu Thr Ile
        210                 215                 220

Ser Ser Leu Glu Pro Glu Asp Phe Ala Val Tyr Tyr Cys Gln Gln Ser
225                 230                 235                 240

Ser Asn Trp Pro Arg Thr Phe Gly Gln Gly Thr Lys Val Glu Ile Lys
```

245                 250                 255
Glu Gln Lys Leu Ile Ser Glu Glu Asp Leu
            260                 265

<210> SEQ ID NO 56
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Glu Thr Asp Thr Leu Leu Leu Trp Val Leu Leu Leu Trp Val Pro
1               5                   10                  15

Gly Ser Thr Gly Asp Met Gly Leu Gly Leu Gln Trp Val Phe Phe Val
            20                  25                  30

Ala Leu Leu Lys Gly Val His Cys Glu Val Arg Leu Leu Glu Ser Gly
        35                  40                  45

Gly Gly Leu Val Lys Pro Gly Gly Ser Leu Lys Leu Ser Cys Val Ala
    50                  55                  60

Ser Gly Phe Thr Phe Ser Asp Tyr Phe Met Ser Trp Val Arg Gln Ala
65                  70                  75                  80

Pro Gly Lys Gly Leu Glu Trp Val Ala His Ile Tyr Thr Lys Ser Tyr
                85                  90                  95

Asn Tyr Ala Thr Tyr Tyr Ser Gly Ser Val Lys Gly Arg Phe Thr Ile
            100                 105                 110

Ser Arg Asp Asp Ser Arg Ser Met Val Tyr Leu Gln Met Asn Asn Leu
        115                 120                 125

Arg Thr Glu Asp Thr Ala Thr Tyr Tyr Cys Thr Arg Asp Gly Ser Gly
    130                 135                 140

Tyr Pro Ser Leu Asp Phe Trp Gly Gln Gly Thr Gln Val Thr Val Ser
145                 150                 155                 160

Ser Ala Thr Thr Thr Thr Ala Pro Ser Val Tyr Pro Leu Ala Pro Ala
                165                 170                 175

Cys Asp Ser Thr Thr Lys Ser Gly Gly Gly Ser Gly Gly Gly Gly
            180                 185                 190

Ser Gly Gly Gly Gly Ser Tyr Glu Leu Thr Gln Pro Pro Ser Ala Ser
        195                 200                 205

Val Asn Val Gly Glu Thr Val Lys Ile Thr Cys Ser Gly Asp Gln Leu
    210                 215                 220

Pro Lys Tyr Phe Ala Asp Trp Phe His Gln Arg Ser Asp Gln Thr Ile
225                 230                 235                 240

Leu Gln Val Ile Tyr Asp Asp Asn Lys Arg Pro Ser Gly Ile Pro Glu
                245                 250                 255

Arg Ile Ser Gly Ser Ser Ser Gly Thr Thr Ala Thr Leu Thr Ile Arg
            260                 265                 270

Asp Val Arg Ala Glu Asp Glu Gly Asp Tyr Tyr Cys Phe Ser Gly Tyr
        275                 280                 285

Val Asp Ser Asp Ser Lys Leu Tyr Val Phe Gly Ser Gly Thr Gln Leu
    290                 295                 300

Thr Val Leu Gly Gly Pro Lys Ser Ser Pro Lys Val Thr Val Phe Pro
305                 310                 315                 320

Pro Ser Pro Glu Glu Leu Arg Thr Asn Lys Ala Thr Leu Val Cys Leu
                325                 330                 335

-continued

```
Val Asn Asp Phe Tyr Pro Gly Ser Ala Thr Val Thr Trp Lys Ala Asn
            340                 345                 350

Gly Ala Thr Ile Asn Asp Gly Val Lys Thr Thr Lys Pro Ser Lys Gln
        355                 360                 365

Gly Gln Asn Tyr Met Thr Ser Ser Tyr Leu Ser Leu Thr Ala Asp Gln
        370                 375                 380

Trp Lys Ser His Asn Arg Val Ser Cys Gln Val Thr His Glu Gly Glu
385                 390                 395                 400

Thr Val Glu Lys Ser Leu Ser Pro Ala Glu Cys Leu Glu Gln Lys Leu
                405                 410                 415

Ile Ser Glu Glu Asp Leu
            420
```

COMPOSITIONS AND METHODS FOR IMMUNOTHERAPY

CROSS-REFERENCE TO RELATED APPLICATIONS

This application is a divisional of U.S. patent application Ser. No. 14/835,264, filed Aug. 25, 2015, which is a continuation of International Patent Application No. PCT/US2014/018667, filed Feb. 26, 2014 and claims priority to U.S. Provisional Application No. 61/769,543, filed Feb. 26, 2013, the contents of each of which are incorporated by reference in their entirety, and to each of which priority is claimed.

GRANT INFORMATION

This invention was made with government support under Grant Nos. CA95152, CA138738, CA059350, and CA08748 from the National Institutes of Health. The government has certain rights in the invention.

SEQUENCE LISTING

The specification further incorporates by reference the Sequence Listing submitted herewith via EFS on Oct. 1, 2018. Pursuant to 37 C.F.R. § 1.52(e)(5), the Sequence Listing text file, identified as "0727340789SL.TXT," is 74,661 bytes and was created on Oct. 1, 2018. The Sequence Listing, electronically filed herewith, does not extend beyond the scope of the specification and thus does not contain new matter.

INTRODUCTION

The present invention provides for methods and compositions for enhancing the immune response toward cancers and pathogens. It relates to immunoresponsive cells bearing antigen receptors, which can be chimeric antigen receptors (CARs), that express introduced ligands for immunomodulatory molecules. These engineered immunoresponsive cells are antigen-directed and resist immunosuppression and/or have enhanced immune-activating properties.

BACKGROUND OF THE INVENTION

The majority of adult B-cell malignancies, including acute lymphoblastic leukemia (ALL), chronic lymphocytic leukemia, and non-Hodgkin's lymphoma, are incurable despite currently a
vailable therapies. Adoptive therapy with genetically engineered autologous T cells has shown evidence of therapeutic efficacy in melanoma and indolent B cell malignancies. T cells may be modified to target tumor-associated antigens through the introduction of genes encoding artificial T-cell receptors, termed chimeric antigen receptors (CAR), specific to such antigens. Immunotherapy is a targeted therapy that has the potential to provide for the treatment of cancer.

However, malignant cells adapt to generate an immunosuppressive microenvironment to protect themselves from immune recognition and elimination. This "hostile" tumor microenvironment poses a challenge to methods of treatment involving stimulation of an immune response, such as targeted T cell therapies. Accordingly, novel therapeutic strategies for treating neoplasia are urgently required.

SUMMARY OF THE INVENTION

The present invention generally provides immunoresponsive cells (e.g., T cells, Natural Killer (NK) cells, cytotoxic T lymphocytes (CTLs), and regulatory T cells), expressing an antigen binding receptor (e.g., CAR or TCR) having immune cell activating activity and a single-chain variable fragment (scFv) that binds an antigen having immunosuppressive activity (e.g., CD47, PD-1, CTLA-4, and ligands thereof), thereby reducing or eliminating the immunosuppressive activity of the antigen.

The invention further provides immunoresponsive cells (e.g., T cells, Natural Killer (NK) cells, cytotoxic T lymphocytes (CTLs), and regulatory T cells), expressing an antigen binding receptor (e.g., CAR or TCR) having immune cell activating activity and a single-chain variable fragment (scFv) that binds an antigen having immunostimulatory or proinflammatory activity (e.g., CD28, OX-40, 4-1BB, CD40 and ligands thereof), thereby enhancing the immunostimulatory activity of the antigen.

The invention further provides immunoresponsive cells (e.g., T cells, Natural Killer (NK) cells, cytotoxic T lymphocytes (CTLs), and regulatory T cells), expressing an antigen binding receptor (e.g., CAR or TCR) having immune cell activating activity and CD40L, for example, exogenous CD40L (CD40L that has been introduced directly or indirectly into the cell (for example, via a vector of naked nucleic acid comprising a nucleic acid sequence encoding CD40L), as compared to endogenous CD40L arising in the cell itself), thereby enhancing the immunostimulatory activity of the antigen.

Accordingly, the invention provides methods of using such immunoresponsive cells for the treatment of neoplasia, infectious disease, and other pathologies.

In one aspect, the invention provides an isolated immunoresponsive cell having an antigen recognizing receptor that binds an antigen, where the binding activates the immunoreponsive cell, and a soluble single-chain variable fragment (scFv) that binds a polypeptide that has immunosuppressive activity or immunostimulatory activity.

In another aspect, the invention provides a method of treating or preventing neoplasia in a subject, the method comprising administering, to the subject, an effective amount of an immunoresponsive cell having an antigen recognizing receptor that binds a first antigen, where the binding activates the immunoreponsive cell, and a soluble single-chain variable fragment (scFv) that binds a polypeptide that has immunosuppressive activity or immunostimulatory activity, thereby treating or preventing neoplasia in the subject. In non-limiting embodiments, the antigen recognizing receptor is a CAR.

In another aspect, the invention provides a method of reducing tumor burden in a subject, the method involving administering, to the subject, an effective amount of an immunoresponsive cell having an antigen recognizing receptor that binds a first antigen, where the binding activates the immunoreponsive cell, and a soluble single-chain variable fragment (scFv) that binds a polypeptide that has immunosuppressive activity or immunostimulatory activity, thereby inducing tumor cell death in the subject. In still another aspect, the invention provides a method of lengthening survival of a subject having neoplasia, the method involving administering, to the subject, an effective amount of an immunoresponsive cell having an antigen recognizing receptor that binds a first antigen, where the binding activates the immunoreponsive cell, and a soluble single-chain variable fragment (scFv) that binds a polypeptide that has immunosuppressive activity or immunostimulatory activity, thereby lengthening survival of the subject. In non-limiting embodiments, the antigen recognizing receptor is a CAR.

In various non-limiting embodiments, the invention provides a method of increasing immune-activating cytokine production in response to a cancer cell in a subject, comprising administering, to the subject, an immunoresponsive cell having an antigen recognizing receptor that binds an antigen of the cancer cell and further expressing exogenous CD40L. In particular non-limiting embodiments, the immune-activating cytokine is selected from the group consisting of. In a particular non-limiting embodiment, the immune-activating cytokine is IL-12. In non-limiting embodiments, the antigen recognizing receptor is a CAR.

In various non-limiting embodiments, the invention provides a method of increasing immune-activating cytokine production in response to a pathogen in a subject, comprising administering, to the subject, an immunoresponsive cell having an antigen recognizing receptor that binds an antigen of the pathogen and further expressing exogenous CD40L. In particular non-limiting embodiments, the immune-activating cytokine is selected from the group consisting of. In a particular non-limiting embodiment, the immune-activating cytokine is IL-12. In non-limiting embodiments, the antigen recognizing receptor is a CAR.

In various non-limiting embodiments, the invention provides a method of increasing a $CD8^+$ cytotoxic T cell response to a cancer cell in a subject, comprising administering, to the subject, an immunoresponsive cell having an antigen recognizing receptor that binds an antigen of the cancer cell and further expressing exogenous CD40L. In non-limiting embodiments, the antigen recognizing receptor is a CAR.

In various non-limiting embodiments, the invention provides a method of increasing a $CD8^+$ cytotoxic T cell response to a pathogen in a subject, comprising administering, to the subject, an immunoresponsive cell having an antigen recognizing receptor that binds an antigen of the pathogen and further expressing exogenous CD40L. In non-limiting embodiments, the antigen recognizing receptor is a CAR.

In various non-limiting embodiments, the invention provides a method of promoting dendritic cell maturation in a subject having a cancer, comprising administering, to the subject, an immunoresponsive cell having an antigen recognizing receptor that binds an antigen of a cell of the cancer and further expressing exogenous CD40L. In non-limiting embodiments, the antigen recognizing receptor is a CAR.

In various non-limiting embodiments, the invention provides a method of promoting dendritic cell maturation in a subject having a disease caused by a pathogen, comprising administering, to the subject, an immunoresponsive cell having an antigen recognizing receptor that binds an antigen of the pathogen and further expressing exogenous CD40L. In non-limiting embodiments, the antigen recognizing receptor is a CAR.

In still another aspect, the invention provides a method of treating or preventing neoplasia in a subject, the method comprising administering, to the subject, an effective amount of an immunoresponsive cell having an antigen recognizing receptor that binds a first antigen, where the binding activates the immunoreponsive cell, and expressing exogenous CD40L, thereby treating or preventing a neoplasia in the subject. In non-limiting embodiments, the antigen recognizing receptor is a CAR.

In another aspect, the invention provides a method of reducing tumor burden in a subject, the method involving administering, to the subject, an effective amount of an immunoresponsive cell having an antigen recognizing receptor that binds a first antigen, where the binding activates the immunoreponsive cell, and expressing exogenous CD40L, thereby inducing tumor cell death in the subject. In still another aspect, the invention provides a method of lengthening survival of a subject having neoplasia, the method involving administering, to the subject, an effective amount of an immunoresponsive cell having an antigen recognizing receptor that binds a first antigen, where the binding activates the immunoreponsive cell, and expressing exogenous CD40L, thereby lengthening survival of the subject.

In yet another aspect, the invention provides a method of treating blood cancer in a subject in need thereof, the method involving administering to the subject a therapeutically effective amount of a T cell having an antigen recognizing receptor that binds CD19, where the binding activates the immunoreponsive cell, and a soluble single-chain variable fragment (scFv) that binds one or more of CD47, PD-1, CTLA-4, and ligands thereof, thereby treating blood cancer in the subject. In non-limiting embodiments, the antigen recognizing receptor is a CAR.

In yet another aspect, the invention provides a method of treating blood cancer in a subject in need thereof, the method involving administering to the subject a therapeutically effective amount of a T cell having an antigen recognizing receptor that binds CD19, where the binding activates the immunoreponsive cell, and expressing exogenous CD40L, thereby treating blood cancer in the subject. In non-limiting embodiments, the antigen recognizing receptor is a CAR.

In one aspect, the invention provides a method for producing an antigen-specific immunoresponsive cell, the method involving introducing into the immunoresponsive cell a nucleic acid sequence that encodes a single-chain variable fragment (scFv) that binds a polypeptide that has immunosuppressive activity or immunostimulatory activity, where the immunoresponsive cell has an antigen recognizing receptor that binds an antigen. In non-limiting embodiments, the antigen recognizing receptor is a CAR.

In one aspect, the invention provides a method for producing an antigen-specific immunoresponsive cell, the method involving introducing into the immunoresponsive cell a nucleic acid sequence that encodes CD40L, where the immunoresponsive cell has an antigen recognizing receptor that binds an antigen. In non-limiting embodiments, the nucleic acid sequence that encodes CD40L is operably linked to a promoter element constitutively or inducibly expressed in the immunoresponsive cell, optionally comprised in a vector. In non-limiting embodiments, the antigen recognizing receptor is a CAR. In non-limiting embodiments, the invention provides for a nucleic acid comprising sequence encoding a CAR and encoding CD40L, each optionally operably linked to a promoter element constitutively or inducibly expressed in the immunoresponsive cell, and said nucleic acid may optionally be comprised in a vector. In one aspect, the invention provides a vector having a nucleic acid sequence encoding an antigen recognizing receptor that binds an antigen, and a nucleic acid sequence encoding a soluble single-chain variable fragment (scFv) that binds a polypeptide having immunosuppressive activity or immunostimulatory activity. In non-limiting embodiments, the antigen recognizing receptor is a CAR.

In one aspect, the invention provides a vector having a nucleic acid sequence encoding an antigen recognizing receptor that binds an antigen, and a nucleic acid sequence encoding CD40L. In non-limiting embodiments, the antigen recognizing receptor is a CAR. In one specific non-limiting embodiment, the invention provides for a retroviral vector containing an anti-CD19 CAR (1928z)- and a CD40L-encoding nucleic acid.

In a related aspect, the invention provides a pharmaceutical composition containing an effective amount of an immunoresponsive cell of any aspect of the invention delineated herein in a pharmaceutically acceptable excipient. In another related aspect, the invention provides a pharmaceutical composition for the treatment of a neoplasia containing an effective amount of a tumor antigen-specific T cell of any aspect of the invention delineated herein in a pharmaceutically acceptable excipient.

In an additional aspect, the invention provides a kit for treatment of a neoplasia, pathogen infection, an autoimmune disorder, or an allogeneic transplant, the kit containing an immunoresponsive cell having an antigen recognizing receptor that binds an antigen and activates the immunoresponsive cell, and a soluble single-chain variable fragment (scFv) that binds a polypeptide that has immunosuppressive activity or immunostimulatory activity. In non-limiting embodiments, the antigen recognizing receptor is a CAR. In particular embodiments, the kit further contains written instructions for using the cell for the treatment of a subject having a neoplasia, a pathogen infection, an autoimmune disorder, or an allogeneic transplant.

In an additional aspect, the invention provides a kit for treatment of a neoplasia, pathogen infection, an autoimmune disorder, or an allogeneic transplant, the kit containing an immunoresponsive cell having an antigen recognizing receptor that binds an antigen and activates the immunoresponsive cell, and expressing exogenous CD40L. In non-limiting embodiments, the antigen recognizing receptor is a CAR. In particular embodiments, the kit further contains written instructions for using the cell for the treatment of a subject having a neoplasia, a pathogen infection, an autoimmune disorder, or an allogeneic transplant.

In an additional aspect, the invention provides a kit for treatment of a neoplasia, pathogen infection, an autoimmune disorder, or an allogeneic transplant, the kit comprising a nucleic acid encoding a CAR which recognizes an antigen of the neoplasia, pathogen, autoimmune disorder, or transplant to be treated, and a nucleic acid encoding a soluble single-chain variable fragment (scFv) that binds a polypeptide that has immunosuppressive activity or immunostimulatory activity. Optionally one or both nucleic acids may be comprised in a vector, which may be the same vector (bicistronic) or separate vectors. The nucleic acid encoding the CAR and/or the nucleic acid encoding the scFv may each be operably linked to a promoter which may be the same or different promoters. In particular embodiments, the kit further contains written instructions for using the cell for the treatment of a subject having a neoplasia, a pathogen infection, an autoimmune disorder, or an allogeneic transplant.

In an additional aspect, the invention provides a kit for treatment of a cancer, the kit comprising a nucleic acid encoding a CAR which recognizes an antigen of the cancer, and a nucleic acid encoding a soluble single-chain variable fragment (scFv) that binds a polypeptide that has immunosuppressive activity or immunostimulatory activity. Optionally one or both nucleic acids may be comprised in a vector, which may be the same vector (bicistronic) or separate vectors. The nucleic acid encoding the CAR and/or the nucleic acid encoding the scFv may each be operably linked to a promoter which may be the same or different promoters. In particular embodiments, the kit further contains written instructions for using the cell for the treatment of a subject having a cancer.

In an additional aspect, the invention provides a kit for treatment of a cancer or pathogen-mediated disorder, the kit comprising a nucleic acid encoding a CAR which recognizes an antigen of the cancer or pathogen, and a nucleic acid encoding a soluble single-chain variable fragment (scFv) that binds a polypeptide that has immunosuppressive activity or immunostimulatory activity. Optionally one or both nucleic acids may be comprised in a vector, which may be the same vector (bicistronic) or separate vectors. The nucleic acid encoding the CAR and/or the nucleic acid encoding the scFv may each be operably linked to a promoter which may be the same or different promoters. In particular embodiments, the kit further contains written instructions for using the cell for the treatment of a subject having a cancer or disorder. In an additional aspect, the invention provides a kit for treatment of a cancer or pathogen-mediated disorder, the kit comprising a nucleic acid encoding a CAR which recognizes an antigen of the cancer or pathogen, and a nucleic acid encoding CD40L. Optionally one or both nucleic acids may be comprised in a vector, which may be the same vector (bicistronic) or separate vectors. The nucleic acid encoding the CAR and/or the nucleic acid encoding CD40L may each be operably linked to a promoter which may be the same or different promoters. In particular embodiments, the kit further contains written instructions for using the cell for the treatment of a subject having a cancer or disorder.

In various embodiments of any of the aspects delineated herein, the cell is selected from the group consisting of a T cell, a Natural Killer (NK) cell, a cytotoxic T lymphocyte (CTL), a regulatory T cell, a human embryonic stem cell, and a pluripotent stem cell from which lymphoid cells may be differentiated. In various embodiments of any of the aspects delineated herein, the immunoresponsive cell is autologous.

In various embodiments of any of the aspects delineated herein, the antigen recognizing receptor is a T cell receptor (TCR) or chimeric antigen receptor (CAR). In various embodiments of any of the aspects delineated herein, the antigen recognizing receptor is exogenous or endogenous. In various embodiments of any of the aspects delineated herein, the antigen recognizing receptor is recombinantly expressed. In various embodiments of any of the aspects delineated herein, the antigen recognizing receptor is expressed from a vector. In various embodiments of any of the aspects delineated herein, the intracellular signaling domain of the antigen recognizing receptor is the CDζ-chain, CD97, CD11a-CD18, CD2, ICOS, CD27, CD154, CDS, OX40, 4-IBB, CD28 signaling domain, a portion thereof, or combinations thereof. In non-limiting embodiments, the antigen recognizing receptor is a CAR comprising at least a portion of CD28, 4-IBB, and/or CD3ζ-chain (see, e.g., Zhong et al., 2010, Molecular Ther. 18(2):413-420), together with an antigen binding portion. In non-limiting embodiments, the antigen recognizing receptor is a CAR described in Kohn et al., 2011, Molecular Ther. 19(3):432-438), optionally where the antigen binding portion is substituted with amino acid sequence that binds to another tumor or pathogen antigen. In various embodiments, the cell expresses a recombinant or an endogenous antigen receptor that is 1928z or 4H1128z.

In various embodiments of any of the aspects delineated herein, the antigen is a tumor or pathogen antigen. In various embodiments of any of the aspects delineated herein, the tumor antigen is one or more of CD19, MUC16, MUC1, CA1X, CEA, CD5, CD7, CD10, CD20, CD22, CD30, CD33, CD34, CD38, CD41, CD44, CD49f, CD56, CD74, CD133, CD138, a cytomegalovirus (CMV) infected cell antigen, EGP-2, EGP-40, EpCAM, erb-B2,3,4, FBP, Fetal acetylcholine receptor, folate receptor-α, GD2, GD3, HER-2, hTERT, IL-13R-a2, κ-light chain, KDR, LeY, L1 cell adhesion molecule, MAGE-AL Mesothelin, NKG2D ligands, NY-ESO-1, oncofetal antigen (h5T4), PSCA, PSMA, ROR1, TAG-72, VEGF-R2, or WT-1. In particular embodiments, the antigen is CD19 or MUC16. Amino acid sequences that specifically bind to said antigens are known in the art or may be prepared using methods known in the art; examples include immunoglobulins, variable regions of immunoglobulins (e.g. variable fragment ("Fv") or bivalent variable fragment ("Fab")), single chain antibodies, etc.

In various embodiments of any of the aspects delineated herein, the soluble scFv is secreted. In various embodiments of any of the aspects delineated herein, the scFv is expressed from a vector. In various embodiments of any of the aspects delineated herein, the immunosuppressive polypeptide is one or more of CD47, PD-1, CTLA-4, and ligands thereof. In various embodiments of any of the aspects delineated herein, the immunostimulatory polypeptide is one or more of CD28, OX-40, 4-1BB, and ligands thereof. In various embodiments of any of the aspects delineated herein, the soluble scFv enhances an immune response of the immunoreponsive cell.

In various embodiments of any of the aspects delineated herein, the immunoresponsive cell secretes a cytokine. In various embodiments of any of the aspects delineated herein, the cytokine is expressed from a vector. In various embodiments of any of the aspects delineated herein, the pharmaceutical composition containing an immunoresponsive cell of the invention contains a cytokine. In various embodiments of any of the aspects delineated herein, an immunoresponsive cell of the invention is administered with a cytokine. In various embodiments of any of the aspects delineated herein, the cytokine is one or more of IL-2, IL-3, IL-6, IL-11, IL7, IL12, IL15, IL21, granulocyte macrophage colony stimulating factor, alpha, beta or gamma interferon and erythropoietin.

In various embodiments of any of the aspects delineated herein, the method reduces the number of tumor cells, reduces tumor size, eradicates the tumor in the subject, reduces the tumor burden in the subject, and/or eradicates the tumor burden in the subject.

Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In various non-limiting embodiments of any of the aspects delineated herein, the neoplasia is one or more of blood cancer, B cell leukemia, multiple myeloma, lymphoblastic leukemia (ALL), chronic lymphocytic leukemia, non-Hodgkin's lymphoma, and ovarian cancer. In certain embodiments, the blood cancer is one or more of B cell leukemia, multiple myeloma, acute lymphoblastic leukemia (ALL), chronic lymphocytic leukemia, and non-Hodgkin's lymphoma. In particular embodiments, the neoplasia is B cell leukemia, the antigen is CD19, and the polypeptide that has immunosuppressive activity is one or more of CD47, PD-1, CTLA-4, and ligands thereof. In particular embodiments, the neoplasia is multiple myeloma, the antigen is CD19, and the polypeptide that has immunosuppressive activity is one or more of CD47, PD-1, CTLA-4, and ligands thereof. In particular embodiments, the neoplasia is acute lymphoblastic leukemia (ALL), the antigen is CD19, and the polypeptide that has immunosuppressive activity is one or more of CD47, PD-1, CTLA-4, and ligands thereof. In particular embodiments, the neoplasia is chronic lymphocytic leukemia, the antigen is CD19, and the polypeptide that has immunosuppressive activity is one or more of CD47, PD-1, CTLA-4, and ligands thereof. In particular embodiments, the neoplasia is non-Hodgkin's lymphoma, the antigen is CD19, and the polypeptide that has immunosuppressive activity is one or more of CD47, PD-1, CTLA-4, and ligands thereof. In particular embodiments, the neoplasia is ovarian cancer, the antigen is MUC16, and the polypeptide that has immunosuppressive activity is one or more of CD47, PD-1, CTLA-4, and ligands thereof.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g. CD4 or CD8, CD3γ/δ/ε/ζ, etc.) This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response. By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in increasing gene expression in order to generate long lived, proliferative, and anti-apoptotic T cells that robustly respond to antigen for complete and sustained eradication.

The term "antigen recognizing receptor" as used herein refers to a receptor that is capable of activating an immune cell (e.g., a T-cell) in response to antigen binding. Exemplary antigen recognizing receptors may be native or endogenous T cell receptors or chimeric antigen receptors in which a tumor antigen-binding domain is fused to an intracellular signaling domain capable of activating an immune cell (e.g., a T-cell).

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fe fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used herein, the term "single-chain variable fragment" or "scFv" is a fusion protein of the variable regions of the heavy (VH) and light chains (VL) of an immunoglobulin covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 August 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

By "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

The term "chimeric antigen receptor" or "CAR" as used herein refers to an antigen-binding domain that is fused to an intracellular signaling domain capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, this scFv is fused to a transmembrane domain and then to an intracellular signaling domain. "First-generation" CARs include those that solely provide CD3ζ signals upon antigen binding, "Second-generation" CARs include those that provide both costimulation (e.g. CD28 or CD137) and activation (CD3ζ). "Third-generation" CARs include those that provide multiple costimulation (e.g. CD28 and CD137) and activation (CD3ζ). In various embodiments, the CAR is selected to have high affinity or avidity for the antigen.

The term "immunosuppressive activity" is meant induction of signal transduction or changes in protein expression in a cell (e.g., an activated immunoresponsive cell) resulting in a decrease in an immune response. Polypeptides known to suppress or decrease an immune response via their binding include CD47, PD-1, CTLA-4, and their corresponding ligands, including SIRPa, PD-L1, PD-L2, B7-1, and B7-2. Such polypeptides are present in the tumor microenvironment and inhibit immune responses to neoplastic cells. In various embodiments, inhibiting, blocking, or antagonizing the interaction of immunosuppressive polypeptides and/or their ligands enhances the immune response of the immunoresponsive cell.

The term "immunostimulatory activity" is meant induction of signal transduction or changes in protein expression in a cell (e.g., an activated immunoresponsive cell) resulting in an increase in an immune response. Immunostimulatory activity may include pro-inflammatory activity. Polypeptides known to stimulate or increase an immune response via their binding include CD28, OX-40, 4-1BB, and their corresponding ligands, including B7-1, B7-2, OX-40L, and 4-1BBL. Such polypeptides are present in the tumor microenvironment and activate immune responses to neoplastic cells. In various embodiments, promoting, stimulating, or agonizing pro-inflammatory polypeptides and/or their ligands enhances the immune response of the immunoreponsive cell.

By "CD3ζ polypeptide" is meant a protein having at least 85, 90, 95, 96, 97, 98, 99 or 100% identity to NCBI Reference No: NP 932170 or a fragment thereof that has activating or stimulatory activity. An exemplary CD3ζ is provided below [SEQ ID NO:1].

```
  1  mkwkalftaa ilqaqlpite aqsfglldpk lcylldgilf iygviltalf lrvkfsrsad
 61  apayqqgqnq lynelnlgrr eeydvldkrr grdpemggkp qrrknpqegl ynelqkdkma
121  eayseigmkg errrgkghdg lyqglstatk dtydalhmqa lppr
```

By "CD3ζ nucleic acid molecule" is meant a polynucleotide encoding a CD3ζ polypeptide.

By "CD28 polypeptide" is meant a protein having at least 85, 90, 95, 96, 97, 98, 99 or 100% identity to NCBI Reference No: NP 006130 or a fragment thereof that has stimulatory activity. An exemplary CD28 is provided below [SEQ ID NO:2].

```
  1  mlrlllalnl fpsiqvtgnk ilvkqspmlv aydnavnlsc kysynlfsre fraslhkgld
 61  savevcvvyg nysqqlqvys ktgfncdgkl gnesvtfylq nlyvnqtdiy fckievmypp
121  pyldneksng tiihvkgkhl cpsplfpgps kpfwvlvvvg gvlacysllv tvafiifwvr
181  skrsrllhsd ymnmtprrpg ptrkhyqpya pprdfaayrs
```

By "CD28 nucleic acid molecule" is meant a polynucleotide encoding a CD28 polypeptide.

By "CD40L polypeptide" is meant a protein having at least 85, 90, 95, 96, 97, 98, 99 or 100% identity to NCBI Reference Sequence: NP 000065, GenBank Reference No. GenBank: AAH74950.1 or a fragment thereof that is a CD40 ligand, or a protein encoded by a nucleic acid PCR amplified from isolated healthy donor PBMCs using the following primers (1) 5'-CACGTGCATGATCGAAACATACAAC-CAAACTTCTCCCCGATCTGC-'3 [SEQ ID NO:3] and (2) 5'-CTCGAGGGATCCTCAGAGTTTGAGTAAGC-CAAAGGA-3' [SEQ ID NO:4](FIG. 22A).

By "CD40L nucleic acid molecule" is meant a polynucleotide encoding a CD40L polypeptide.

By "4-1BB polypeptide" is meant a protein having at least 85, 90, 95, 96, 97, 98, 2599 or 100% identity to NCBI Reference No: P41273 or NP_001552 or a fragment thereof that that acts as a tumor necrosis factor (TNF) ligand. An exemplary 4-1BB is provided below [SEQ ID NO:5].

```
  1  mgnscyniva tlllvlnfer trslqdpcsn cpagtfcdnn rnqicspcpp nsfssaggqr
 61  tcdicrqckg vfrtrkecss tsnaecdctp gfhclgagcs mceqdckqgq eltkkgckdc
121  cfgtfndqkr gicrpwtncs ldgksvlvng tkerdvvcgp spadlspgas svtppapare
181  pghspqiisf flaltstall fllffltlrf svvkrgrkkl lyifkqpfmr pvqttgeedg
241  cscrfpeeee ggcel
```

By "4-1BBL nucleic acid molecule" is meant a polynucleotide encoding a 4-1BBL polypeptide.

By "OX40L polypeptide" is meant a protein having at least 85, 90, 95, 96, 97, 98, 99 or 100% identity to NCBI Reference No: BAB18304 or NP_003317 or a fragment thereof that is a tumor necrosis factor (TNF) ligand [SEQ ID NO:6].

```
  1  mervqpleen vgnaarprfe rnklllvasv igglglllcf tyiclhfsal qvshrypriq
 61  sikvqfteyk kekgfiltsq kedeimkvqn nsviincdgf ylislkgyfs qevnislhyq
121  kdeeplfqlk kvrsvnslmv asltykdkvy lnvttdntsl ddfhvnggel ilihqnpgef
181  cvl
```

By "OX40L nucleic acid molecule" is meant a polynucleotide encoding a OX40L polypeptide.

By "1928z" is meant a protein having at least 85, 90, 95, 96, 97, 98, 99 or 100% identity to the sequence provided below, which includes a CDS leader sequence at amino acids 1-18, and is able to bind CD19 [SEQ ID NO:7].

MALPVTALLLPLALLLHAEVKLQQSGAELVRPGSSVKISCKASGYAFSSY

WMNWVKQRPGQGLEWIGQIYPGDGDTNYNGKFKGQATLTADKSSSTAYMQ

LSGLTSEDSAVYFCARKTISSVVDFYFDYWGQGTTVTVSSGGGGSGGGGS

GGGGSDIELTQSPKFMSTSVGDRVSVTCKASQNVGTNVAWYQQKPGQSPK

PLIYSATYRNSGVPDRFTGSGSGTDFTLTITNVQSKDLADYFCQQYNRYP

YTSGGGTKLEIKRAAAIEVMYPPPYLDNEKSNGTIIHVKGKHLCPSPLFP

GPSKPFWVLVVVGGVLACYSLLVTVAFIIFWVRSKRSRLLHSDYMNMTPR

RPGPTRKHYQPYAPPRDFAAYRSRVKFSRSAEPPAYQQGQNQLYNELNLG

RREEYDVLDKRRGRDPEMGGKPRRKNPQEGLYNELQKDKMAEAYSEIGMK

GERRRGKGHDGLYQGLSTATKDTYDALHMQALPPRX

An exemplary nucleic acid sequence encoding a 1928z polypeptide, including a CDS leader sequence, is provided below [SEQ ID NO:8].

```
ccatggctctcccagtgactgccctactgcttcccctagcgcttctcctg catgcagaggtgaagctgcagcagtctggggctgagctggtgaggcctgg
```

-continued

```
gtcctcagtgaagatttcctgcaaggcttctggctatgcattcagtagct
actggatgaactgggtgaagcagaggcctggacagggtcttgagtggatt
ggacagatttatcctggagatggtgatactaactacaatggaaagttcaa
gggtcaagccacactgactgcagacaaatcctccagcacagcctacatgc
agctcagcggcctaacatctgaggactctgcggtctatttctgtgcaaga
aagaccattagttcggtagtagatttctactttgactactggggccaagg
gaccacggtcaccgtctcctcaggtggaggtggatcaggtggaggtggat
ctggtggaggtggatctgacattgagctcacccagtctccaaaattcatg
tccacatcagtaggagacagggtcagcgtcacctgcaaggccagtcagaa
tgtgggtactaatgtagcctggtatcaacagaaaccaggacaatctccta
aaccactgatttactcggcaacctaccggaacagtggagtccctgatcgc
ttcacaggcagtggatctgggacagatttcactctcaccatcactaacgt
gcagtctaaagacttggcagactatttctgtcaacaatataacaggtatc
cgtacacgtccggagggggaccaagctggagatcaaacgggcggccgca
attgaagttatgtatcctcctccttacctagacaatgagaagagcaatgg
aaccattatccatgtgaaagggaaacacctttgtccaagtccctatttc
ccggaccttctaagccctttgggtgctggtggtggttggtggagtcctg
gcttgctatagcttgctagtaacagtggccttattattttctgggtgag
gagtaagaggagcaggctcctgcacagtgactacatgaacatgactcccc
gccgcccgggcccacccgcaagcattaccagccctatgccccaccacgc
gacttcgcagcctatcgctccagagtgaagttcagcaggagcgcagagcc
ccccgcgtaccagcagggccagaaccagctctataacgagctcaatctag
gacgaagagaggagtacgatgtttggacaagagacgtggccgggaccct
gagatgggggaaagccgagaaggaagaaccctcaggaaggcctgtacaa
tgaactgcagaaagataagatggcggaggcctacagtgagattgggatga
aaggcgagcgccggaggggcaaggggcacgatggcctttaccagggtctc
agtacagccaccaaggacacctacgacgcccttcacatgcaggccctgcc
ccctcgcg
```

By "4H1128z" is meant a protein having at least 85, 90, 95, 96, 97, 98, 99 or 100% identity to the sequence provided below, which includes a CDS leader sequence at amino acids 1-18, and is able to bind MUC [SEQ ID NO:9].

```
MALPVTALLLPLALLLHAEVKLQESGGGFVKPGGSLKVSCAASGFTFSSY
AMSWVRLSPEMRLEWVATISSAGGYIFYSDSVQGRFTISRDNAKNTLHLQ
MGSLRSGDTAMYYCARQGFGNYGDYYAMDYWGQGTTVTVSSGGGGSGGGG
SGGGGSDIELTQSPSSLAVSAGEKVTMSCKSSQSLLNSRTRKNQLAWYQQ
KPGQSPELLIYWASTRQSGVPDRFTGSGSGTDFTLTISSVQAEDLAVYYC
QQSYNLLTFGPGTKLEIKRAAAIEVMYPPPYLDNEKSNGTIIHVKGKHLC
PSPLFPGPSKPFWVLVVVGGVLACYSLLVTVAFIIFWVRSKRSRLLHSDY
MNMTPRRPGPTRKHYQPYAPPRDFAAYRSRVKFSRSAEPPAYQQGQNQLY
NELNLGRREEYDVLDKRRGRDPEMGGKPRRKNPQEGLYNELQKDKMAEAY
SEIGMKGERRRGKGHDGLYQGLSTATKDTYDALHMQALPPR
```

An exemplary nucleic acid sequence encoding a 4H1128z polypeptide, including a Kappa leader sequence, is provided below [SEQ ID NO:10].

```
ccatggctctcccagtgactgccctactgcttcccctagcgcttctcctg
catgcagaggtgaagctgcaggagtcaggggggaggcttcgtgaagcctgg
agggtccctcaaagtctcctgtgcagcctctggattcactttcagtagct
atgccatgtcctgggttcgcctgagtccggagatgaggctggagtgggtc
gcaaccattagcagtgctggtggttacatcttctattctgacagtgtgca
gggacgattcaccatttccagagacaatgccaagaacaccctgcacctgc
aaatgggcagtctgaggtctggggacacggccatgtattactgtgcaagg
cagggatttggtaactacggtgattactatgctatggactactggggcca
agggaccacggtcaccgtctcctcaggtggaggtggatcaggtggaggtg
gatctggtggaggtggatctgacattgagctcacccagtctccatcctcc
ctggctgtgtcagcaggagagaaggtcactatgagctgcaaatccagtca
gagtctgctcaacagtagaacccgaaagaaccagttggcttggtaccagc
aaaaaccaggacagtctcctgaactgctgatctactgggcatccactagg
caatctggagtccctgatcgcttcacaggcagtggatctgggacagattt
cactctcaccatcagcagtgtgcaggctgaagacctggcagtttattact
gccagcaatcttataatctactcacgttcggtcctgggaccaagctggag
atcaaacgggcggccgcaattgaagttatgtatcctcctccttacctaga
caatgagaagagcaatggaaccattatccatgtgaaagggaaacaccttt
gtccaagtcccctatttcccggaccttctaagccctttgggtgctggtg
gtggttggtggagtcctggcttgctatagcttgctagtaacagtggcctt
tattattttctgggtgaggagtaagaggagcaggctcctgcacagtgact
acatgaacatgactccccgccgccccgggcccacccgcaagcattaccag
ccctatgccccaccacgcgacttcgcagcctatcgctccagagtgaagtt
cagcaggagcgcagagccccccgcgtaccagcagggccagaaccagctct
ataacgagctcaatctaggacgaagagaggagtacgatgttttggacaag
agacgtggccgggaccctgagatgggggaaagccgagaaggaagaaccc
tcaggaaggcctgtacaatgaactgcagaaagataagatggcggaggcct
acagtgagattgggatgaaaggcgagcgccggaggggcaagggggcacgat
ggcctttaccagggtctcagtacagccaccaaggacacctacgacgccct
tcacatgcaggccctgccccctcgc
```

By "B6Hl2.2 scFv" is meant a protein having at least 85, 90, 95, 96, 97, 98, 99 or 100% identity to the sequence provided below and is able to bind CD47 [SEQ ID NO:11].

```
EVQLVESGGDLVKPGGSLKLSCAASGFTSGYGMSWVRQTPDKRLEWVAT
ITSGGTYTYYPDSVKGRFTISRDNAKNTLYLQIDSLKSEDTAIYFCARSL
```

```
AGNAMDYWGQGTSVTVSSGGGGSGGGGSGGGGSDIVMTQSPATLSVTPGD

RVSLSCRASQTISDYLHWYQQKSHESPRLLIKFASQSISGIPSRFSGSGS

GSDFTLSINSVEPEDVGVYYCQNGHGFPRTFGGGTKLEIKEQKLISEEDL
```

By "5C4 scFv" is meant a protein having at least 85, 90, 95, 96, 97, 98, 99 or 100% identity to the sequence provided below and is able to bind human PD-1 [SEQ ID NO:12].

```
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSGGGGSGGGGSGGGGSEIVLTQSPATLSLSPGERATLS

CRASQSVSSYLAWYQQKPGQAPRLLIYDASNRATGIPARFSGSGSGTDFT

LTISSLEPEDFAVYYCQQSSNWPRTFGQGTKVEIK
```

By "J43 scFv" is meant a protein having at least 85, 90, 95, 96, 97, 98, 99 or 100% identity to the sequence provided below, which includes a Kappa leader sequence at amino acids 1-21, and is able to bind human PD-1 [SEQ ID NO:13].

```
METDTLLLWVLLLWVPGSTGDMGLGLQWVFFVALLKGVHCEVRLLESGGG

LVKPEGSLKLSCVASGFTFSDYFMSWVRQAPGKGLEWVAHIYIKSYNYAT

YYSGSVKGRFTISRDDSRSMVYLQMNNLRTEDTATYYCTRDGSGYPSLDF

WGQGTQVTVSSATTTAPSVYPLAPACDSTTKSGGGGSGGGGSGGGGSYEL

TQPPSASVNVGETVKITCSGDQLPKYFADWFHQRSDQTILQVIYDDNKRP

SGIPERISGSSSGTTATLTIRDVRAEDEGDYYCFSGYVDSDSKLYVFGSG

TQLTVLGGPKSSPKVTVFPPSPEELRTNKATLVCLVNDFYPGSATVTWKA

NGATINDGVKTTKPSKQGQNYMTSSYLSLTADQWKSHNRVSCQVTHEGET

VEKSLSPAECLEQKLISEEDL*
```

An exemplary nucleic acid sequence encoding a J43 scFv polypeptide, including a Kappa leader sequence, is provided below [SEQ ID NO:14].

```
ccATGGAGACAGACACACTCCTGCTATGGGTACTGCTGCTCTGGGTTCCA

GGTTCCACTGGTGAcatgggattgggactgcagtgggttttctttgttgc tcttttaaaaggtgtccactgtgaggtgcggcttctggagtctggtggag gattagtgaagcctgaggggtcactgaaactctcctgtgtggcctctgga ttcaccttcagtgactatttcatgagctgggtccgccaggctccagggaa ggggctggagtgggttgctcacatatacacgaaaagttataattatgcaa cttattactcgggttcggtgaaaggcagattcaccatctccagagatgat tcccgaagcatggtctacctgcaaatgaacaacctgagaactgaggacac ggccacttattactgtacaagagatggaagcggatatccctctctggatt tctgggtcaagggaccccaagtcactgtctcctcagccacaacaacagcc ccatctgtctatcccttggcccctgcctgtgacagcacaaccaaatcggg tggaggtggatcaggtggaggtggatctggtggaggtggatctTatgagc tgactcagccaccttcagcatcagtcaatgtaggagagactgtcaaaatc acctgctctggggaccaattgccgaaatattttgcagattggtttcatca aaggtcagaccagaccatttttgcaagtgatatatgatgataatgcgcc cctcggggatccctgaaagaatctctgggtccagctcagggacaacagcc accttgaccatcagagatgtccgggctgaggatgaaggtgactattactg tttctcaggatatgttgatagtgatagcaaattgtatgtttttggcagcg gaacccagctcaccgtcctaggtggacccaagtcttctcccaaagtcaca gtgtttccaccttcacctgaggagctccggacaaacaaagccacactggt gtgtctggttaatgacttctacccgggttctgcaacagtgacctggaagg caaatggagcaactatcaatgatggggtgaagactacaaagccttccaaa cagggccaaaactacatgaccagcagctacctaagtttgacagcagacca gtggaaatctcacaacagggtttcctgccaagttacccatgaaggggaaa ctgtggagaagagtttgtccctgcagaatgtctcgaacaaaaactcata tcagaagaggatatgTAActcgag
```

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In particular, the ligand binds a receptor on another cell, allowing for cell-to-cell recognition and/or interaction.

The term "constitutive expression" as used herein refers to expression under all physiological conditions.

By "disease" is meant any condition or disorder that damages or interferes with the normal function of a cell, tissue, or organ. Examples of diseases include neoplasia or pathogen infection of cell.

By "effective amount" is meant an amount sufficient to have a therapeutic effect. In one embodiment, an "effective amount" is an amount sufficient to arrest, ameliorate, or inhibit the continued proliferation, growth, or metastasis (e.g., invasion, or migration) of a neoplasia.

By "endogenous" is meant a nucleic acid molecule or polypeptide that is normally expressed in a cell or tissue.

By "enforcing tolerance" is meant preventing the activity of self-reactive cells or immunoresponsive cells that target transplanted organs or tissues.

By "exogenous" is meant a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "increase" is meant to alter positively by at least 5%. An alteration may be by 5%, 10%, 25%, 30%, 50%, 75%, or even by 100%.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "tumor antigen-binding domain" as used herein refers to a domain capable of specifically binding a particular antigenic determinant or set of antigenic determinants present on a tumor.

The term "obtaining" as in "obtaining the agent" is intended to include purchasing, synthesizing or otherwise acquiring the agent (or indicated substance or material).

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple VH and VL domains). An exemplary linker sequence used in the invention is GGGGSGGGGSGGGGS (SEQ ID NO: 51).

By "modulate" is meant positively or negatively alter. Exemplary modulations include a 1%, 2%, 5%, 10%, 25%, 50%, 75%, or 100% change.

By "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

By "pathogen" is meant a virus, bacteria, fungi, parasite or protozoa capable of causing disease.

Exemplary viruses include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis*, Corynebacterium *diphtherias, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

By "receptor" is meant a polypeptide, or portion thereof, present on a cell membrane that selectively binds one or more ligand.

By "reduce" is meant to alter negatively by at least 5%. An alteration may be by 5%, 10%, 25%, 30%, 50%, 75%, or even by 100%.

By "recognize" is meant selectively binds a target. AT cell that recognizes a virus typically expresses a receptor that binds an antigen expressed by the virus.

By "reference" or "control" is meant a standard of comparison. For example, the level of scFv-antigen binding by a cell expressing a CAR and an scFv may be compared to the level of scFv-antigen binding in a corresponding cell expressing CAR alone.

By "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

By "signal sequence" or "leader sequence" is meant a peptide sequence (5, 10, 15, 20, 25, 30 amino acids long) present at the N-terminus of newly synthesized proteins that directs their entry to the secretory pathway. Exemplary leader sequences include the kappa leader sequence: METDTLLLWVLLLWVPGSTGD [SEQ ID NO:15] (human), METDTLLLWVLLLWVPGSTGD [SEQ ID NO:16] (mouse); and the CDS leader sequence: MALPVTALLL-PLALLLHAARP [SEQ ID NO:17].

By "soluble" is meant a polypeptide that is freely diffusible in an aqueous environment (e.g., not membrane bound).

By "specifically binds" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention.

The term "tumor antigen" as used herein refers to an antigen (e.g., a polypeptide) that is uniquely or differentially expressed on a tumor cell compared to a normal or non-IS neoplastic cell. With reference to the invention, a tumor antigen includes any polypeptide expressed by a tumor that is capable of activating or inducing an immune response via an antigen recognizing receptor (e.g., CD19, MUCI) or capable of suppressing an immune response via receptor-ligand binding (e.g., CD47, PD-L1/L2, B7.1/2).

By "virus antigen" is meant a polypeptide expressed by a virus that is capable of inducing an immune response.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

The term "subject" as used herein refers to a vertebrate, preferably a mammal, more preferably a human.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the invention are described in the following disclosure and are within the ambit of the invention.

BRIEF DESCRIPTION OF THE FIGURES

The following Detailed Description, given by way of example, but not intended to limit the invention to specific embodiments described, may be understood in conjunction with the accompanying drawings.

FIG. 2A depicts the structure of a secretable anti-CD47 scFv designed to include a kappa (κ) leader sequence to allow exportation of this protein. The variable heavy ($V_H$) and light ($V_L$) chains were linked with a serine glycine linker ($G_4S$) (SEQ ID NO: 52) and a myc-tag peptide was included to allow detection of the scFv. FIG. 2B depicts the secretable scFv was linked to the 1928z CAR construct using a P2A element as shown.

FIG. 3 depicts the B6H12.2 scFv sequence operably linked to a Kappa leader sequence. The variable heavy ($V_H$) and variable light ($V_L$) sequences of the B6H12.2 hybridoma were PCR amplified with a kappa leader sequence, a c-myc tag and joined with a serine glycine linker. The nucleic acid sequence (SEQ ID NO: 18) and amino acid translation (SEQ ID NO: 53) are shown.

FIG. 4 depicts B6H12.2 scFv sequence operably linked to a CDS leader sequence. The variable heavy ($V_H$) and variable light ($V_L$) sequences of the B6H12.2 hybridoma were PCR amplified with a CDS leader sequence, a c-myc tag and joined with a serine glycine linker. The nucleic acid sequence (SEQ ID NO: 19) and amino acid translation (SEQ ID NO: 54) are shown.

FIG. 5 depicts the nucleic acid sequence of the 1928z-2A-B6H12.2 (kappa leader) construct [SEQ ID NO:20]. The B6H12.2 scFv sequence was cloned into an SFG expression vector for expression with the CD19-targeted 1928z CAR. A P2A element was used to join the two elements, as shown.

FIG. 6 depicts the nucleic acid sequence of the 4Hll28z-2A-B6H12.2 (kappa leader) construct [SEQ ID NO:21]. The B6H12.2 scFv sequence was cloned into an SFG expression vector for expression with the MUC-CD-targeted 4Hll28z chimeric antigen receptor (CAR). A P2A element was used to join the two elements, as shown.

FIG. 7A depicts selection of two clones, clones 5 and 6, based on expression of 1928z CAR, which was comparable to control 1928z 293Glv9 cells. CAR expression was determined by flow cytometry and staining with 12dll antibody. FIG. 7B depicts an experiment where supernatant from 1928z or 1928z-2A-B6H12.2 packaging cells was incubated with CD47$^+$ tumor cells, Nalm-6 and Raji, and the tumor cells were washed and stained with anti-CD47. Tumor cells incubated in 1928z-2A-B6H12.2 supernatant had decreased anti-CD47 binding compared to incubation with 1928z supernatant. Supernatant from the B6H12.2 hybridoma cells was used as a control.

FIG. 8A depicts analysis by flow cytometry of CAR expression using the 12d11 antibody and of bound anti-CD47 scFv stained with a fluorescently tagged anti-c-myc tag antibody. FIG. 8B depicts the ability of the anti-CD47 scFv to block CD47, determined by staining T cells with anti-CD47 antibody. 1928z-2A-B6H12.2 T cells had decreased anti-CD47 binding compared to 1928z T cells. 1928z T cells incubated in B6H12.2 hybridoma supernatant were used as a control.

FIG. 9A depicts that 1928z and 1928z-2A T cells had an equivalent ratio of CD4:CD8 T cells, and equivalent expression of activation markers CD69 and CD25. 1928z T cells had increased expression of CD62L compared to 1928z-2A-B6H12.2 T cells. FIG. 9B depicts the ability of 1928z and 1928z-2A-B6H12.2 T cells to secrete cytokines, as assessed by flow cytometry following incubation with 3T3 (CD19$^-$/B7.1$^+$) aAPCs cells and golgi transport inhibitors, Golgi plug and Golgi Stop. 1928z and 1928z-2A-B6H12.2 T cells produced equivalent levels of IL-2 and IFNg following stimulation with 3T3(CD19$^+$/B7.1$^+$) cells. FIG. 9C depicts that 1928z and 1928z-2A-B6H12.2 T cells have equivalent cytolytic capacity, as determined by a standard $^{51}$Chromium release assay using Raji tumor cells.

FIGS. 10A and 10B depict the anti-tumor efficacy of 1928z-2A-B6H12.2 T cells. The in vivo anti-tumor efficacy of 1928z-2A-B6H12.2 T cells was investigated with a preclinical SCID-Beige mouse model. Mice were intravenously inoculated with 1×10$^6$ Nalm-6-FireFly luciferase$^+$ tumor cells and subsequently treated with 5.7×10$^6$ CAR$^+$ 1928 z, 1928z-2A-B6H12.2 or control ovarian cancer targeted 4H1128z-2A-B6H12.2 T cells, also inoculated intravenously. FIG. 10A depicts that mice treated with 1928z-2A-B6H12.2 T cells had enhanced survival compared to untreated, 1928z or 4H1128z-2A-B6H12.2 treated mice. FIG. 10B depicts that 1928z-2A-B6H12.2 treated mice have reduced tumor burden compared to nontreated, 1928z or 4H1128z-2A-B6H12.2 T cell treated mice, using bioluminescent imaging to monitor tumor progression.

FIG. 11 depicts the 5C4 scFv sequence operably linked to a Kappa leader sequence. The variable heavy ($V_H$) and variable light ($V_L$) sequences of the 5C4 antibody clone were designed with the kappa leader sequence, a c-myc tag and joined with a serine glycine linker. The nucleic acid sequence (SEQ ID NO: 22) and amino acid translation (SEQ ID NO: 55) are shown.

FIG. 12 depicts the nucleic acid sequence of the 1928z-2A-5C4 (kappa leader) construct [SEQ ID NO:23]. The 5C4 scFv sequence was cloned into an SFG expression vector for expression with the CD19-targeted 1928z CAR. A P2A element was used to join the two elements, as shown.

FIG. 13 depicts the nucleic acid sequence of the 4H1128z-2A-5C4 (kappa leader) construct [SEQ ID NO:24]. The 5C4 scFv was cloned into an SFG expression vector to be expressed with the MUC-CD-targeted 4H1128z CAR. A P2A element was used to join the two elements, as shown.

FIG. 18 depicts the J43 scFv sequence operably linked to a mouse kappa leader sequence. The variable heavy (VH) and variable light (VL) sequences of the J43 antibody clone was designed with the mouse kappa leader sequence, a c-myc tag and joined with a serine glycine linker. The nucleotide sequence (SEQ ID NO: 25) and amino acid translation (SEQ ID NO: 56) are shown.

FIG. 19 depicts the nucleic acid sequence of the 19m28mziRESJ43 (mouse kappa leader) construct [SEQ ID NO:26]. The J43 scFv was cloned into an SFG expression vector for expression with the CD19-targeted 19m28mz CAR. An internal ribosome entry site (IRES) element was used to join the two elements, as shown.

FIG. 20 depicts the nucleic acid sequence of the 4H11m28mziRESJ43 (mouse kappa leader) construct [SEQ ID NO:27]. The J43 scFv was cloned into an SFG expression vector for expression with the MUC-CD-targeted 4H11m28mz CAR. An internal ribosome entry site (IRES) element was used to join the two elements, as shown.

DETAILED DESCRIPTION OF THE INVENTION

Figure 1:
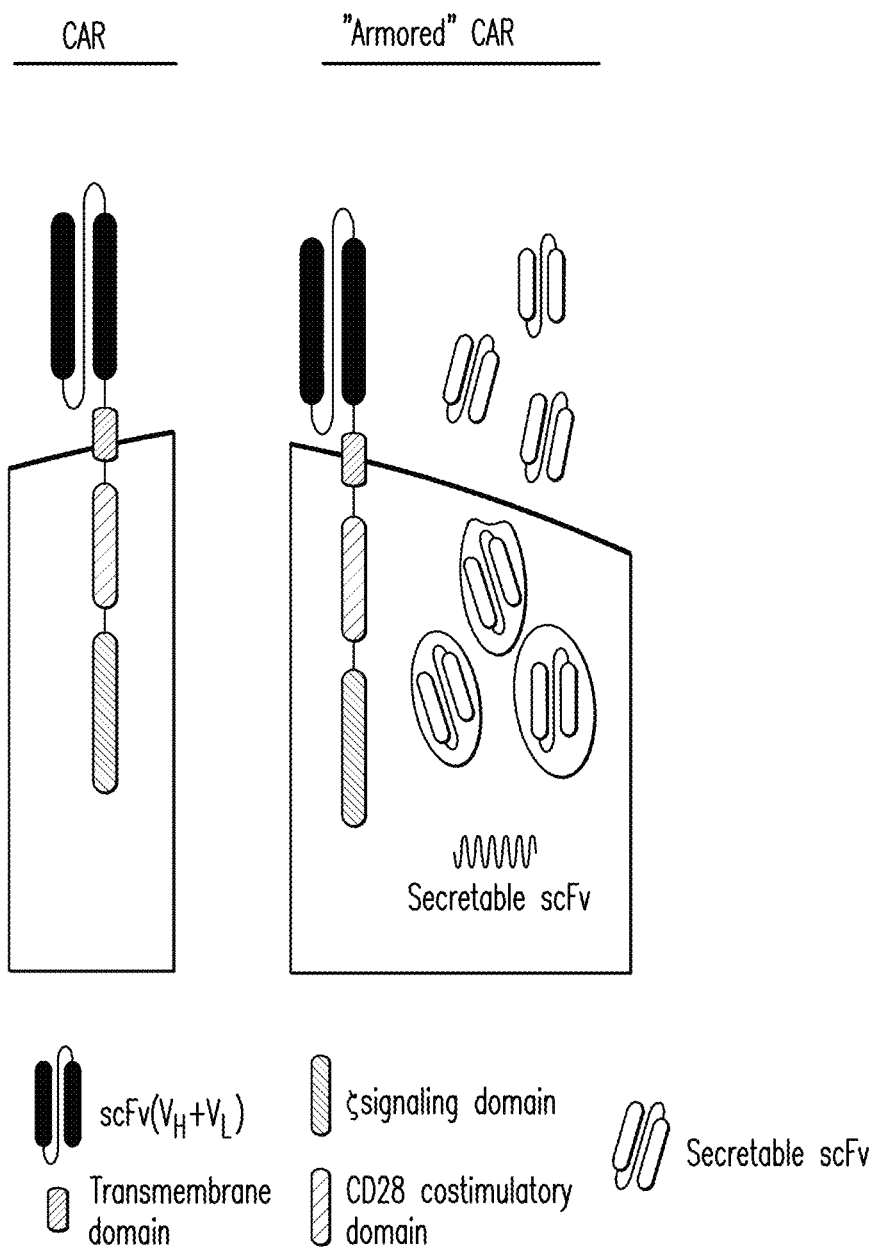
FIG. 1 depicts T cells modified to express the chimeric antigen receptor (CAR) alone or in combination with secretable scFv (e.g. αPD-1, αPD-L1, αCTLA-4, or αCD47). T cells modified to express the chimeric antigen receptor (CAR) alone are subject to suppression within the hostile tumor microenvironment. Without being bound to a particular theory, further modification of these cells to express secretable scFv to block immunosuppressive signaling has improved anti-tumor function due to their ability to modulate the tumor microenvironment and resist suppressive factors.

The present invention generally provides cells, including genetically modified immunoresponsive cells (e.g., T cells, Natural Killer (NK) cells, cytotoxic T lymphocytes (CTL) cells) expressing at least a combination of an antigen-recognizing receptor (e.g., TCR or CAR) and either (i) an scFv that binds an immunosuppressive antigen (e.g. αPD-1, αPD-L1, αCTLA-4, or αCD47)); (ii) an scFv that binds an immunostimulatory antigen (e.g. αCD28, αOX-40, αCD40 or α4-1BB) or (iii) CD40L, and methods of using such cells for the treatment of neoplasia and other pathologies where an increase in an antigen-specific immune response is desired. The invention is based, at least in part, on the discovery that scFvs that bind an immunosuppressive antigen (e.g. CD47 and PD-L1 as shown herein) are useful for activating and stimulating an immunoreactive cell. In particular, the scFvs of the invention decrease or prevent suppression of the immune response of an activated immunoreactive cell in the tumor microenvironment. Malignant cells have developed a series of mechanisms to protect themselves from immune recognition and elimination. The present approach provides immunogenicity within the tumor microenvironment for tumor eradication, and represents a significant advance over conventional adoptive T cell therapy.

Tumor Microenvironment

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Cytotoxic T-Lymphocyte Antigen 4 (CTLA-4)

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities. Without being bound to a particular theory, targeted CTLA-4 blockade through delivery of antagonistic scFvs by tumor targeted CAR modified T cells allows for reduced toxicity as well as provides a surrogate "endogenous" population of tumor targeted T cells (the CART cell population) protected from immune suppression. Pre-clinical studies (e.g., human xenograft tumor models and murine tumor models of B cell malignancies and ovarian carcinomas) can be used to evaluate the effect of scFv secretion both on the CAR modified T cell population as well as on the endogenous anti-tumor immune response. Anti-CTLA-4 scFv can be generated from the 9D9 hybridoma, which secretes mouse anti-mouse CTLA-4 monoclonal antibodies, or the 9H10 hybridoma, which secretes hamster anti-mouse CTLA-4 monoclonal antibodies.

Programmed Cell Death Protein 1 (PD-1)

PD-1 is a negative immune regulator of activated T cells upon engagement with its corresponding ligands PD-L1 and PD-L2 expressed on endogenous macrophages and dendritic cells. Upregulation of PD-L1 is one mechanism tumor cells may evade the host immune system. Again, in both preclinical and recently published clinical trials, PD-1 blockade by antagonistic antibodies induced anti-tumor responses mediated through the host endogenous immune system. Xenograft and syngeneic murine tumor models can be used to show that antagonistic anti-PD-1 scFvs secreted by tumor targeted CAR modified T cells enhance the anti-tumor efficacy of these scFv secreting CAR modified T cells.

CD47

CD47 is a membrane protein with broad tissue distribution and one which has been shown in recent preclinical models to protect a wide array of tumor cells from macrophage recognition. In these models, infusion of anti-CD47 monoclonal antibodies resulted in a decrease of established tumor progression. In other words, CD47 blockade on tumor cells exposed these tumor cells to recognition and phagocytosis by the host macrophages. Given the rather ubiquitous expression of this antigen, systemic blocking antibody infusion may potentially lead to off-target toxicity. Again, in keeping with the paradigm of targeted delivery, secretion of similarly blocking anti-CD47 scFvs delivered directly to the tumor microenvironment by CAR modified T cells induce/enhance a desired anti-tumor effect, in this case mediated by the innate rather than adaptive host immune system. Furthermore, this approach is not limited to the treatment of neoplasias, but is amenable to a wide range of applications where an increase in an antigen-specific immune response is desired, such applications include not only the treatment of neoplasias, but also for the enhancement of an immune response against a pathogen infection or an infectious disease and to reinforce immune tolerance in regulatory T cells in the context of autoimmunity or allogeneic transplantation.

CD40L

CD40 ligand (CD40L, CD154), a type II transmembrane protein belonging to the tumor necrosis factor (TNF) gene superfamily, has the potential to enhance tumor specific T-cell function. Initially identified on activated CD4+ T-cells, expression of CD40L is inducible on a vast array of immune, hematopoietic, epithelial, endothelial and smooth muscle cells. In activated T-cells, CD40L is expressed within minutes, peaking within 6 hours, and then declining over the subsequent 12-24 hours. CD40L binds to its cognate receptor CD40 which is constitutively expressed on a variety of immune and non-immune cells including B-cells, macrophages, and dendritic cells (DCs). Significantly, CD40 is also expressed on several hematologic and non-hematologic malignancies including chronic lymphocytic leukemia (CLL), acute lymphoblastic leukemia (ALL), non-Hodgkin lymphoma (NHL), Hodgkin Lymphoma, nasopharyngeal carcinoma, osteosarcoma, Ewing sarcoma, melanoma, breast, ovarian, and cervical carcinoma demonstrating potential application of CAR/CD40L T-cells to a broad array of malignancies. See references 8-17 listed in the references to Example 6, below.

Hematopoietic Cell Lineages

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The term "T cells" as used herein refers to lymphocytes that mature in the thymus and are chiefly responsible for cell-mediated immunity. T cells are involved in the adaptive immune system. The term "natural killer (NK) cells" as used herein refers to lymphocytes that are part of cell-mediated immunity and act during the innate immune response. They do not require prior activation in order to perform their cytotoxic effect on target cells. Cytotoxic T cells (CTL or killer T cells) are a subset of T lymphocytes capable of inducing the death of infected somatic or tumor cells.

Cells for Use in the Methods of the Invention

The present invention provides cells expressing a combination of an antigen-recognizing receptor that activates an immunoresponsive cell (e.g., TCR, CAR) and an scFv that binds an immunosuppressive antigen (e.g. αPD-1, αPD-L1, αCTLA-4, or αCD47), and methods of using such cells for the treatment of a disease that requires an enhanced immune response. In one approach, tumor antigen-specific T cells, NK cells, CTL cells or other immunoresponsive cells are used to express an scFv that binds an immunosuppressive antigen, for the treatment or prevention of neoplasia. For example, a T cell expressing a chimeric antigen receptor 1928z that recognizes CD19 is co-expressed in aT cell that expresses an scFv that binds CD47. Such cells are administered to a human subject in need thereof for the treatment or prevention of blood cancers (e.g. leukemias, lymphomas, and myelomas). In another approach, viral antigen-specific T cells, NK cells, CTL cells can be used for the treatment of viral diseases. For example, a chimeric co-stimulatory antigen receptor that recognizes a first CMV antigen and an scFv that binds PD-1 are co-expressed in cytotoxic T lymphocytes for the treatment of CMV.

A patient's own T cells may be genetically modified to target tumors through the introduction of genes encoding artificial T cell receptors termed chimeric antigen receptors (CARs). First generation CARs are typically composed of an antibody-derived antigen recognition domain, a single fragment length antibody (scFv), fused to a variable transmembrane domain, fused to cytoplasmic signaling domain of the T cell receptor chain. Additional inclusion of one or two co-stimulatory receptor signaling domains including CD28, 4-1BB, and OX-40 proximal to the C chain enhances CAR signaling resulting in second and third generation CARs respectively.

Tumor Antigen-Specific T Lymphocytes (and NK Cells)

Types of tumor antigen-specific human lymphocytes that can be used in the methods of the invention include, without limitation, peripheral donor lymphocytes genetically modified to express chimeric antigen receptors (CARs) (Sadelain, M., et al. 2003 *Nat Rev Cancer* 3:35-45), peripheral donor lymphocytes genetically modified to express a full-length tumor antigen-recognizing T cell receptor complex comprising the a and β heterodimer (Morgan, R. A., et al. 2006 *Science* 314:126-129), lymphocyte cultures derived from tumor infiltrating lymphocytes (TILs) in tumor biopsies (Panelli, M. C., et al. 2000 *J Immunol* 164:495-504; Panelli, M. C., et al. 2000 *J Immunol* 164:4382-4392), and selectively in vitro-expanded antigen-specific peripheral blood leukocytes employing artificial antigen-presenting cells (AAPCs) or pulsed dendritic cells (Dupont, J., et al. 2005 *Cancer Res* 65:5417-5427; Papanicolaou, G. A., et al. 2003 *Blood* 102:2498-2505). The T cells may be autologous, allogeneic, or derived in vitro from engineered progenitor or stem cells. Any suitable tumor antigen (antigenic peptide) is suitable for use in the tumor-related embodiments described herein. Sources of antigen include, but are not limited to cancer proteins. The antigen can be expressed as a peptide or as an intact protein or portion thereof. The intact protein or a portion thereof can be native or mutagenized.

Suitable antigens include prostate specific membrane antigen (PSMA) and prostate stem cell antigen (PCSA).

Viral Antigen-Specific T Lymphocytes (and NK Cells)

Suitable antigens for use in the treatment of pathogen infection or other infectious disease, for example, in an immunocompromised subject include, without limitation, viral antigens present in Cytomegalovirus (CMV), Epstein Barr Virus (EBV), Human Immunodeficiency Virus (HIV), and influenza virus.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels. The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

Accordingly, the invention generally provides an immunoresponsive cell, such as a virus specific or tumor specific T cell comprising a receptor that binds a first antigen and activates the immunoresponsive cell and a receptor that binds a second antigen and stimulates the immunoresponsive cell.

Vectors

Genetic modification of immunoresponsive cells (e.g., T cells, CTL cells, NK cells) can be accomplished by transducing a substantially homogeneous cell composition with a recombinant DNA construct. Preferably, a retroviral vector (either gamma-retroviral or lentiviral) is employed for the introduction of the DNA construct into the cell. For example, a polynucleotide encoding a receptor that binds an antigen (e.g., a tumor antigen, or a variant, or a fragment thereof), can be cloned into a retroviral vector and expression can be driven from its endogenous promoter, from the retrovirallong terminal repeat, or from a promoter specific for a target cell type of interest. Non-viral vectors may be used as well.

For initial genetic modification of the cells to provide tumor or viral antigen-specific cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to express a co-stimulatory ligand of the invention in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation. cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Polypeptides and Analogs

Also included in the invention are αCD19, CD28, CD3ζ, 4H1128z, B6H12.2 scFv, 5C4 scFv, and J43 scFv polypeptides or fragments thereof that are modified in ways that enhance their anti-neoplastic activity (e.g., a humanized monoclonal antibody) when expressed in an immunoresponsive cell. The invention provides methods for optimizing an amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, 90%, 91%, 92%, 93%, 94%, 95%, 96%, 97%, 98%, 99% or more identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., .beta. or .gamma. amino acids.

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the invention. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. Preferably, the protein analogs are relatively resistant to in vivo degradation, resulting in a more prolonged therapeutic effect upon administration. Assays for measuring functional activity include, but are not limited to, those described in the Examples below.

Co-Stimulatory Ligands

The interaction with at least one co-stimulatory ligand provides a non-antigen-specific signal important for full activation of an immune cell (e.g., T cell). Co-stimulatory ligands include, without limitation, tumor necrosis factor (TNF) ligands, cytokines (such as IL-2, IL-12, IL-15 or IL21), and immunoglobulin (Ig) superfamily ligands. Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins (extracellular C-terminus) containing a short cytoplasmic segment and a relatively long extracellular region. TNF ligands include, without limitation, nerve growth factor (NGF), CD40L (CD40L)/CD154, CD137L/4-1BBL, tumor necrosis factor alpha (TNFα), CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28.

Administration

Compositions comprising genetically modified immunoresponsive cells of the invention (e.g., T cells, NK cells, CTL cells, or their progenitors) can be provided systemically or directly to a subject for the treatment of a neoplasia, pathogen infection, or infectious disease. In one embodiment, cells of the invention are directly injected into an organ of interest (e.g., an organ affected by a neoplasia). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells will be administered, eventually reaching $1 \times 10^{10}$ or more. Genetically modified immunoresponsive cells of the invention can comprise a purified population of cells.

Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, IL-11, IL7, IL12, IL1S, IL21, as well as the other interleukins, the colony stimulating factors, such as G-, M- and GM-CSF, interferons, e.g., gamma.-interferon and erythropoietin.

Compositions of the invention include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations

Compositions of the invention comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the genetically modified immunoresponsive cells as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of genetically modified immunoresponsive cells of the invention is the quantity of cells necessary to achieve an optimal effect. The quantity of cells to be administered will vary for the subject being treated. In a one embodiment, between $10^4$ to $10^{10}$ between $10^5$ to $10^9$, or between $10^6$ and $10^8$ genetically modified immunoresponsive cells of the invention are administered to a human subject. More effective cells may be administered in even smaller numbers. In some embodiments, at least about $1 \times 10^8$, $2 \times 10^8$, $3 \times 10^8$, $4 \times 10^8$, and $5 \times 10^8$ genetically modified immunoresponsive cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Methods of Treatment

Provided herein are methods for treating neoplasia in a subject. Also contemplated herein are methods for treating a pathogen infection or other infectious disease in a subject, such as an immunocompromised human subject. The methods comprise administering a T cell, NK cell, or CTL cell of the invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount.

These factors include age, sex and weight of the subject, the condition being treated, the severity of the condition and the form and effective concentration of the antigen-binding fragment administered.

For adoptive immunotherapy using antigen-specific T cells, cell doses in the range of $10^6$-$10^{10}$ (e.g., $10^9$) are typically infused. Upon administration of the genetically modified cells into the host and subsequent differentiation, T cells are induced that are specifically directed against the specific antigen. "Induction" of T cells can include inactivation of antigen-specific T cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus.

Therapeutic Methods

The invention provides methods for increasing an immune response in a subject in need thereof. In one embodiment, the invention provides methods for treating or preventing a neoplasia in a subject. The invention provides therapies that are particularly useful for the treatment of subjects having blood cancers (e.g. leukemias, lymphomas, and myelomas) or ovarian cancer, that are not amenable to conventional therapeutic interventions. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

Human neoplasia subjects having any of the following neoplasias: glioblastoma, melanoma, neuroblastoma, adenocarcinoma, glioma, soft tissue sarcoma, and various carcinomas (including prostate and small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Accordingly, the invention provides a method of treating or preventing a neoplasia in a subject, the method comprising administering an effective amount of an immunoresponsive cell comprising a receptor that binds a tumor antigen and activates the immunoresponsive cell (e.g., TCR, CAR) and a vector encoding a single-chain variable fragment (scFv) that binds an antigen having immunosuppressive activity (e.g., CD47, PD-1, CTLA-4, and ligands thereof). In one embodiment, the neoplasia is selected from the group consisting of blood cancers (e.g. leukemias, lymphomas, and myelomas), ovarian cancer, prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In another embodiment, the tumor antigen is one or more of carbonic anhydrase IX (CA1X), carcinoembryonic antigen (CEA), CDS, CD7, CDIO, CD19, CD20, CD22, CD30, CD33, CD34, CD38, CD41, CD44, CD49f, CD56, CD74, CD133, CD138, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-α, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), or Wilms tumor protein (WT-1).

As a consequence of surface expression of a receptor that binds a tumor antigen and activates the immunoresponsive cell (e.g., TCR, CAR) and a vector encoding a single-chain variable fragment (scFv) that binds an antigen having immunosuppressive activity (e.g., CD47, PD-1, CTLA-4, and ligands thereof), adoptively transferred human Tor NK cells are endowed with augmented and selective cytolytic activity at the tumor site. Furthermore, subsequent to their localization to tumor or viral infection and their proliferation, co-stimulatory ligand-expressing T cells turn the tumor or viral infection site into a highly conductive environment for a wide range of immune cells involved in the physiological anti-tumor or antiviral response (tumor infiltrating lymphocytes, NK-, NKT-cells, dendritic cells, and macrophages).

In other embodiments, the invention provides methods for treating subjects with a pathogen infection (e.g., viral infection, bacterial infection, fungal infection, parasite infection, or protozoal infection). The invention is particularly useful for enhancing an immune response in an immunocompromised subject. Exemplary viral infections susceptible to treatment using a method of the invention include, but are not limited to, Cytomegalovirus (CMV), Epstein Barr Virus (EBV), Human Immunodeficiency Virus (HIV), and influenza virus infections.

Accordingly, the invention provides a method of treating or preventing a pathogen infection in a subject, the method comprising administering an effective amount of an immunoresponsive cell as described herein.

Kits

The invention provides kits for the treatment or prevention of a neoplasia, pathogen infection, immune disorder or allogeneic transplant. In one embodiment, the kit includes a therapeutic or prophylactic composition containing an effective amount of an immunoresponsive cell comprising an activating antigen receptor and a single-chain variable fragment (scFv) that binds an antigen having immunosuppressive activity in unit dosage form. In particular embodiments, the cells further comprise a co-stimulatory ligand. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired the immunoresponsive cell is provided together with instructions for administering the cell to a subject having or at risk of developing a neoplasia, pathogen infection, immune disorder or allogeneic transplant. The instructions will generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1. T Cells Co-Expressing a Chimeric Antigen Receptor (CAR) and an Anti-SCD47 scFv Eradicated Tumors An scFv that specifically binds human CD47 was generated and human peripheral blood T cells modified with this scFv and a CAR recognizing a tumor antigen (CD19), demonstrated in vitro anti-tumor efficacy as well as enhanced anti-tumor efficacy in a preclinical model.

Figure 7A:
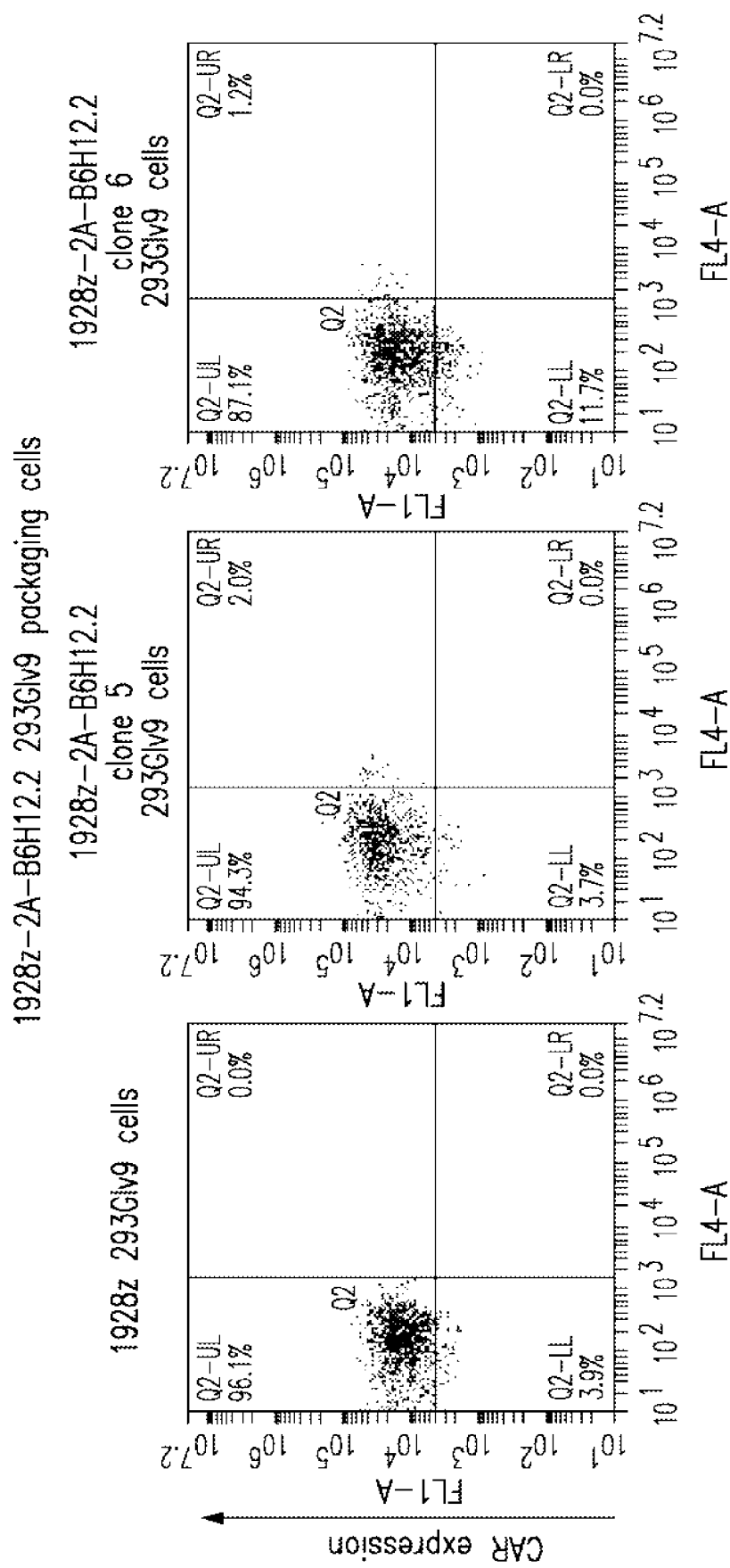
FIGS. 7A and 7B depict the generation of 1928-2A-B6H12.2 293Glv9 packaging cells. Viral packaging cells were generated using the 1928z-2A-B6H12.2 or 1928z vector.
Figure 7B:
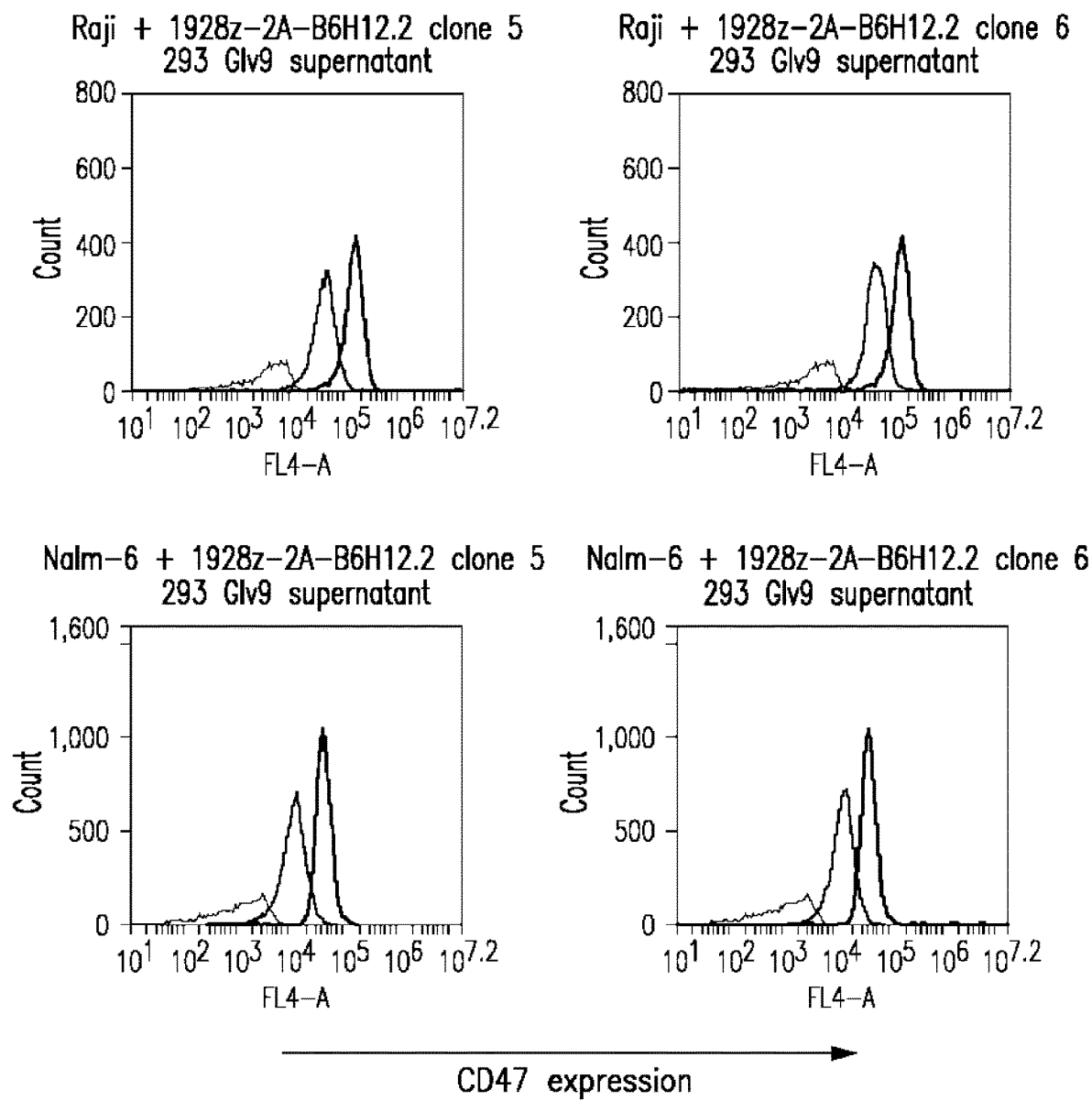

Constructs comprising 1928z-2A-B6H12.2 (FIGS. 1-5) were generated as confirmed by sequencing the CAR and scFv sequences. In addition, control constructs were generated with a CAR specific for the ovarian cancer antigen, MUC-CD, termed 4H1128z (FIG. 6). Stable producer cell lines were generated for the constructs utilizing the kappa leader sequence, and verified by flow cytometry (FIG. 7A). Supernatant from the packaging cell lines, containing secreted anti-CD47 scFV was able to block CD47 antibody from binding to Nalm-6 and Raji tumor cells in a flow cytometry based assay. Tumor cells incubated with supernatant from the packaging cells were also stained with an anti-c-myc tag antibody, to demonstrate binding of the scFv (FIG. 7B).

Figure 8A:
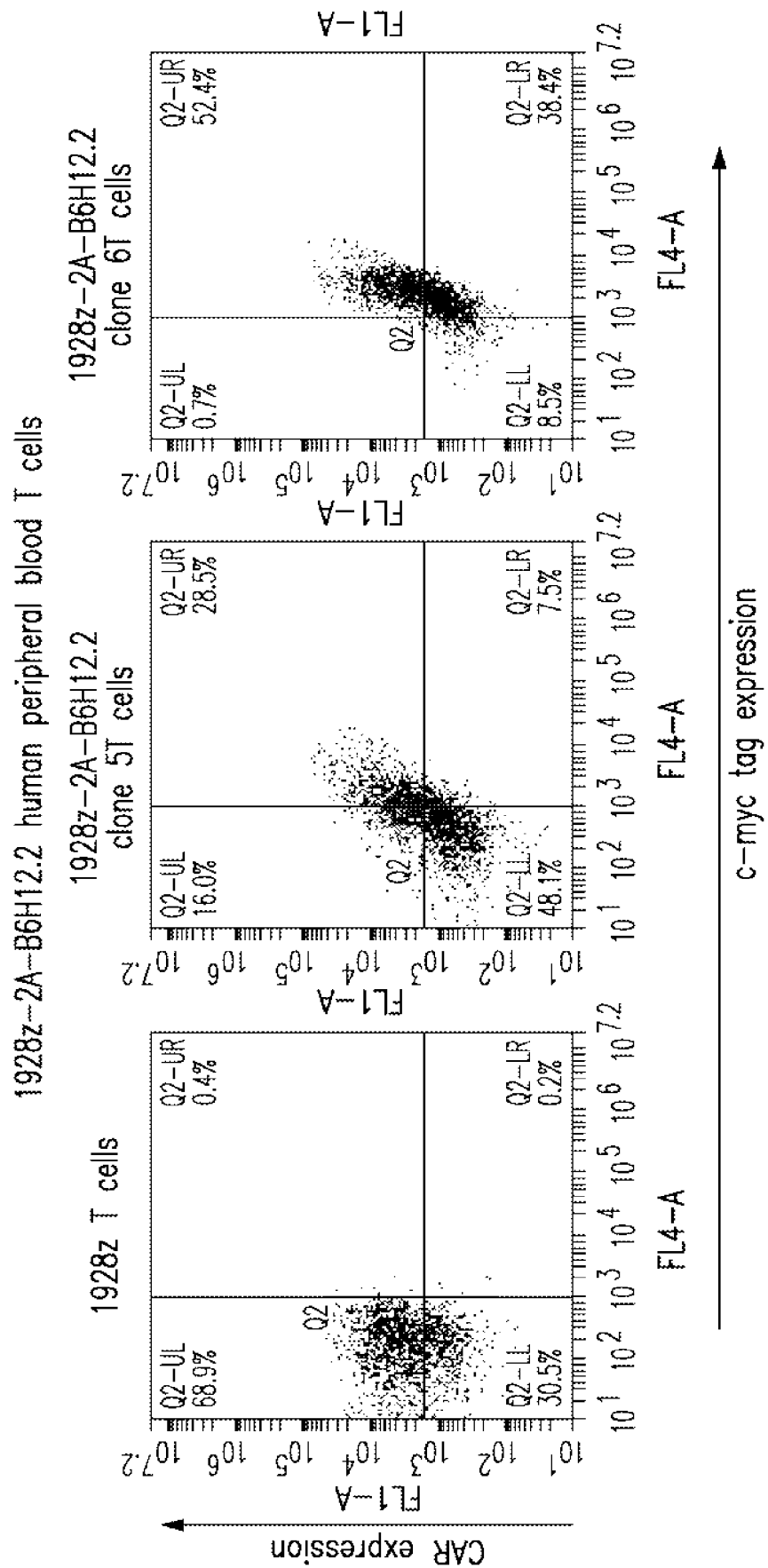
FIGS. 8A and 8B depict the generation of 1928z-2A-B6H12.2 human peripheral blood T cells. Human peripheral blood T cells were transduced with supernatant from 1928z or 1928z-2A-B6H12.2 packaging cells.
Figure 8B:
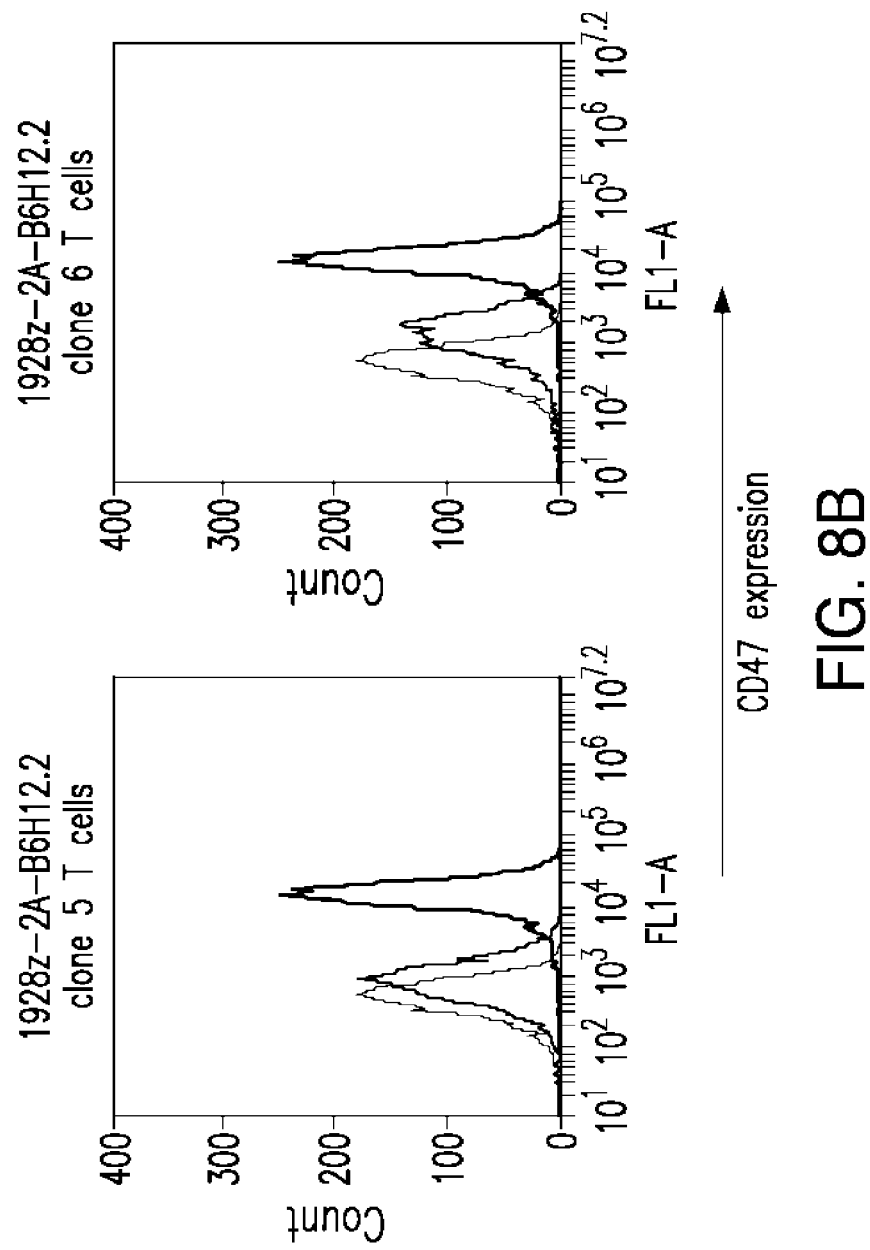
Figure 9A:
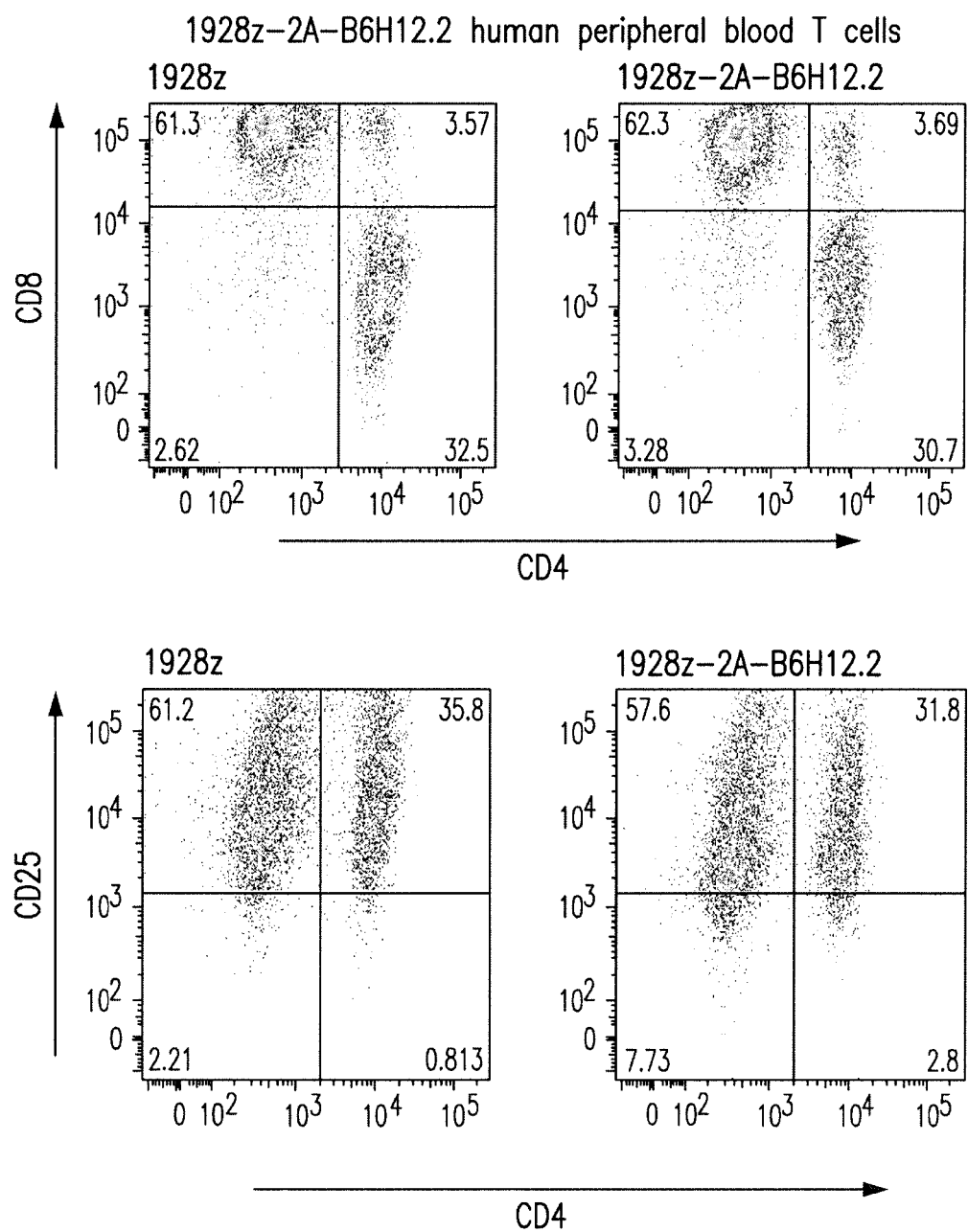
FIGS. 9A-9C depict 1928z-2A human peripheral blood T cells. Flow cytometry was performed to characterize the phenotype of 1928z and 1928z-2A-B6H12.2 T cells.
Figure 9A:
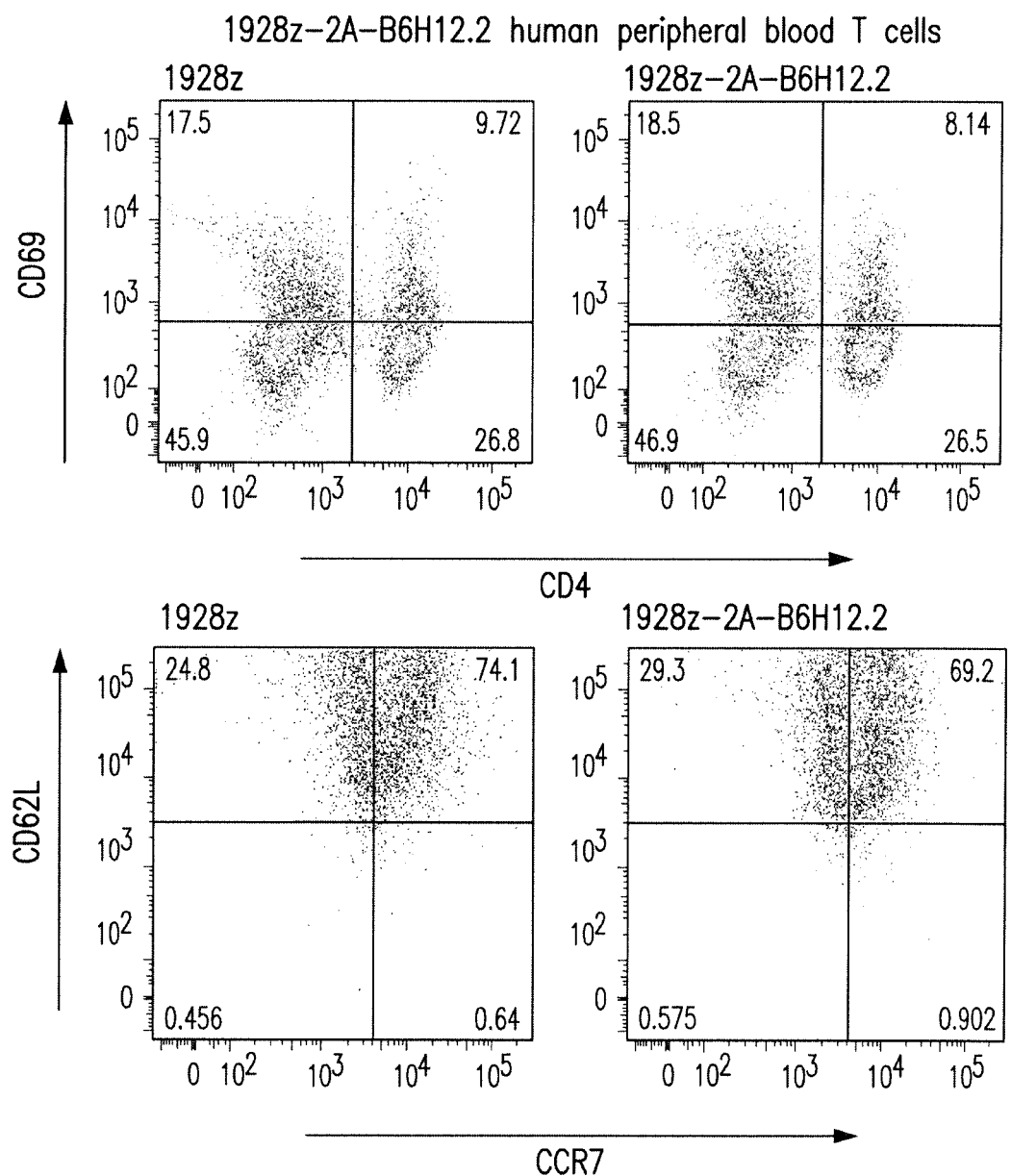
Figure 9B:
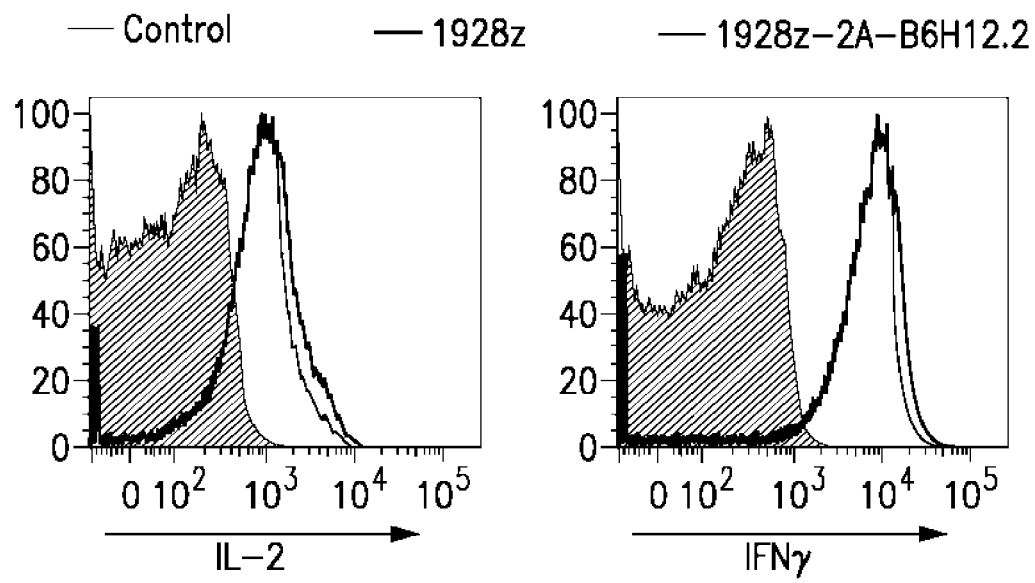
Figure 9C:
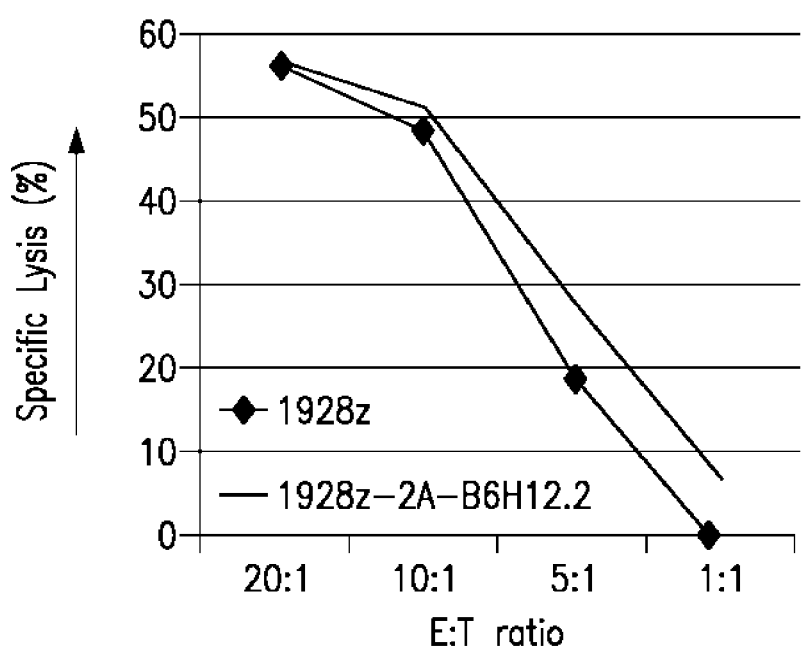

The packaging cells were utilized to transduce human peripheral blood T cells where transduction efficiency was assessed by flow cytometric analysis of CAR expression (FIG. 8A). The secreted scFv was able to function in an autocrine fashion, where an anti-CD47 antibody has reduced binding to 1928z-2A-B6H12.2 T cells compared to 1928z T cells. Positive staining with anti-c-myc tag antibody indicated bound scFv (FIG. 8B). The phenotype of the transduced T cells was investigated by flow cytometry and demonstrated to be similar between 1928z-2A-B6H12.2 and 1928z T cells, with the exception of CD62L, which was found to be decreased on 1928z-2A-B6H12.2 T cells (FIG. 9A). The function of T cells producing the anti-CD47 scFv was investigated using multiparameter flow cytometry and a standard 51Cr release assay. It was demonstrated that 1928z-2A-B6H12.2 T cells have equivalent cytokine production and cytotoxic function when compared to 1928z T cells (FIGS. 9B and 9C).

The ability of 1928z-2A-B6H12.2 T cells to respond to tumor in vivo was investigated using a preclinical SCID-Beige mouse model. SCID-Beige mice were injected intravenously with $1\times10^6$ Nalm-6 tumor cells modified to express Firefly luciferase, 3 days later mice were treated with $5.7\times10^6$ CAR$^+$ 1928z or 1928z-2A-B6Hl2.2 or control4Hll28z-2A-B6Hl2.2 T cells, also injected intravenously. Tumor progression was monitored clinically and with bioluminescent imaging. Treatment of tumor bearing mice with 1928z-2A-B6Hl2.2 T cells reduced tumor burden and enhanced the survival of tumor bearing mice compared to treatment with 1928z T cells (FIGS. 10A and 10B).

Example 2. T Cells Co-Expressing a Chimeric Antigen Receptor (CAR) and an Anti-Human PD-1 scFv had Increased Proliferation and Retained Expression of CAR An anti-human PD-1 scFv was generated based on the $V_H$ and $V_L$ chains from an anti-PD-1 antibody (clone 5C4) (U.S. Pat. No. 8,008,449). The 5C4 scFv was designed to include the kappa leader sequence, a serine glycine linker and the c-myc tag (FIG. 11). This scFv construct was cloned into SFG retriviral backbone to generate 1928z-2A-5C4 and 4H1128z-2A-5C4 (FIGS. 12 and 13). To develop a high affinity scFv that binds to human PD-1 (e.g., for expression in a 1928z/4H1128z CART cell), a human antibody phage display library is screened to determine scFvs that specifically bind human PD-1 (and potentially mouse PD-1).

Figure 14:
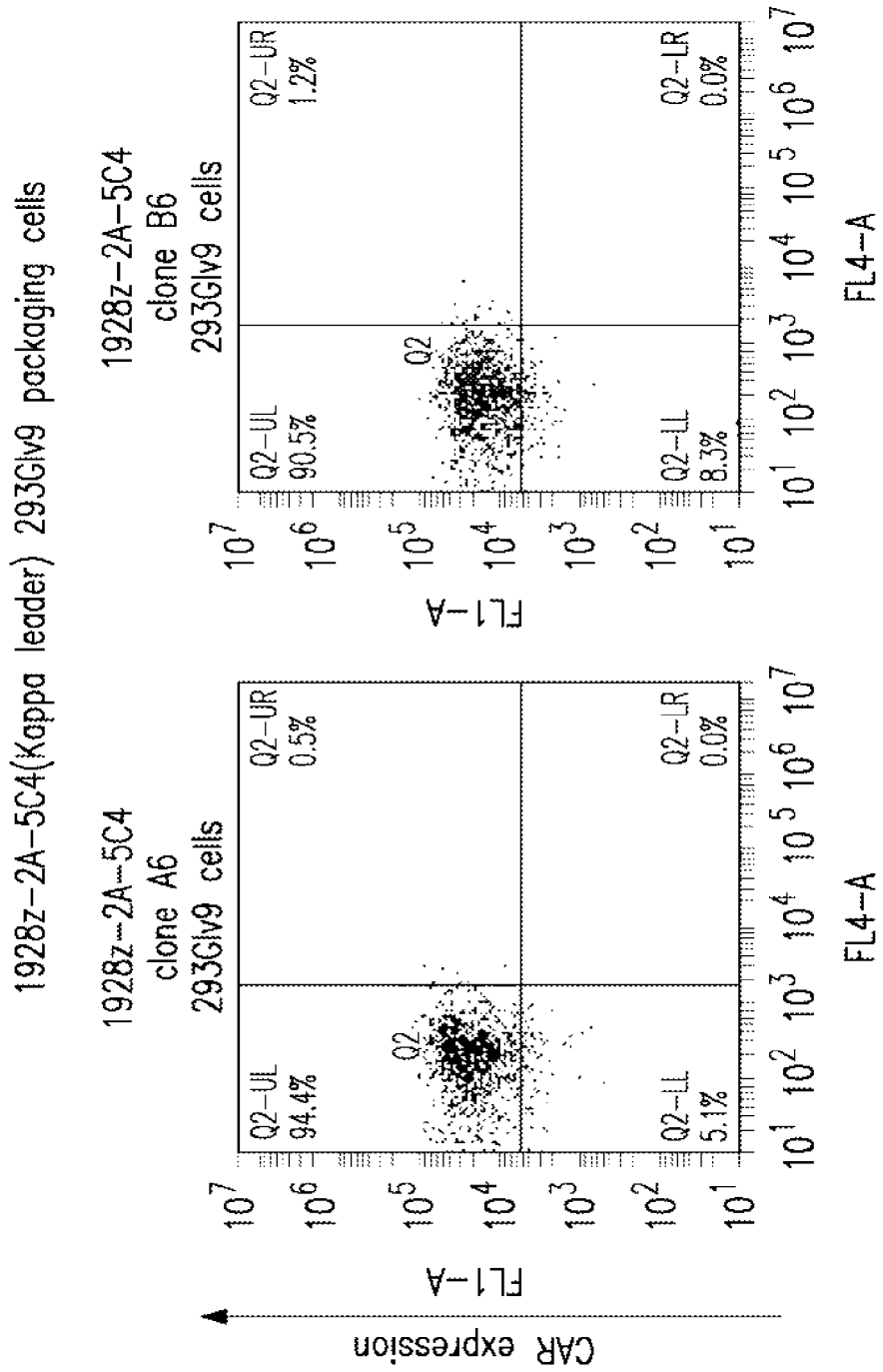
FIG. 14 depicts the generation of 1928z-2A-5C4 (Kappa Leader) 293Glv9 cells. Viral packaging cells were generated using the 1928z-2A-5C4. Two clones, clones A6 and B6, were selected based on expression of the 1928z CAR, which was comparable to control1928z 293Glv9 cells. CAR expression was determined by flow cytometry and staining with 12d11 antibody.
Figure 15:
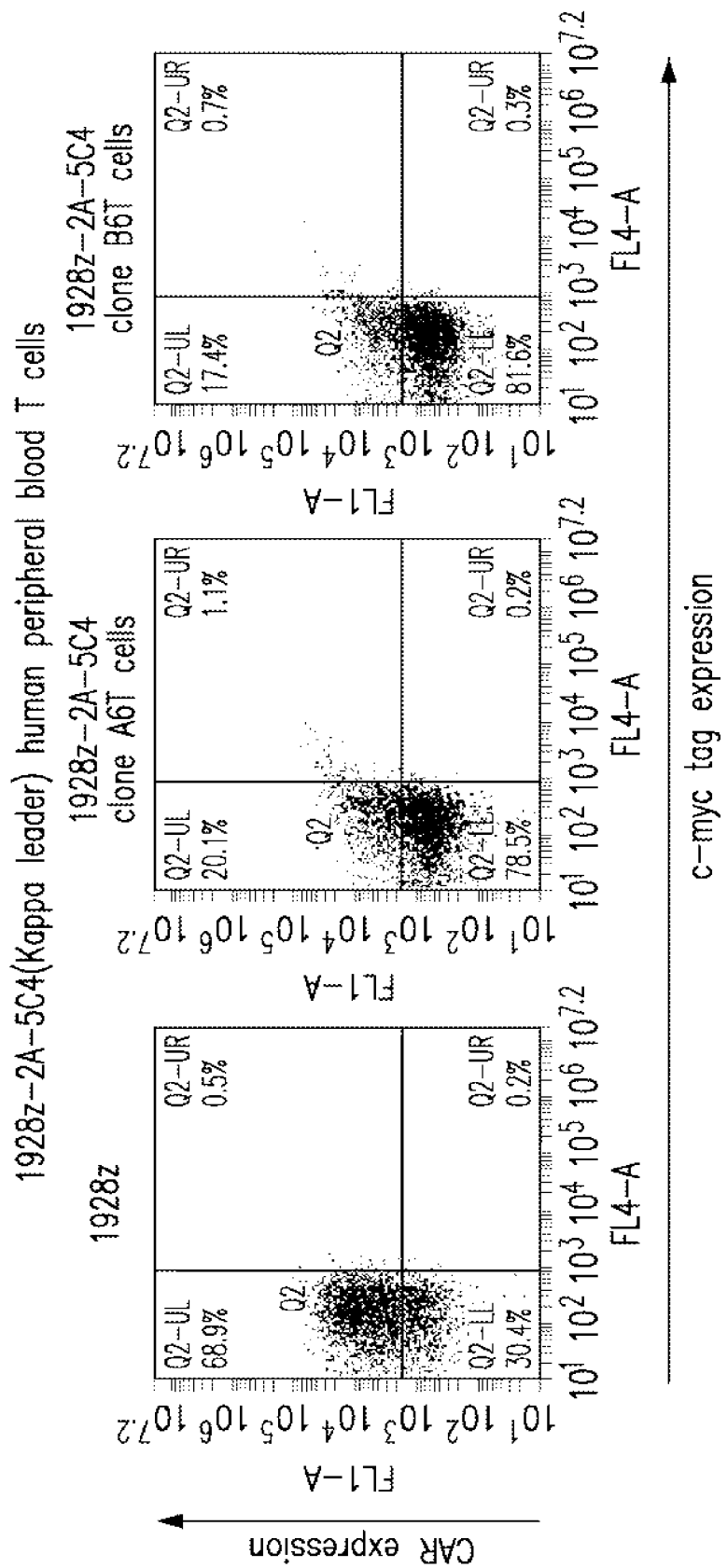
FIG. 15 depicts the generation of 1928z-2A-5C4 (kappa leader) human peripheral blood T cells. Human peripheral blood T cells were transduced with supernatant from 1928z or 1928z-2A-5C4 packaging cells. Flow cytometry was used to analyze CAR expression using the 12d11 antibody and of bound anti-CD47 scFv using staining with a fluorescently tagged anti-c-myc tag antibody.

Stable 293Glv9 packaging cell lines were produced and expression of the 1928z CAR and 4H1128z CAR was assessed by flow cytometry (FIG. 14). Supernatant from these packaging cells was utilized to transduce human peripheral blood T cells and transduction efficiency was assessed by flow cytometry to detect CAR expression (FIG. 15).

Figure 16A:
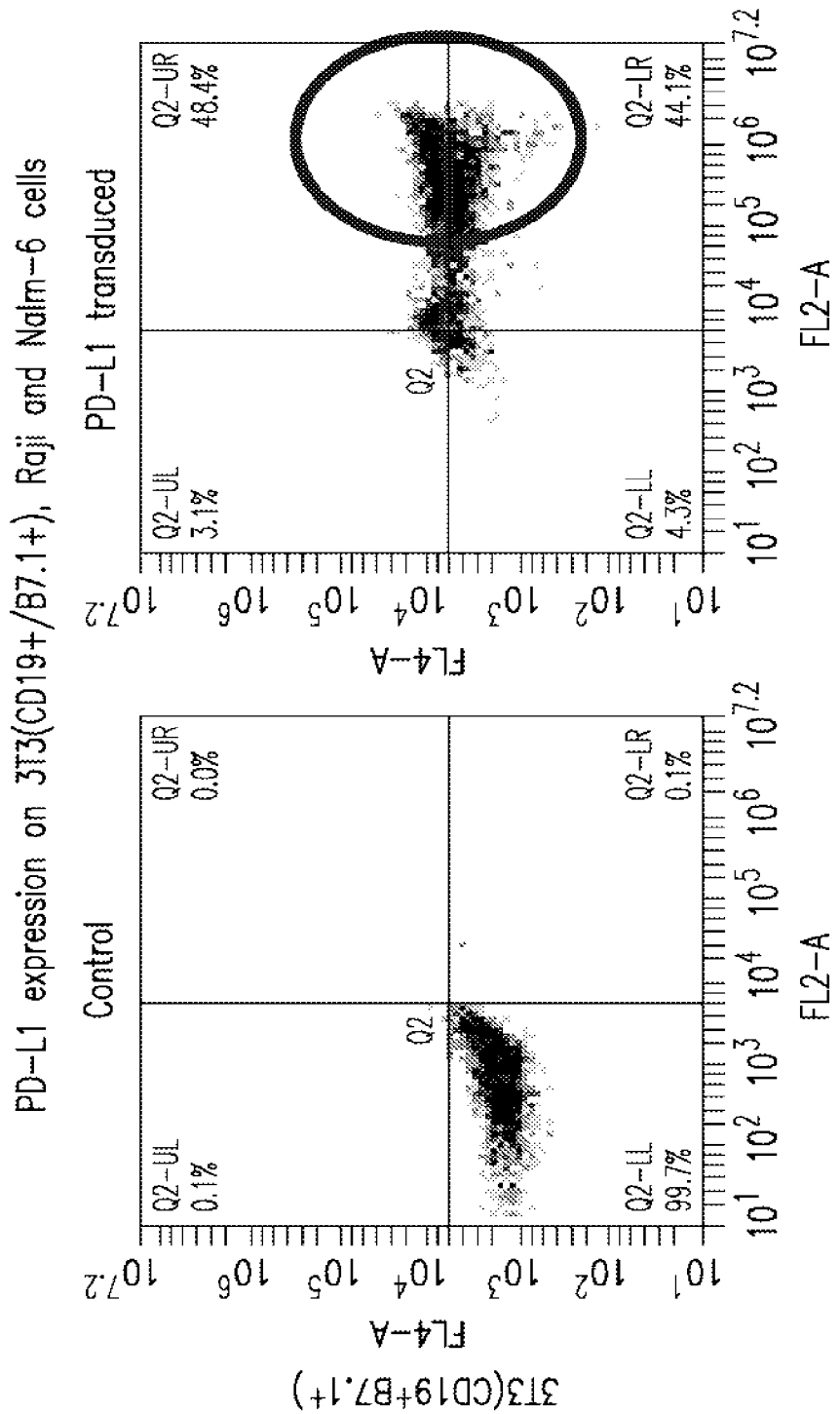
FIGS. 16A-16C depict PD-L1 expression on 3T3(CD19$^+$/B7.1$^+$), Raji and Nalm-6 cells. Flow cytometry was used to determine expression of PD-L1 on 3T3 (CD19$^+$/B7.1$^+$), Raji and Nalm-6 cells that had been transduced to express PD-L1. Transduced cells expressed significant levels of PD-L1 compared to control untransduced cells and circled populations were sorted for use in experiments.
Figure 16B:
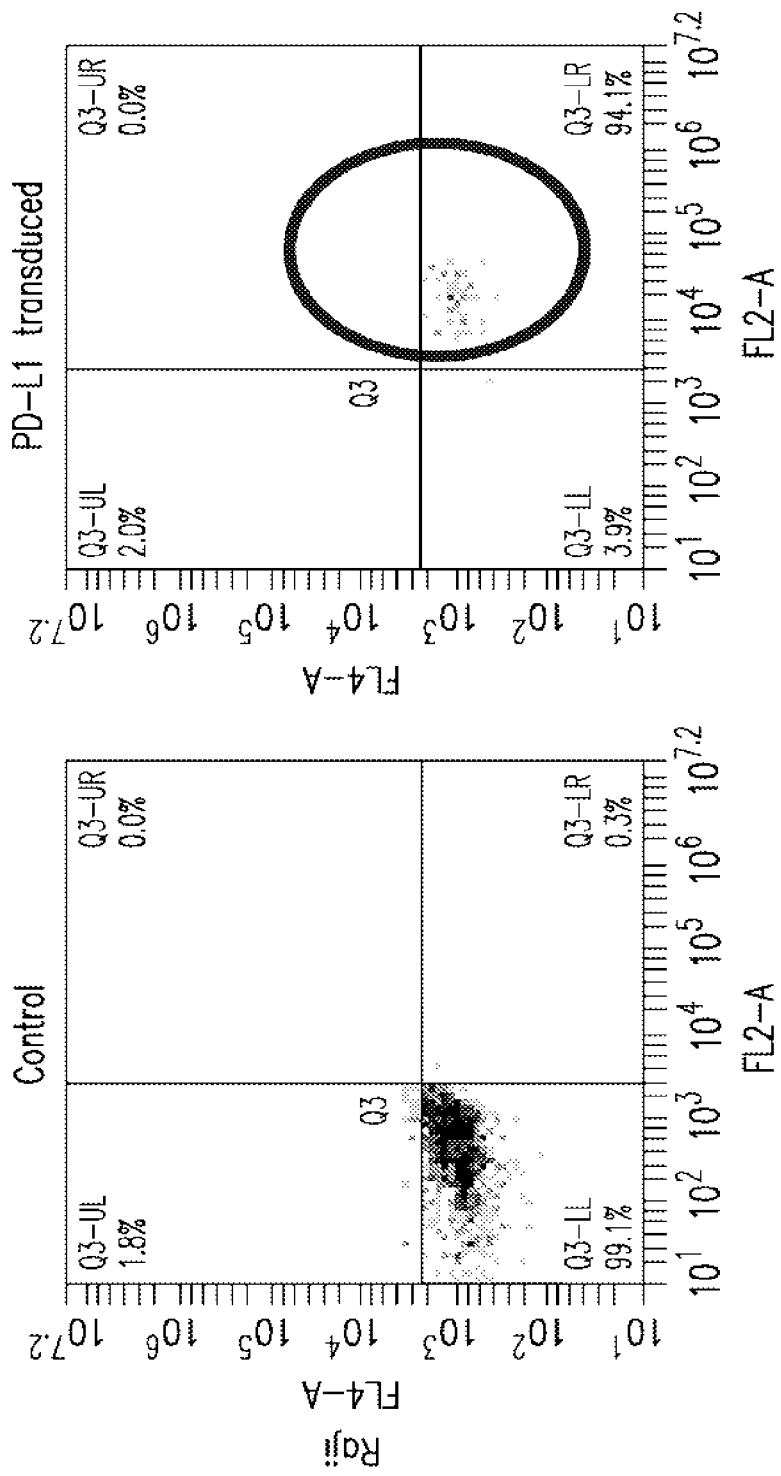
Figure 16C:
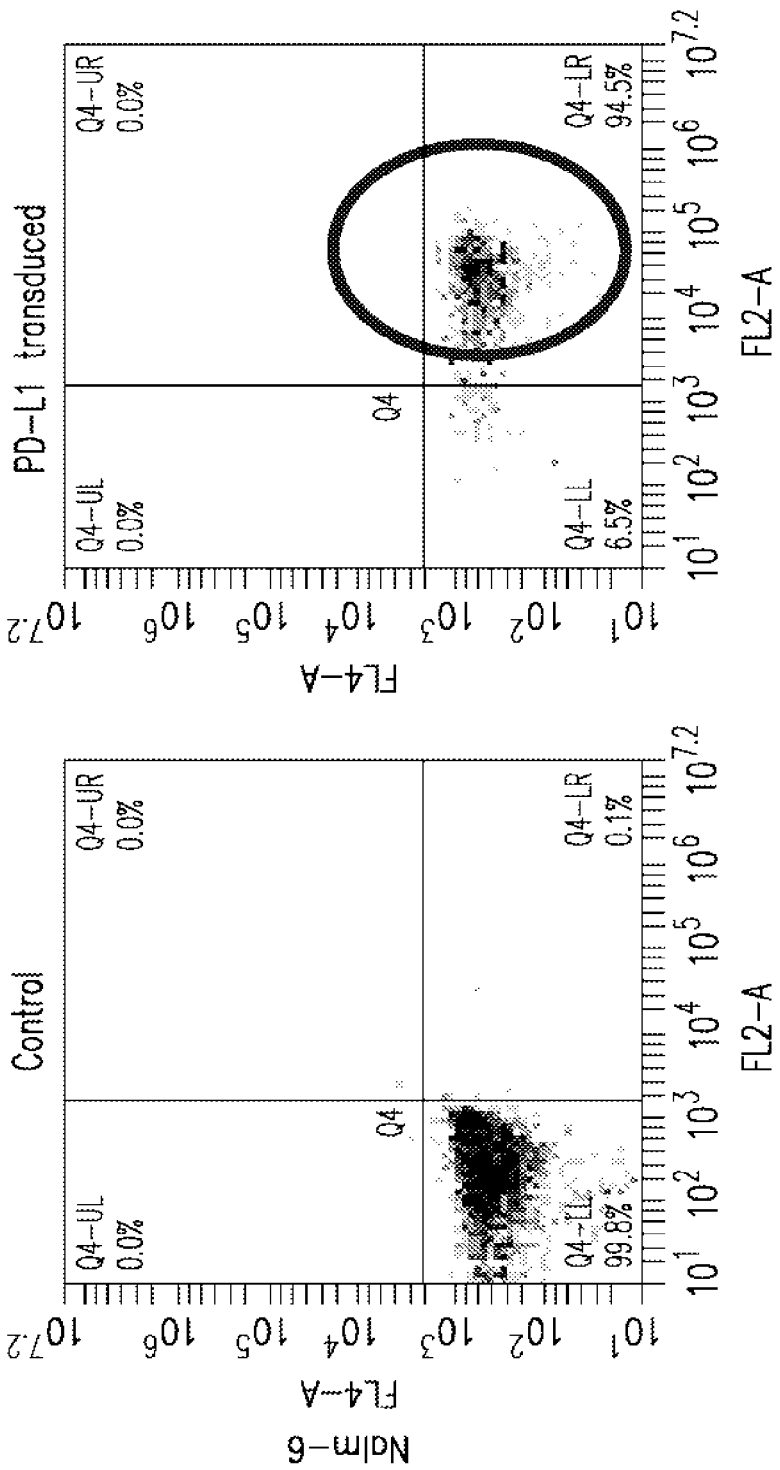
Figure 17:
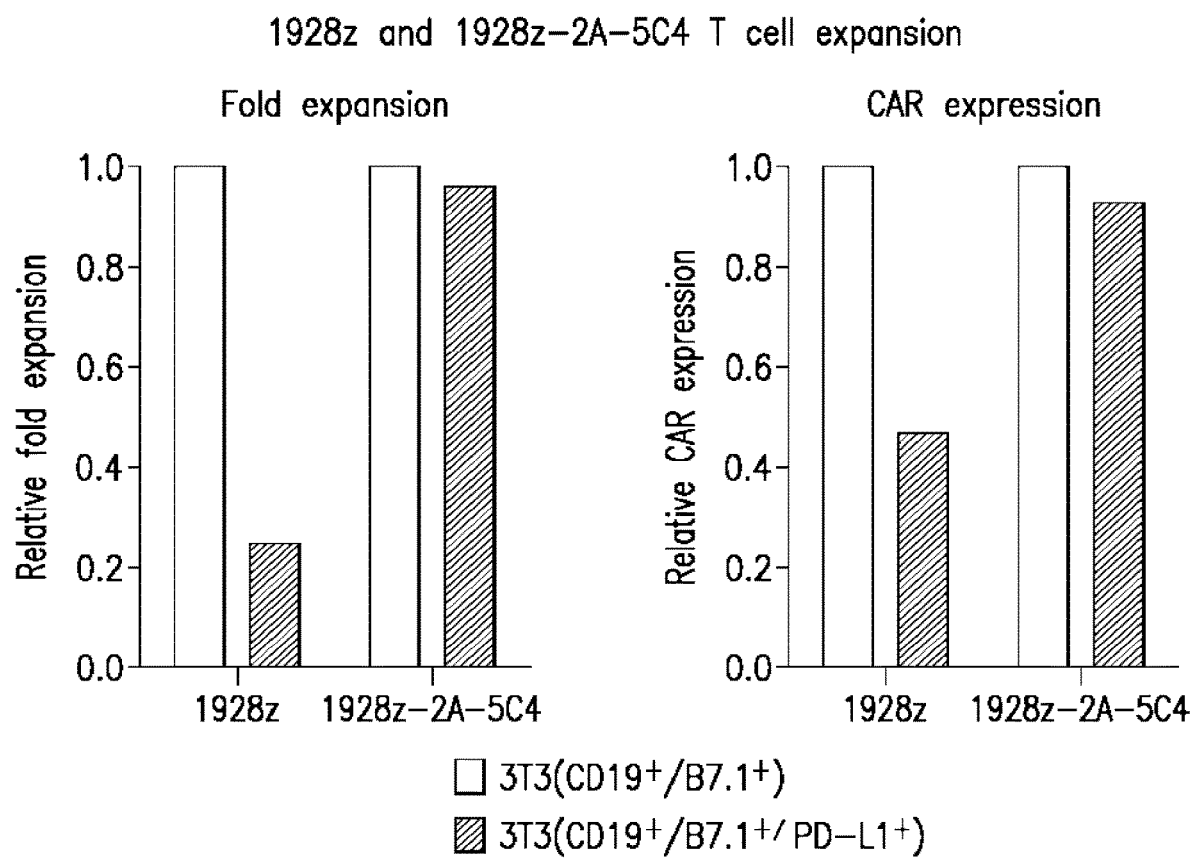
FIG. 17 depicts 1928z and 1928z-2A-5C4 T cell expansion. 1928z and 1928z-2A-5C4 T cells were incubated with 3T3(CD19$^+$/B7.1$^+$) or 3T3(CD19$^+$/B7.1$^+$/PD-L1$^+$), T cell expansion was monitored with Trypan blue and CAR expression was determined by flow cytometry. Expansion and CAR expression was correlated to that of cells expanded on 3T3(CD19$^+$/B7.1$^+$) cells.

The ability of this anti-human PD-1 scFv to increase proliferation of T cells in response to artificial antigen presenting cells (aAPCs) was investigated. PD-L1 positive tumor cells and 3T3 aAPCs were generated for the study (FIG. 16). Following co-culture of transduced T cells with 3T3 aAPCs expressing human CD19, human B7.1 and human PD-L1, 1928z-2A-C4 T cells had increased proliferation and retained expression of CAR compared to 1928z T cells (FIG. 17). The phenotype and anti-tumor function of T cells co-expressing 1928z CAR and anti-PD1 scFV can be determined using flow cytometry, luminez cytokine analysis studies, $^{51}$Chromium release assays, and SCID-Beige preclinical model to determine in vivo anti-tumor function.

Figure 18:
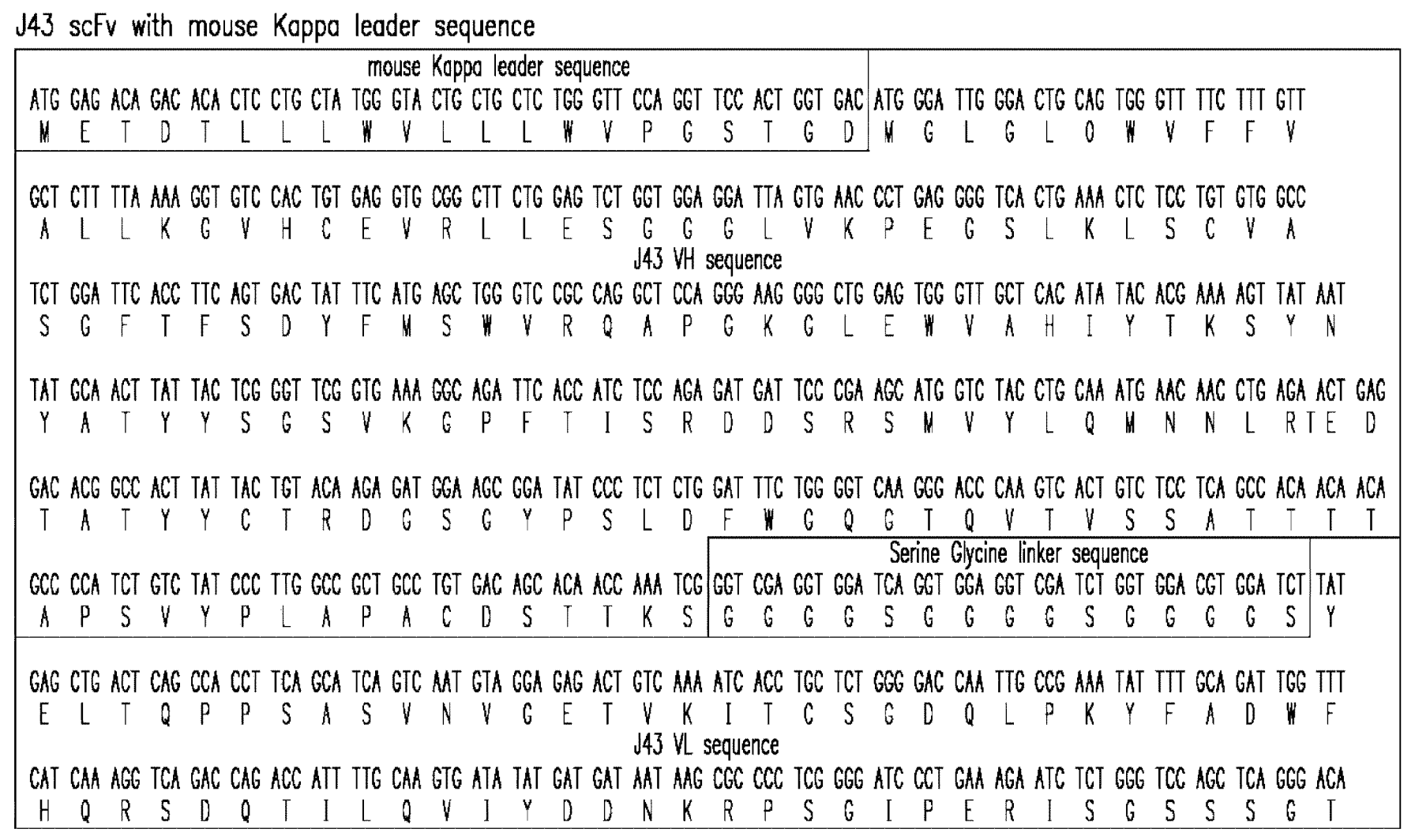

Example 3. Co-Expression of a Chimeric Antigen Receptor (CAR) and an Anti-Mouse PD-1 scFv Stimulates Mouse T Cells An anti-mouse PD-1 scFv was generated based on the V H and VL from the anti-PD-1 antibody clone J43 (U.S. Pat. No. 7,858,746 to Honjo et al.). The J43 scFv was designed to include the mouse kappa chain leader sequence, a serine glycine linker and the c-myc tag (FIG. 18). This scFv construct was cloned into SFG retroviral backbone expressing the CAR targeting human CD19 or human MUC-CD that signals through mouse C28 and mouse CD3zeta, therefore stimulating mouse T cells. These constructs 19m28mz-IRES-J43 (FIG. 19) and 4H11m28mz-IRES-J43 (FIG. 20) are used to generate stable Phoenix packaging cells lines and genetically modify primary murine T cells, as previously described (Lee et al., Cancer Res 2011, 71(8):2871). Mouse 19m28mz and 19m28mz-IRES-J43 T cells are cultured with EL4 thymoma tumor cells that have been modified to express human CD19 and mouse PD-L1, proliferation of mouse T cells to monitor viable cell counts and CFSE labeling.

For murine T cells expressing the 4H11m28mz CAR that target the MUC-CD antigen, function can be assessed in response to IDS tumor cells modified to express MUC-CD and mouse PD-L1 (Chekmasova et al., Clin Cancer Res, 2010, 16:3594). A human scFv that binds murine PD-1, as described above, is cloned into the SFG-19m28mz and 4H11m28mz vector constructs and used to modify murine T cells. Syngeneic models to assess the in vivo anti-tumor effects of the T cells modified to express human scFv that binds murine PD-1 are available: an ovarian cancer tumor model utilizing ID8-MUC-CD tumor cells, which are inoculated intraperitoneally into C57BL/6 mice; and transgenic mice that express human CD19 in place of mouse CD19, which are inoculated with EL4 thymoma tumor cells modified to express human CD19 (Pegram et al., Blood 2012, 119(18):4133). Thus, the anti-tumor effect can be evaluated in an immune-competent model, therefore, allowing assessment of the impact of the anti-PD-1 scFv on the tumor microenvironment.

Example 4. Co-Expression of a Chimeric Antigen Receptor (CAR) and Agonistic scFv in Immune Cells In one embodiment, the invention provides an immune cell that expresses an antigen binding receptor (e.g., CAR or TCR) and a single-chain variable fragment (scFv) that binds an antigen having agonistic immunostimulatory activity (e.g., CD28, OX-40, 4-1BB, and ligands thereof). To generate agonistic scFvs targeting costimulatory molecule 4-1BB, the 3H3 hybridoma cell line was obtained (Shuford et al., J Exp Med 1997, 186:47-55; provided by Professor Mick Croft (La Jolla Institute for Allergy and Immunology)). To generate agonistic scFvs targeting costimulatory molecule OX-40, OX-86 hybridoma cell line was obtained (al-Shamkhani et al., Eur J Immunol 1996, 26(8):1695-9; European Collection of Cell Cultures (Catalogue number 96110601)). Hybridoma mRNA was isolated from cells using a QIAgen RNAeasy kit, as per manufacturer's instruction (QIAgen, CA, USA), and cDNA was then prepared using New England Biolabs Protoscript AMV First strand cDNA synthesis kit, as per the manufacturers instruction (New England Biolabs, MA, USA). The variable heavy (VH) and light (VL) chains were then PCR amplified using the following degenerate primers:

```
Orlandi Primers (Orlandi et al., Proc. Natl. Acad.
Sci. 1989, 86:3833-37)
VHFOR:
                                          [SEQ ID NO: 28]
5'-tga gga gac ggt gac cgt ggt ccc ttg gcc cca g-3'

VH1BACK:
                                          [SEQ ID NO: 29]
5'-agg tsm arc tgc ags agt cwg g-3'

VKFOR:
                                          [SEQ ID NO: 30]
5'-gtt aga tct cca gcttgg tcc c-3'

VK1BACK:
                                          [SEQ ID NO: 31]
5'-gac att cag ctg acc cag tct cca-3'

Cooper Primers (Wang et al., Blood 2002, 99:2459-
2467)
Vk
                                          [SEQ ID NO: 32]
5'-GGCTGCAGSTTCAGTGGCAGTGGRTCWGGRAC-3', Ck
                                          [SEQ ID NO: 33]
5'-CTCATTCCTGTTGAAGCTCTTGACAATGGG-3';

RACE PRIMERS (Kettleborough etal., Eur. J
Immunol1993, 23:206-211)
VKfr1a:
                                          [SEQ ID NO: 34]
Ata tcc atg gca gac gtc cag atg atc cag tct cca Vkfr1b:
                                          [SEQ ID NO: 35]
ata tcc atg gca gac att gtg ctg act cag tct cc Vkfr1c:
                                          [SEQ ID NO: 36]
ata tcc atg gca gat gtt gtg atg acc caa act cca Vkfr1d:
                                          [SEQ ID NO: 37]
ata tcc atg gca caa att gtt ctc acc cag tct cc Vkfr1e:
                                          [SEQ ID NO: 38]
ata tcc atg gca gac att gtg atg aca cag tct cca Vkfr1f:
                                          [SEQ ID NO: 39]
ata tcc atg gca gat att gtg atg acg cag gct gca Vkfr1g:
                                          [SEQ ID NO: 40]
ata tcc atg gca gac att gtg atg acc cag tct c Reverse Kappa:
                                          [SEQ ID NO: 41]
gct tca aca gga atg agt gtt aac tcg agg tag
```

To assemble the VH and VL into a scFv, a serine glycine linker is added during PCR of the VH And VL chains, as well as c-myc tag and murine Ig Kappa chain or CD8 leader sequence. The resulting polynucleotide is cloned into an existing retroviral expression vector (SFG backbone) encoding the 1928z chimeric antigen receptor (CAR), to generate SFG-1928z-2A-3H3 or 1928z-2A-OX86.

Stable packaging cell lines are generated as described for the anti-mouse PD-1 J43 scFv, and tested in a similar murine model of adoptive T cell transfer.

Figure 21:
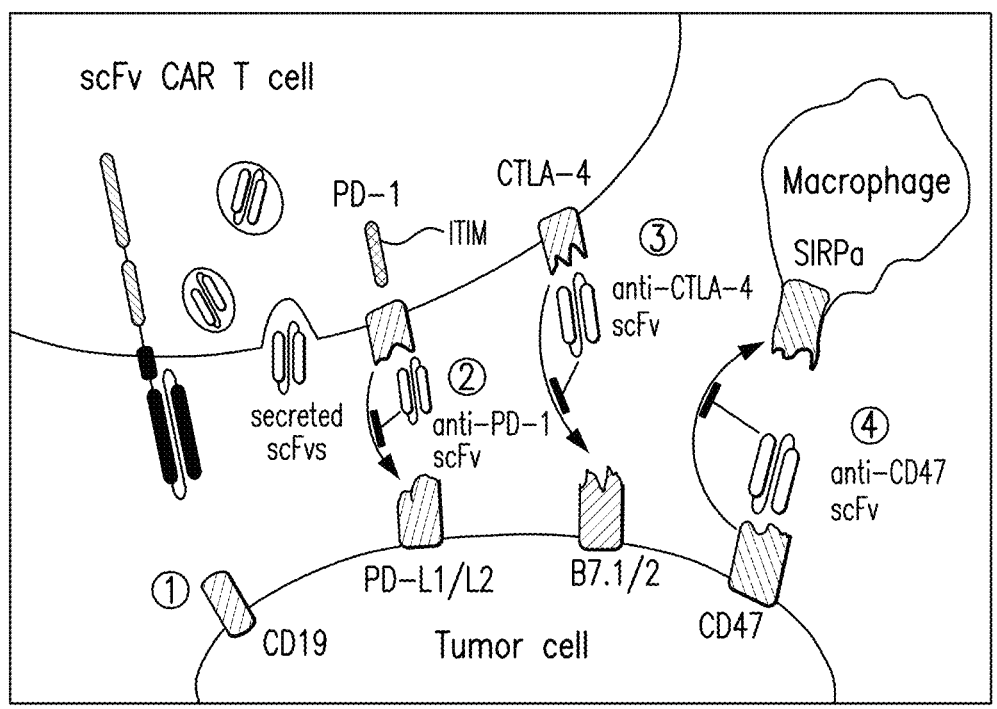
FIG. 21 depicts strategies to genetically modify CART cells to express scFv molecules ("armored CAR T cells") to overcome "hostile" tumor microenvironment. CAR$^+$ T cells may be modified to secrete antagonistic scFvs with immune regulatory functions. Upon activation of the CAR to cognate antigen (1), armored CAR modified T cells may be induced to secrete scFvs antagonistic to the inhibitory PD-1 T cell receptor on both infused CAR modified T cells and endogenous anti-tumor T cells enhancing anti-tumor effector function (2), induced to secrete scFvs antagonistic to the inhibitory CTLA-4 T cell receptor on both infused CAR modified T cells and endogenous anti-tumor T cells enhancing anti-tumor effector function (3), or induced to secrete an scFv antagonistic to the CD47 receptor expressed on the tumor cell reversing the cloaking the tumor cell from recognition by the host innate anti-tumor immune response leading to recognition and eradication of tumor by host macrophages.

The results presented herein indicate genetically modified CAR T cells expressing scFv molecules ("armored CART cells") are immunoresponsive and can overcome "hostile" tumor microenvironment, and, thus, are effective in the treatment of neoplasia. CAR+ T cells are modified to secrete antagonistic scFvs with immune regulatory functions (FIG. 21). Upon activation of the CAR to cognate antigen (1), armored CAR modified T cells may be induced to secrete scFvs antagonistic to the inhibitory PD-1 T cell receptor on both infused CAR modified T cells and endogenous anti-tumor T cells enhancing anti-tumor effector function (2), induced to secrete scFvs antagonistic to the inhibitory CTLA-4 T cell receptor on both infused CAR modified T cells and endogenous anti-tumor T cells enhancing anti-tumor effector function (3), or induced to secrete an scFv antagonistic to the CD47 receptor expressed on the tumor cell reversing the cloaking the tumor cell from recognition by the host innate anti-tumor immune response leading to recognition and eradication of tumor by host macrophages.

Results reported herein were obtained using the following methods and materials unless indicated otherwise.

Generation of Anti-CD47 B6H12.2 scFv

The B6H12.2 hybridoma cell line was obtained from the American Tissue Culture Collection (ATCC, VA, USA; catlogue number HB-9771). B6H12.2 mRNA was isolated from hybridoma cells using a QIAgen RNAeasy kit, according to manufacturer's instruction (QIAgen, CA, USA), and cDNA was prepared using New England Biolabs Protoscript AMV First strand cDNA synthesis kit, according to manufacturer's instruction (New England Biolabs, MA, USA). The variable heavy (VH) and light (VL) chains were PCR amplified using primers designed to incorporate the Kappa leader sequence, serine glycine linker and c-myc tag (see FIG. 1) as follows:

```
Primer 1. B6H12.2 VH forward primer [SEQ ID NO:
42]:
5'-CCA TGG AGA CAG ACA CAC TCC TGC TAT GGG TAC TGC
TGC TCT GGG TTC CAG GTT CCA CTG GTG ACG AGG TGC
TGC AGC TGG TGG AGT CCG GGG-3'

Primer 2. B6H12.2 VH reverse primer [SEQ ID NO:
43]:
5'-AGA TCC ACC TCC ACC AGA TCC ACC TCC ACC TGA TCC
ACC TCC ACC TGA GGA GAC GGT GAC TGA GGT TCC TTG
ACC-3'

Primer 3. B6H12.2 VL forward primer [SEQ ID NO:
44]:
5'-GGT GGA GGT GGA TCA GGT GGA GGT GGA TCT GGT GGA
GGT GGA TCT GAC ATT GTG ATG ACT CAG TCT CCA GCC
ACC-3'

Primer 4. B6H12.2 VL reverse primer [SEQ ID NO:
45]:
5'-CTC GAG TTA CAG ATC CTC TTC TGA GAT GAG TTT TTG
TTG TTT GAT TTC CAG CTT GGT GCC TCC ACC GAA CG-3'
```

In addition to the above design, an scFv with the CD8L sequence was generated to determine an efficient leader sequence for exportation of the scFv from T cells using the following alternative forward primer:

```
Primer 5. B6H12.2 VH CD8L forward [SEQ ID NO:
46]:
5'-TAT ACC ATG GCC TTA CCA GTG ACC GCC TTG CTC CTG
CCG CTG GCC TTG CTG CTC CAC GCC GCC AGG CCG GAG
GTG CAG CTG GTG GAG TCC GGG-3'
```

The VH and VL PCR products were cloned into pCR2.1TOPO, according to manufacturer's instruction (Invitrogen, NY, USA). Sequencing using M13F2 and M13R2 primers (Invitrogen) was performed by the MSKCC DNA sequencing core facility to confirm the sequence of both the VH and VL products. Overlapping PCR was performed using the VH and VL PCR products and primers 1 or 5 and 4 to generate the anti-CD47 scFv (see FIG. 1).

The anti-CD47 scFv construct was cloned into an existing retroviral expression vector (SFG backbone) encoding the 1928z chimeric antigen receptor (CAR), to generate SFG-1928z-2A-B6H12.2. The SFG-1928z-2A-B6H12.2 DNA was sequenced to confirm the sequence.

Generation of Stable Packaging Cell Line for Human T Cells

To generate stable packaging cell lines, H29 cells were transiently transfected with 10 ng of SFG-1928z-2A-B6H12.2 DNA using a Promega calcium phosphate transfection kit, according to manufacturer's instructions (Promega). Supernatant from H29 supernatant was used to transduce 293Glv9 cells, which were subsequently subcloned to generate stable packaging cells. Selection of two sub-clones (clone 5 and clone 6) was based upon expression of both 1928z CAR and ability of 293Glv9 supernatant to transduce human peripheral blood T cells (as determined by flow cytometry following staining with 12d11 antibody). Transduction of human peripheral blood T cells was performed as described previously (Brentjens et al., Clin Cancer Res 2007, 13(18Pt1):5426).

Assessment of Anti-CD47 scFv Production/Function

Production of anti-CD47 scFv from 1928z-2A-B6H12.2 293Glv9 and transduced human peripheral blood T cells was determined by incubating CD47+ tumor cells (Raji and Nalm-6) in supernatant from these cells. Tumor cells were subsequently washed and stained with fluorescently conjugated anti-c-myc tag antibody (Cell Signaling, MA, USA) to detect supernatant derived protein bound to the tumor cells. Tumor cells were also stained with fluorescently conjugated anti-CD47 (clone B6H12.2, eBioscience) to detect ability of B6Hl2 scFv to block CD47.

In Vivo Adoptive Transfer Model

Mice were injected intravenously with 1×106 Nalm-6 modified to express Firefly luciferase (day 0). On day 3, mice were treated with 5.7×106 CAR+ T cells, also inoculated intravenously. Tumor progression was monitored clinically and using bioluminescent imaging, as described previously (Santos et al., Nature Medicine 2009, 15(3):338).

Generation of 5C4 Anti-Human PD-1 scFv

The sequence for an antibody that specifically binds human PD-1, clone 5C4, was obtained, as described above. This sequence was modified to include a kappa leader sequence, serine glycine linker and the c-myc tag and purchased from GeneArt (Invitrogen, FIG. 9). Cloning of this scFv into SFG retroviral backbone, generation of stable packaging cells, transduction of human peripheral blood T cells and assessment of transduction efficiency was achieved as described above.

Assessment of Anti-Human PD-1 Function

The PD-1ligand, PD-L1 was PCR amplified from SKOV3 (ATCC) tumor cells that were incubated in 200 ng/ml recombinant human Interferon-gamma (RnD systems, MN, USA). Primers used to amplify human PD-L1 are shown below:

```
Primer 6. Human PD-L1 forward primer [SEQ ID NO:
47]
5'-CACGTGCCATGGATGAGGATAT TTGCTGTCTT TATAT-3'

Primer 7. Human PD-L1 reverse primer [SEQ ID NO:
48]
5'CTCGAGTTACGTCTCCTCCAAATGTGTATCACTTT3'
```

The human PD-L1 sequence was cloned into a SFG retroviral backbone, and transduced into 3T3, Raji and Nalm-6 cell lines as described previously (Brentjens et al., Clin Cancer Res 2007, 13(18 Pt 1):5426). Cells were stained with anti-PD-L1 (clone MIH1, BD Pharmingen, CA, USA) and FACS sorted to ensure the total cell population expressed PD-L1 (FIG. 14).

Human 1928z-2A-5C4 and 1928z T cells were cultured with 3T3 (CD19/B7.1/PD-L1) aAPCs and viable cell counts were performed utilizing trypan blue exclusion and flow cytometry was performed to determine expression of the CAR. This was correlated to expansion of T cells when cultured with 3T3 (CD19/B7.1) aAPCs.

Generation of Anti-Mouse PD-1 scFv

The sequence for an antibody that specifically binds murine PD-1, clone name J43, was obtained, as described above. This sequence was modified to include a Kappa chain leader sequence and c-myc tag sequence, with a serine glycine linker to form a scFv and purchase from GeneArt (Invitrogen, FIG. 16). This was cloned into an existing retroviral expression vector (SFG) encoding a murine CAR, where signaling is mediated through mouse CD28 and CD3 zeta molecules. The 19m28mz-IRES-J43 and 4H11m28mz-IRES-J43 were generated to target B cell and ovarian tumor respectively (FIGS. 17 and 18).

Assessment of Anti-Mouse PD-1 Function

The PD-1ligand, PD-L1 was PCR amplified from Renca tumor cells (ATCC), primers used to amplify mouse PD-L1 are shown below:

```
Primer 8. Mouse PD-L1 forward primer [SEQ ID NO:
49]
5'-TAT TAC ACG TGT TAC ATG AGG ATA TTT GCT GTC
TTT-3'

Primer 9. Mouse PD-L1 reverse primer [SEQ ID NO:
50]
5' TAT AGG ATC CTC GAG GAT GTT ACG TCT CCT CCA AAT
GTG TA 3'
```

The anti-mouse PD-1 scFv was cloned into an SFG retroviral backbone, and transduced into 3T3 aAPCs, IDS and EL4 cell lines. Cells stained with anti-PD-L1 (clone MIH1 BD Pharmingen) are FACS sorted to ensure the total cell population expressed PD-L1.

CTL Chromium Release Killing Assays

Target cells expressing desired antigen were labeled with 51Cr and co-cultured with T cells at decreasing effector: target ratio's. After 4 hours of culture, supernatant was removed and used to measure radioactivity released from chromium. Specific lysis was determined by subtracting background radioactivity of target cells not cultured with 25T cells and dividing by the radioactivity measured from target cells completely lysed by using 0.2% Triton X-100.

Example 5. Blocking CD47 Improves CAR T Cell Therapy

T cells can be genetically modified to target tumor antigens through the expression of a chimeric antigen receptor (CAR). Adoptive transfer of CD19-specific CAR T cells has shown clinical efficacy in some patients with hematological malignancies, however chronic lymphocytic leukemia patients with bulky lymphadenopathy have suboptimal responses to CAR T cell therapy. Furthermore, CAR T cell therapy has failed to demonstrate efficacy against solid tumors in clinical trials. To enhance the clinical efficacy of CAR T cells we propose to recruit an innate anti-tumor immune response through the secretion of a CD47-blocking single chain variable fragment (scFv) from CAR T cells. Previous studies show that blocking the interaction between CD47 on tumor cells and SIRPa on macrophages results in phagocytosis of tumor cells. To harness this effect, T cells were modified to express the CD19-specific CAR (1928z) and secrete a scFv specific for human CD47, cloned from the B6H12.2 hybridoma (1928z/B6H12.2 T cells). 1928z/B6H12.2 T cells were shown to secrete a functional scFv specific for human CD47, which did not affect CAR-mediated cytokine secretion or cytotoxicity in vitro. Supernatant from 1928z/B6H12.2 T cells but not 1928z T cells stimulated macrophages to phagocytose tumor cells in vitro. Adoptive transfer of 1928z/B6H12.2 T cells mediated enhanced anti-tumor effects and eradicated Nalm6 tumors in a preclinical murine model. This novel strategy combines CAR T cell-mediated effects and innate immune cell-mediated destruction of tumor cells, which may improve the anti-tumor efficacy of CAR T cell therapy

Example 6. Enhancing Anti-Tumor Efficacy of Chimeric Antigen Receptor Modified T-Cells Through Constitutive CD40L Expression Adoptive cell therapy with genetically modified T-cells expressing a chimeric antigen receptor (CAR) is a promising therapy for patients with B-ALL. However, in most clinical trials CAR-modified T-cells have failed to demonstrate a significant therapeutic benefit, specifically in the context of low grade B-cell malignancies and solid tumors. In the experiments presented in this example section, we further enhance the anti-tumor efficacy of CAR-modified T-cells by engineering T-cells to constitutively express CD40 ligand (CD40L, CD154). T-cells modified to constitutively express CD40L (CD40L-modified T-cells) increased proliferation and secretion of pro-inflammatory TH1 cytokines. Further, CD40L-modified T-cells augmented the immunogenicity of CD40+ tumor cells by the upregulation of co-stimulatory molecules (CD80 and CD86), adhesion molecules (CD54, CD58, and CD70), HLA molecules (Class I and HLA-DR) and the Fas death receptor (CD95) on the surface of the tumor cell. Additionally, CD40L-modified T-cells induced maturation and stimulated secretion of the pro-inflammatory cytokine IL-12 by monocyte derived dendritic cells. Finally, tumor targeted CAR/CD40L T-cells increased cytotoxicity against CD40+ tumors and extended the survival of tumor bearing mice in a xenotransplant model of systemic lymphoma. These pre-clinical data support the clinical application of CAR T-cells additionally modified to constitutively express CD40L with anticipated enhanced anti-tumor efficacy and improved clinical outcome.

Materials and Methods.

Cell Culture

DoHH2, Raji, and NALM-6 (American Type Culture Collection) tumor cell lines were maintained in RPMI 1640 medium (Gibco) supplemented with 10% heat inactivated fetal bovine serum (FBS), nonessential amino acids, sodium pyruvate, HEPES (N-2-hydroxyethylpiperazine-N'-2-ethanesulfonic acid) buffer, and 2-Mercaptoethanol (Invitrogen). The 293GP-GLV9 retroviral producer cell lines have been described previously and were cultured in DMEM (Invitrogen) supplemented with 10% FBS.[29] NIH-3T3 artificial antigen-presenting cells (AAPC) were cultured in DMEM supplemented with 10% heat-inactivated donor calf serum (DCS) as described previously.[30] Human T-cells were isolated from peripheral blood of healthy donors under Memorial Sloan-Kettering Cancer Center (MSKCC) IRB-approved protocol 95-054 using BD Vacutainer CPT tubes (Becton Dickinson) as per the manufacturer's instructions. Patient T-cell and CLL cells were obtained from patients undergoing treatment under MSKCC IRB-approved protocol 06-138 and isolated using Dynabeads ClinExVivo CD3/CD28 beads (Invitrogen). T-cells were cultured in RPMI 1640 supplemented with 10% FBS and 20 IU/mL IL-2 (R&D Systems). Monocyte derived dendritic cells (moDCs) were obtained from tissue culture plastic-adherent peripheral blood mononuclear cells (PBMCs) of healthy donors and cultured in RPMI 1640 supplemented with 1% pooled human A/B serum, HEPES buffer, 2-Mercaptoethanol (Invitrogen), interlukin-4 (IL-4; 500 IU/ml—R&D Systems) and granulocyte-monocyte colony-stimulating factor (GM-CSF; 1000 IU/ml—R&D Systems) as previously described.[31] All media were supplemented with 2 mmol/L L-glutamine (Invitrogen), 100 units/mL penicillin, and 100 µg/ml streptomycin (Invitrogen)

Construction of Retroviral Constructs

Figure 22A:
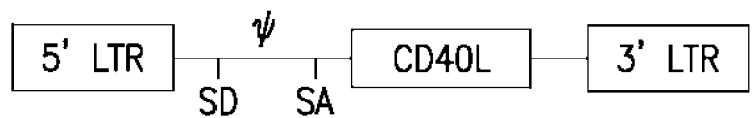
FIG. 22A-22D depict constitutive expression of CD40L by human T-cells. (A) Schematic of retroviral construct encoding human CD40L vector; LTR, long terminal repeat; SD, SA, splice donor and acceptor; Ψ, packaging element. (B) Flow cytometry of CD4+ and CD8+ CD40L-modified T-cells following retroviral gene transfer; x-axis APC-conjugated anti-human CD40L (CD154). (C) Enhanced proliferation of CD40L-modified T-cells compared to mock transduced T-cells. (D) Enhanced secretion of soluble CD40L (sCD40L), IFN-γ, and GM-CSF of CD40L-modified T-cells compared to mock transduced T-cells. All results are representative of at least three separate experiments. (* denotes statistical significance)

Human CD40L cDNA was PCR amplified from isolated healthy donor PBMCs using the following primers (1) 5'-CACGTGCATGATCGAAACATACAAC-CAAACTTCTCCCCGATCTGC-'3 [SEQ ID NO: 3] and (2) 5'-CTCGAGGGATCCTCAGAGTTTGAGTAAGC-CAAAGGA-3' [SEQ ID NO:4] (FIG. 22A). A gamma-retroviral vector encoding human CD40L was constructed using the SFG vector backbone.[32] Construction of 1928z and Pz1 (anti-prostate specific membrane antigen CAR; anti-PSMA) SFG-vector has been previously described.[33,34] Construction of 1928z-IRES-40L and Pz1-IRES-40L gamma-retroviral vector was generated using overlapping PCR (FIG. 26A).[35]

Retroviral Transduction of Human T-Lymphocytes

Generation of stable 293GP-GLV9 retroviral producer cell lines and genetic modification of human T-cells has been previously described.[29,36] For T-cell transduction isolated healthy donor PBMCs were activated with phytohemagglutinin (PHA) at 2 µg/mL (Sigma), whereas patient derived T-cells were isolated, activated, and expanded using Dynabeads ClinExVivo CD3/CD28 beads following the manufacturer's recommendations. Activated T-cells were retrovirally transduced on retronectin-coated non-tissue culture treated plates as previously described.[36] Gene transfer was assessed on day 7 by flow cytometry. Control mock-transduced T-cells were generated in the same manner except supernatant was derived from empty 293GP-GLV9 cell cultures. Proliferation of CD40L-modified T-cells was assessed by the Guava® easyCyte™ cell counter with Guava® ViaCount reagent (EMD Millipore) as per manufacturer's instructions. Expansion of modified T-cells for in vivo experiments was performed using AAPCs derived from NIH-3T3 murine fibroblast genetically engineered to express the target antigen (CD19 or PSMA) along with co-stimulation (CD80) as previously described.[30]

Co-Culture Assays

Tumor cells (DOHH2, Raji, Ph$^+$ ALL 3.1, NALM-6) were co-cultured at a ratio of 5:1 with CD40L-modified T-cells and mock-transduced T-cells. Flow cytometry was performed after three days to determine phenotype of tumor cells. moDCs ($2.5 \times 10^5$) were co-cultured with autologous CD40L-modified T-cells or mock-transduced T-cells at a 1:5 ratio and tissue culture supernatant was analyzed after 24 hours for IL-12p70 on a Luminex IS100 system (see below). moDCs were also co-cultured at a ratio of 5:1 with CD40L-modified T-cells and mock-transduced T-cells and phenotype of moDC was analyzed by flow cytometry 24 hours later.

Cytotoxicity Assay

The cytolytic capacity of transduced T-cells was determined using standard $^{51}$Cr release assay as previously described.[34]

Cytokine Detection Assays

Cytokine detection in tissue culture supernatant was assessed using the MILLIPLEX Human Cytokine Detection System (Millipore Corp.) in conjunction with the Luminex IS100 system and IS 2.3 software (Luminex Corp.) as per manufacturer's instructions.

Flow Cytometry

Flow cytometry was performed using a FACScan cytometer and data analyzed using FlowJo version 9.2 software (Tree Star). CAR expression was detected using CAR specific Armenian hamster monoclonal antibody 19E3 (1928z) and 12D11 (1928z and Pz1, MSKCC monoclonal antibody facility). CD40L expression was detected using mouse anti-human CD154 (BD Biosciences). Human T-cells were stained with mouse anti-human CD3 (BD Biosciences), CD4, and CD8 (Invitrogen). moDCs were stained using mouse anti-human CD11b, HLA-DR, CD83, and CD86 (Invitrogen). DOHH2, Raji, and NALM6 tumor cell phenotype was detected using mouse anti-human CD19, CD40, CD54, CD80 CD86, HLA-Class I and HLA-DR (Invitrogen), CD58, CD70, and CD95 (BD Biosciences).

CAR T-Cell In Vivo Studies

We inoculated 8 to 12 week-old SCID/Beige (CB17.Cg-Prkdc$^{scid}$Lyst$^{bg-J}$/Crl) mice (Charles River Laboratories) with DOHH2 tumor cells ($5 \times 10^5$ cells) by intravenous injection. Two days later mice were infused intravenously with transduced T-cells ($1 \times 10^7$ CAR T-cells). Tumor progression was monitored clinically and mice were euthanized when disease became clinically evident (development of hind limb paralysis or decreased response to stimuli). All murine studies were done in accordance with a Memorial Sloan-Kettering Cancer Center Institutional Animal Care and Use Committee approved protocol (00-05-065).

Statistical Analysis

All analyses were calculated using Graphpad Prism 5.0 software, survival data were assessed using a log-rank analysis and all other analyses were achieved with a Mann-Whitney test (one-tailed).

Results Constitutive Expression of CD40L by Human T-Cells

Figure 22B:
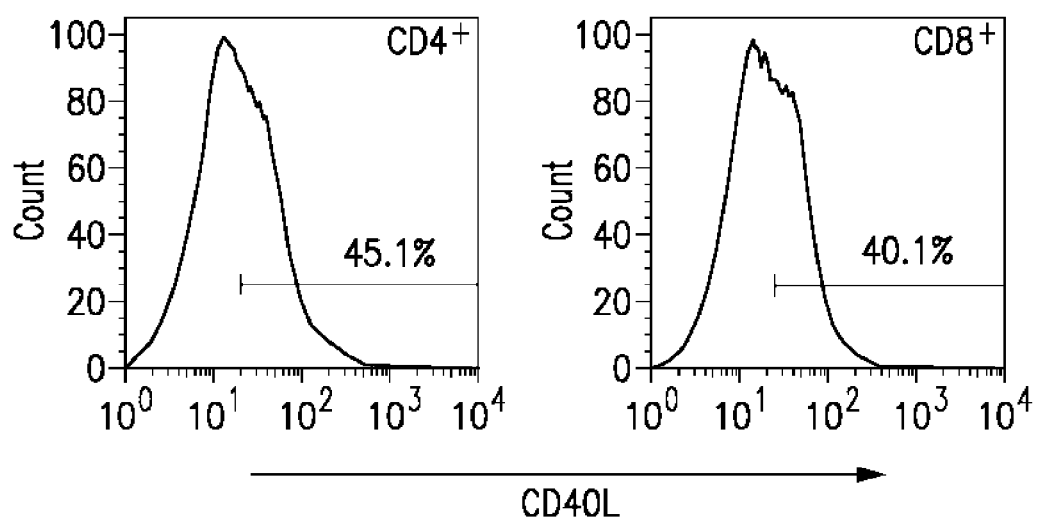
Figure 22C:
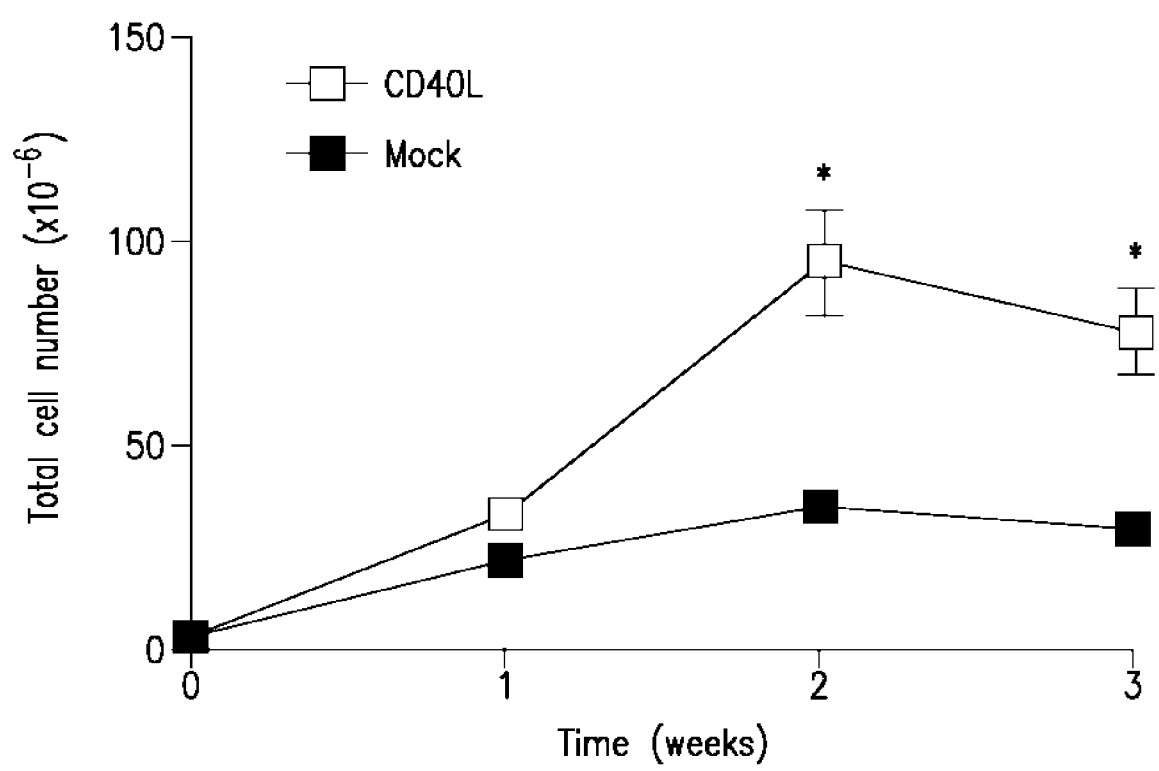
Figure 22D:
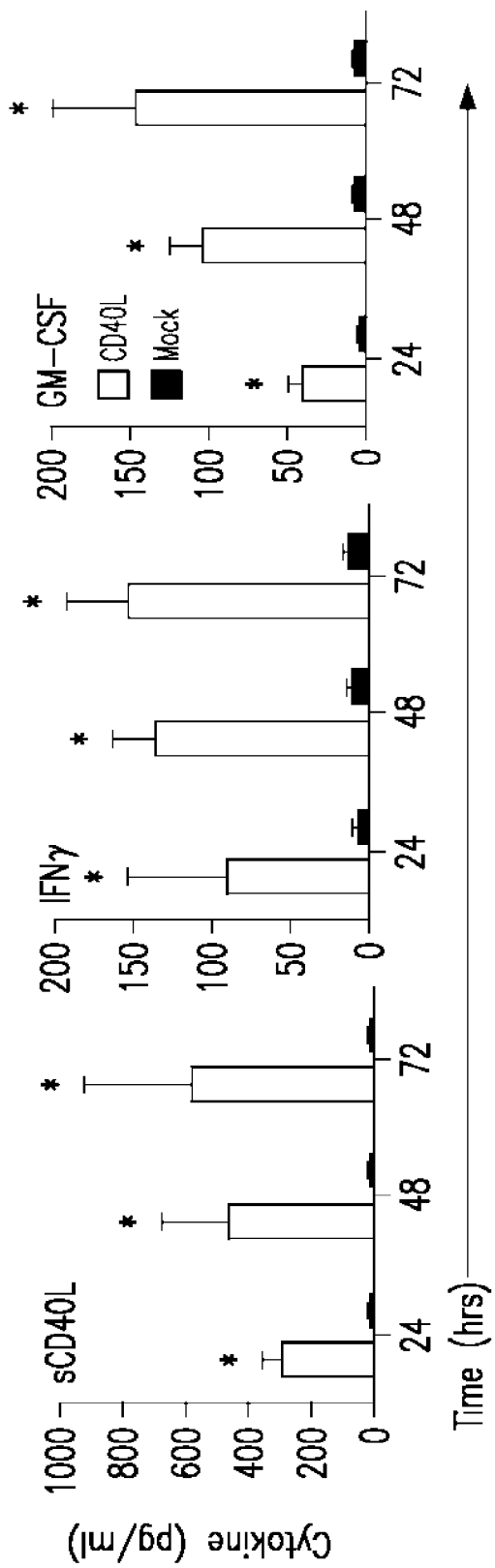

We initially transduced T-cells from healthy donor with a CD40L retroviral vector (FIG. 22A). Retroviral transduction of T-cells with the CD40L gene routinely resulted in ≥40% gene transfer with stable expression of CD40L in both CD4+ and CD8+ T-cell subsets (FIG. 22B). Proliferation of CD40L-modified T-cells was significantly increased compared to mock-transduced T-cells generated from the same three donors (FIG. 22C). Tissue culture media from CD40L-modified T-cells was analyzed and shown to have significantly increased soluble CD40L (sCD40L) as expected, as well as significantly increased secretion of the pro-inflammatory cytokines IFN-γ and GM-CSF when compared to the mock-transduced T-cells (FIG. 22D).

Figure 23A:
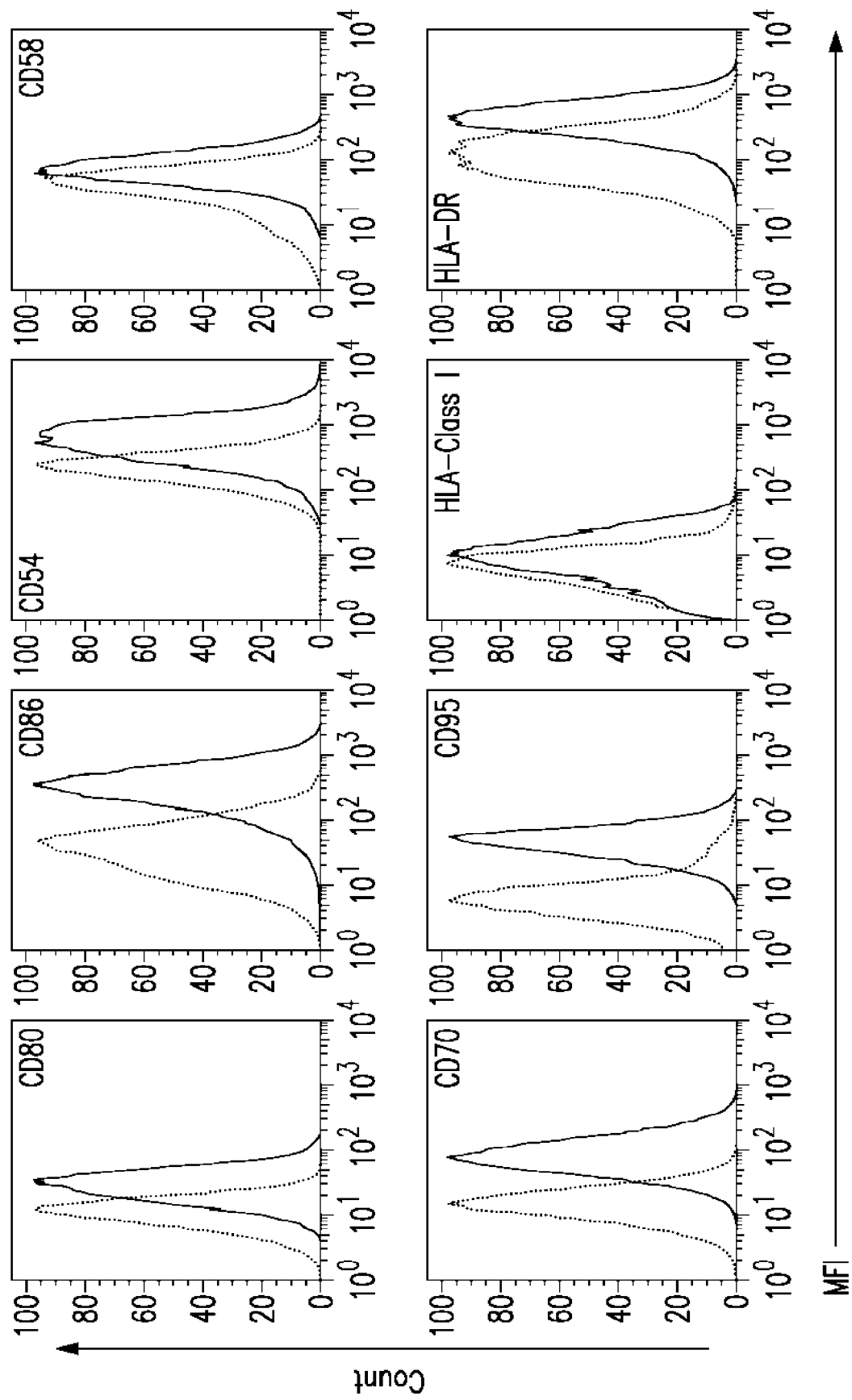
FIGS. 23A and 23 B depict augmented immunogenicity of CD40+ Tumor cells by CD40L-modified T-cells. (A) Flow cytometry showing upregulation of co-stimulatory molecules (CD80 and CD86), adhesion molecules (CD54, CD58, and CD70) HLA molecules (HLA Class I and HLA-DR), and the Fas-death receptor (CD95) on DOHH2 tumor cell line following co-culture with CD40L-modified T-cells (solid line) compared to culture with mock-transduced T-cells from the same donor (gray line). (B) CD40-tumor (NALM6 shown) demonstrating no phenotypic changes following co-culture with CD40L-modified T-cells. All results are representative of at least three separate experiments.
Figure 23B:
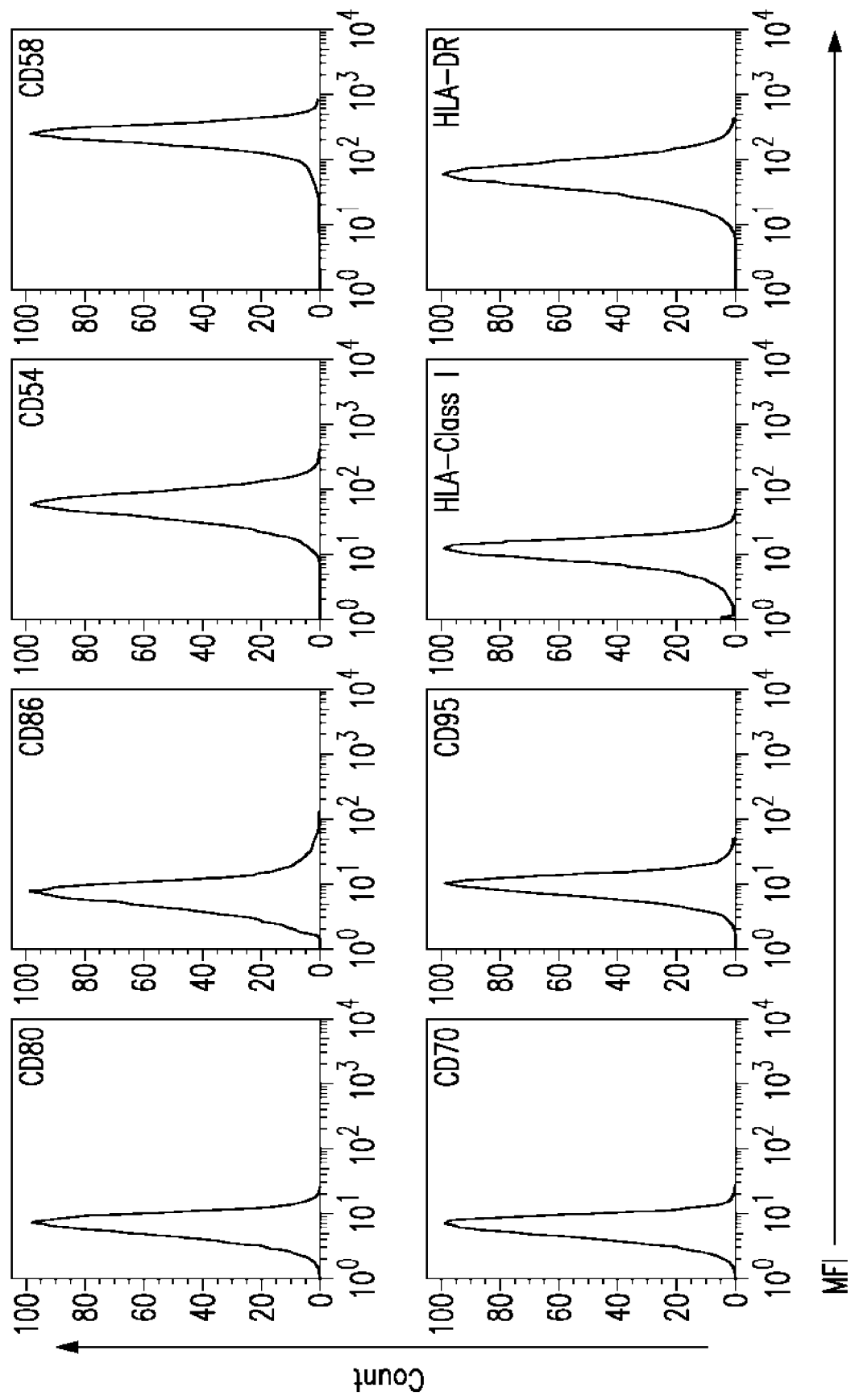
Figure 28:
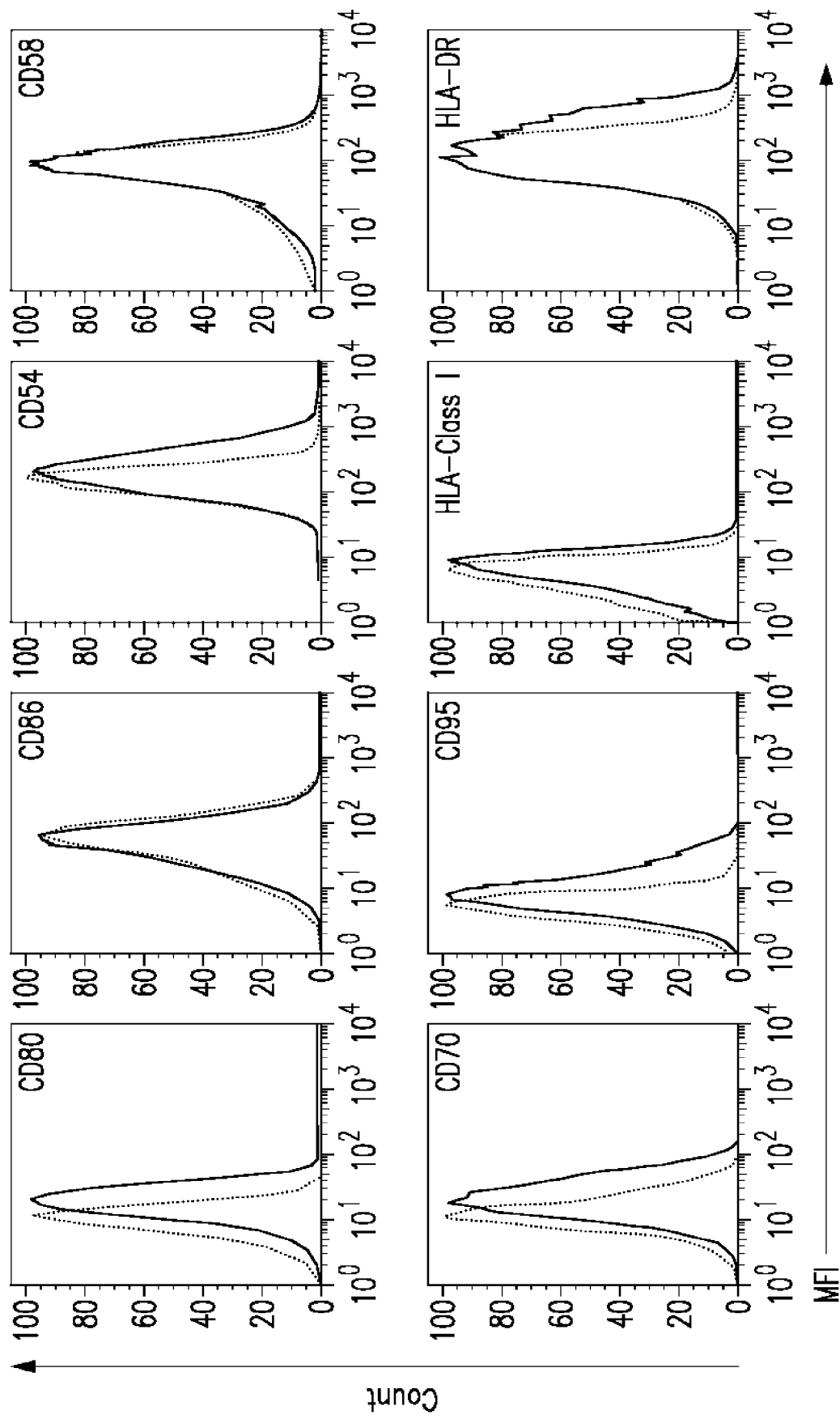
FIG. 28 depicts augmented immunogenicity of CD40+ Tumor cells by sCD40L. (A) Flow cytometry showing upregulation of co-stimulatory molecule (CD80), adhesion molecules (CD54, CD58, and CD70) HLA molecules (HLA Class I and HLA-DR), and the Fas-death receptor on DOHH2 tumor cell line following co-culture with conditioned media (CD40L-modified T-cells media) containing elevated levels of sCD40L (solid line) compared to media (mock-transduced T-cells media) without elevated levels of sCD40L (gray line).

CD40L-Modified T-Cells Alter the Phenotype of Both CD40+ Tumor Cell Lines and Patient Derived CLL Cells To investigate the ability of the CD40L/CD40 pathway to modify the phenotype of tumor cells a co-culture of CD40+ B-cell tumor cells and CD40L-modified T-cells or mock-transduced T-cells was performed. Cultures with CD40L-modified T-cells, but not mock-transduced T-cells, led to the upregulation of co-stimulatory molecules (CD80 and CD86), adhesion molecules (CD54, CD58, and CD70), HLA molecules (HLA Class I and HLA-DR), and the Fas death receptor (CD95) on the surface of DOHH2 tumor cells (FIG. 23A). Phenotypic changes are also evident when DOHH2 tumor cells are cultured in conditioned media from CD40L-modified T cell which contains elevated levels of sCD40L (FIG. 28). To determine if CD40 expression on the tumor cell is a requisite to alter tumor cell phenotype co-culture of the CD40-tumor cell line (NALM6) with CD40L-modified T-cells and mock-transduced T-cells was performed. These studies resulted in no alteration in the phenotype demonstrating the need for CD40 expression by the tumor to induce CD40L mediated changes in tumor cell phenotype (FIG. 23B).

Figure 24A:
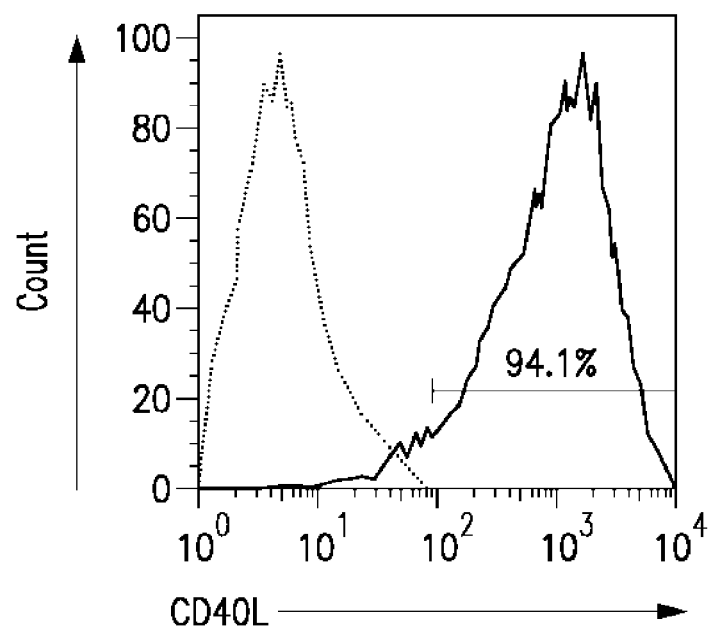
FIGS. 24A and 24B depict augmented immunogenicity of CLL cells by autologous CD40L-modified T-cells. (A) Flow cytometry of patient derived CD40L-modified T-cells following retroviral gene transfer with CD40L containing retroviral vector; x-axis APC-conjugated anti-human CD40L (CD154). (B) Flow cytometry showing upregulation of co-stimulatory molecules (CD80 and CD86), adhesion molecules (CD54, CD58, and CD70) HLA molecules (HLA Class I and HLA-DR), and the Fas-death receptor (CD95) on CLL cells after co-culturing with autologous CD40L-modified T-cells (solid line) compared to co-cultures with mock-transduced T-cells from the same donor (gray line). All results are representative of at least three separate experiments.
Figure 24B:
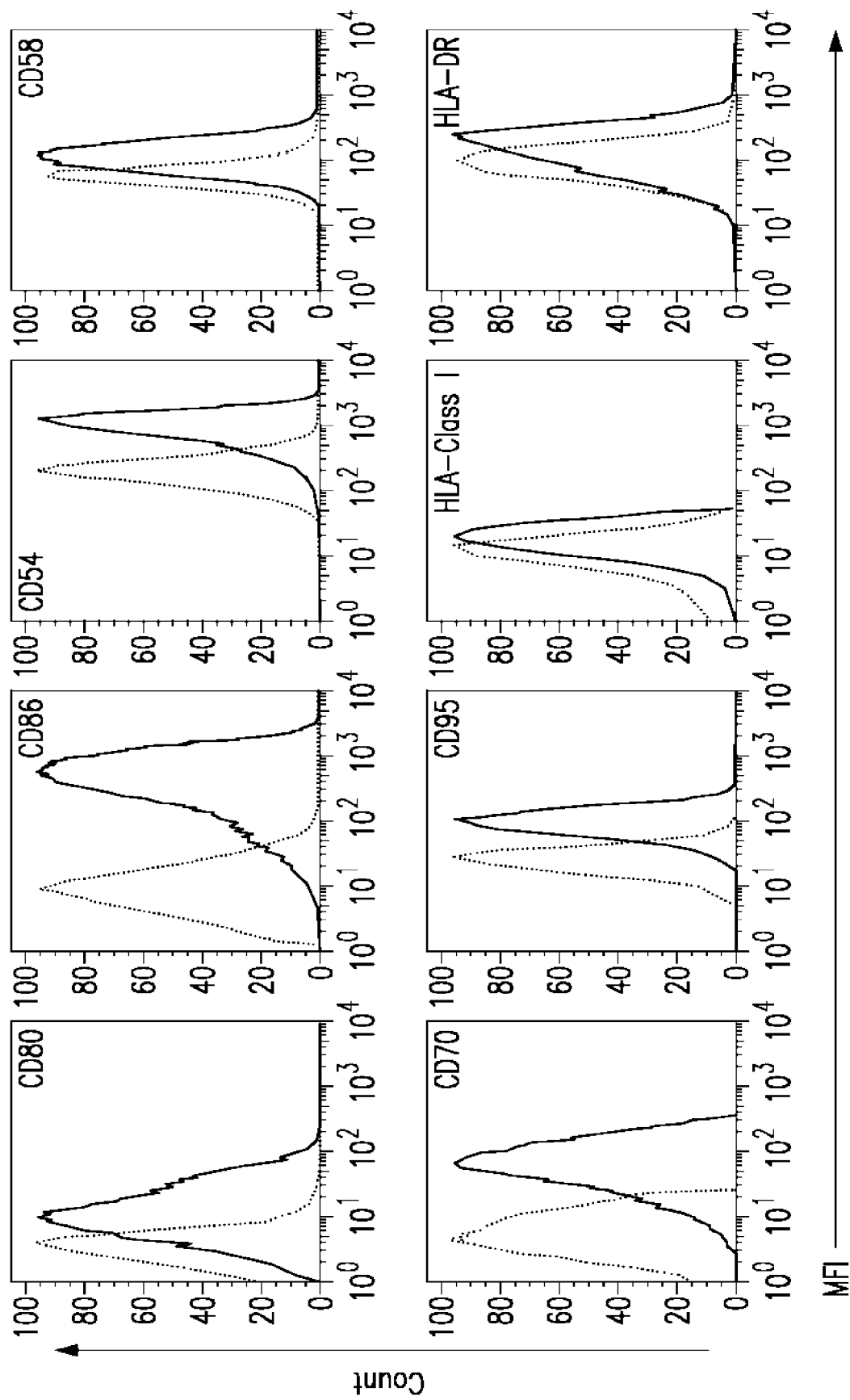

To further verify this effect in a clinically relevant setting we co-cultured CD40L-modified T-cells derived from patients with CLL with autologous CLL tumor cells. Retroviral transduction of CLL patient derived T-cells routinely resulted in ≥40% gene transfer with stable expression of the CD40L gene (FIG. 24A). In this setting patient derived CD40L-modified T-cells, but not mock-transduced T-cells, demonstrated the capacity to upregulate co-stimulatory molecules, adhesion molecules, HLA molecules and the Fas death receptor on the surface of the autologous CLL cells (FIG. 24B).

Figure 25A:
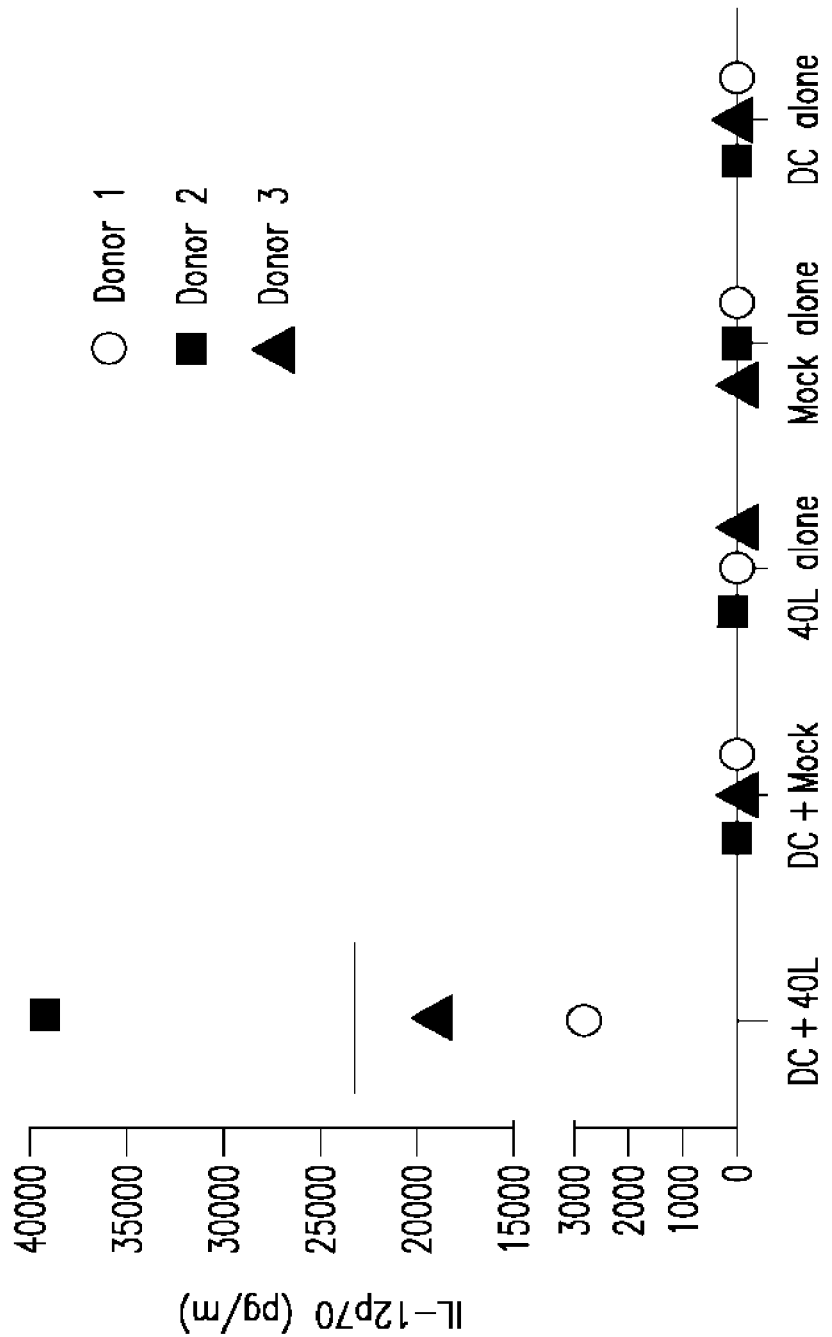
FIGS. 25A and 25B depict secretion of IL-12 and maturation of monocyte derived Dendritic Cells (moDCs) by CD40L-modified T-cells. (A) Cytokine analysis of culture media for co-cultures (24 hours) between moDCs and CD40L-modified T-cells from three separate donors demonstrating elevated IL-12p70 secretion. (B) Flow cytometry of moDCs demonstrating maturation following co-culture with CD40L-modified T-cells. All results are representative of at least three experiments.
Figure 25B:
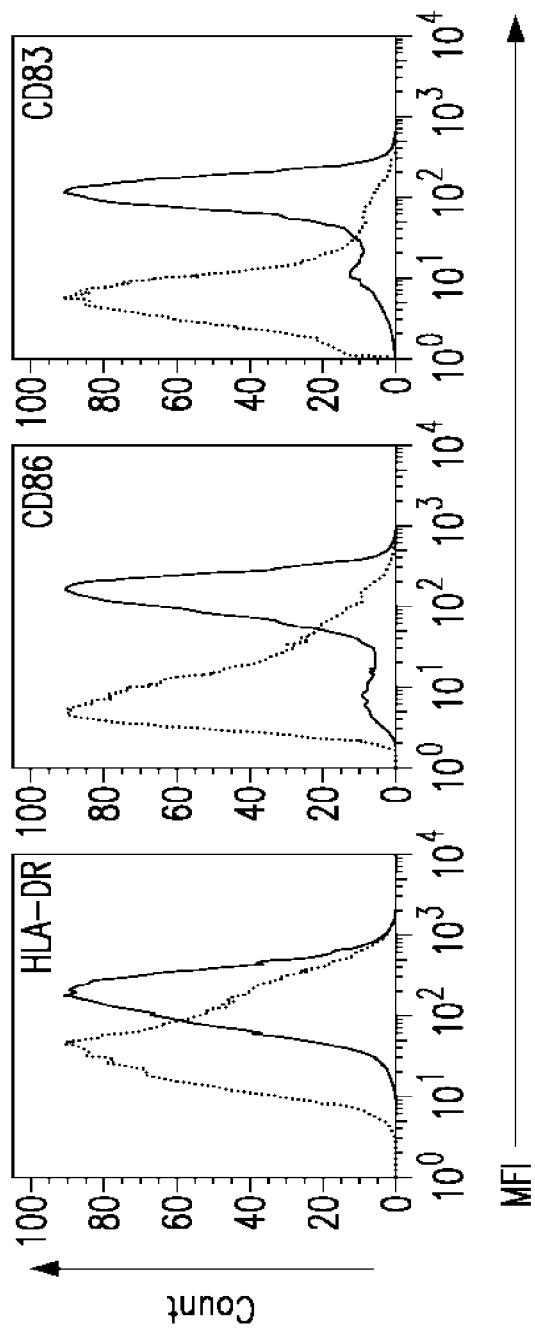

CD40L-Modified T-Cells Induce IL-12p70 Secretion and Mediate Maturation of moDCs Given the role of CD40L in DC maturation and secretion of the pro-inflammatory cytokine IL-12 we next investigated if CD40L-modified T-cells could induce the same effect when co-cultured with autologous moDCs. Significantly, we found CD40L-modified T-cell induced secretion of IL-12p70 in the co-cultures containing moDCs and autologous CD40L-modified T-cells from three separate donors (FIG. 25A). Maturation of moDCs as determined by upregulation of surface co-stimulatory molecules (HLA-DR, CD86, and CD83) was also seen following co-culture with CD40L-modified T-cells but not following co-culture with mock-transduced T-cells (FIG. 25B).

Figure 26A:
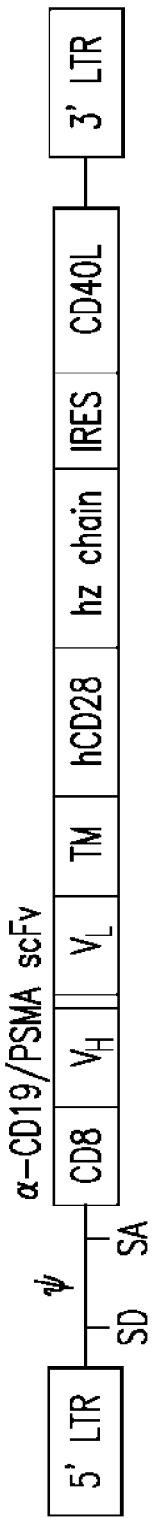
FIG. 26A-26C depict efficient transduction of human T-cells with a CAR/CD40L vector demonstrates enhanced cytotoxicity. (A) Schematic of retroviral construct containing 1928z-IRES-CD40L and Pz1-IRES-CD40L genes; LTR, long terminal repeat; SD, SA, splice donor and acceptor; Ψ, packaging element; CD8 indicates CD8 leader sequence; scFv, single chain variable fragment; VH and VL, variable heavy and light chains; TM, transmembrane domain. (B) FACS analysis of human T-cells transduced to express 19-28z/CD40L vector (pre-stimulation) with subsequent enhanced expression of CAR/CD40L following co-culture on AAPCs (NIH 3T3 fibroblasts expressing CD19 and CD80; 1928/CD40LT-cells shown) used for in vivo experiments. x-axis, PE-conjugated 1928z CAR-specific antibody (19e3); y-axis, APC-conjugated anti-human CD40L (CD154). (C) As determined by standard 51Cr release assay 19-28z/40L T-cells have significant increased ability to lyse DOHH2 tumor cells compared to 19-28z T-cells. All results are representative of at least three experiments. (* denotes statistical significance).
Figure 26B:
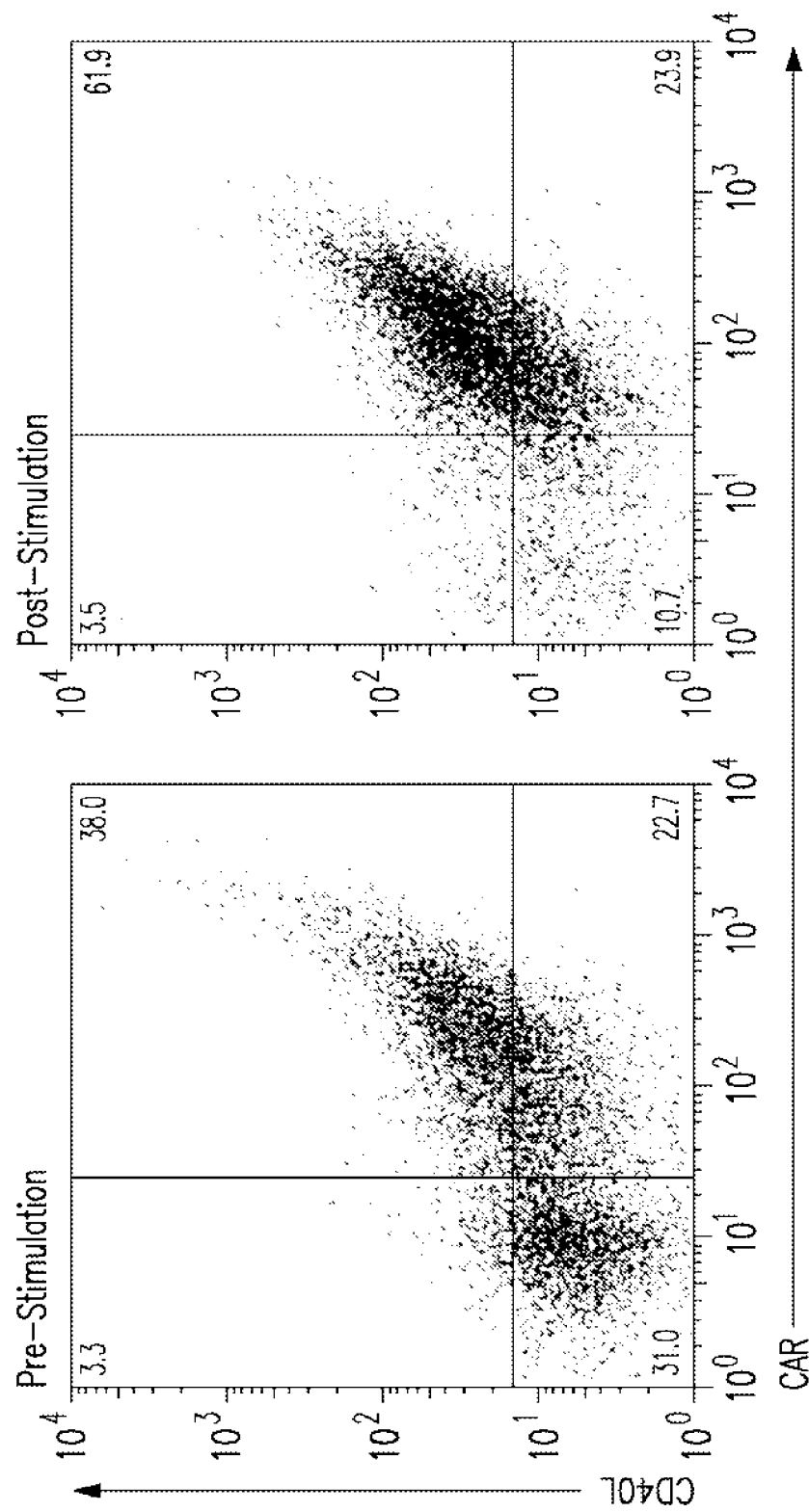
Figure 26C:
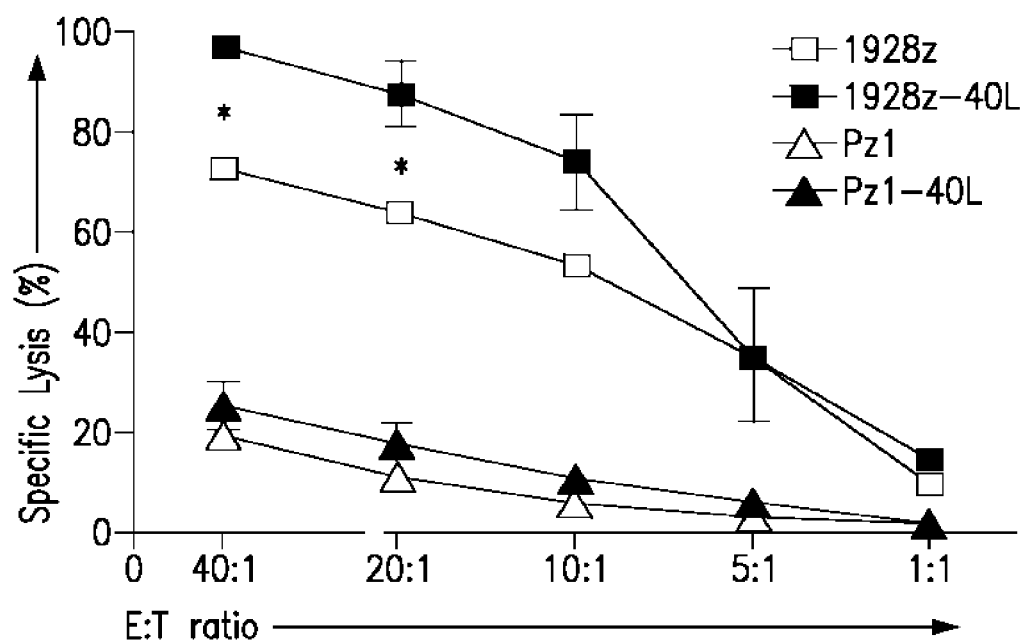
Figure 29:
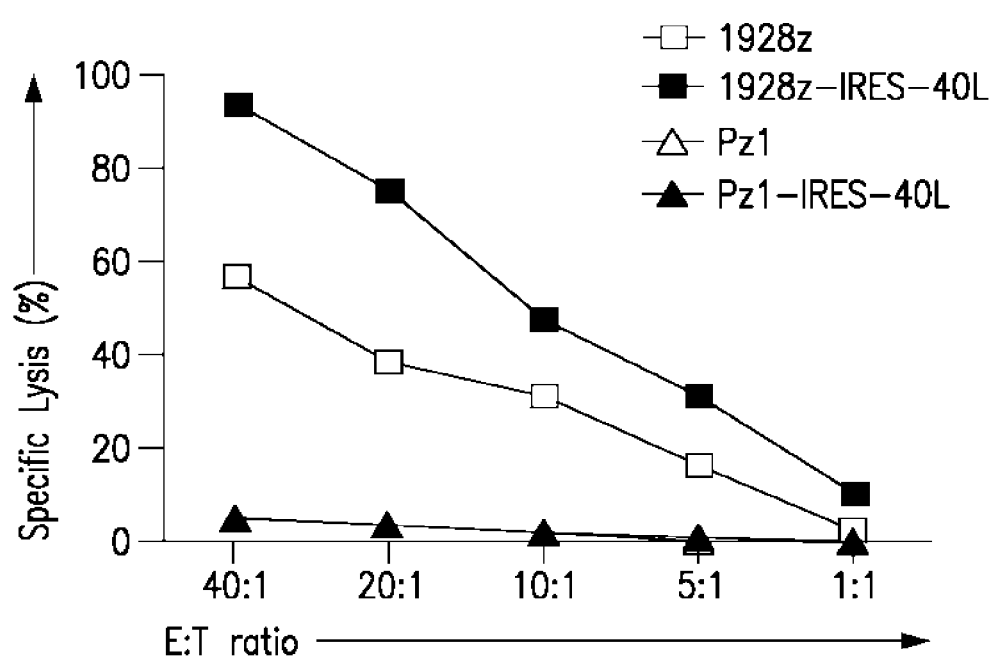
FIG. 29 depicts 1928z/CD40L T-cells demonstrates enhanced cytotoxicity. As determined by standard 51Cr release assay 19-28z/40L T-cells have significant increased ability to lyse Raji tumor cells compared to 19-28z T-cells.

Expression of Both CAR and CD40L by T-Cells Results in Enhanced In Vitro and In Vivo Cytotoxicity We next assessed the ability of T-cells to express both the anti-CD19 CAR (1928z) and CD40L using a bi-cistronic retroviral vector (1928z/CD40L; FIG. 26A). Transduction of T-cells routinely resulted in ≥40% expression of both 1928z and CD40L (1928z/CD40L T-cells; FIG. 26B). Control retroviral vectors were also generated including the anti-CD19 CAR (1928z) and anti-PSMA CAR (Pz1 and Pz1/CD40L; FIG. 26B). To assess in vitro anti-tumor activity of 1928z/CD40L T-cells, a standard 4 hour $^{51}$Cr release assay was performed. Constitutive expression of CD40L statistically enhanced the lytic capacity of 1928z T-cells against CD19+ tumor cells when compared to a panel of control T-cells including T cells modified to express the 1928z CAR alone (FIG. 26C). Enhanced cytotoxicity is also demonstrated against other CD19+/CD40+ tumor cell lines (FIG. 29).

Figure 27:
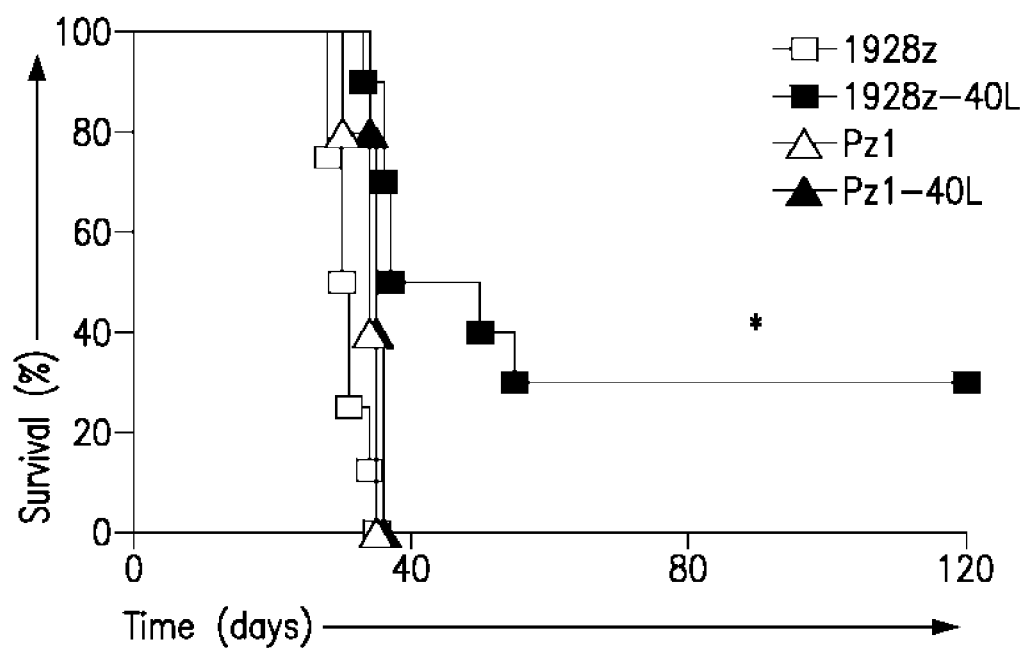
FIG. 27 depicts tumor eradication and long term survival following 1928z/CD40L T-cell infusion. Survival curve of SCID-Beige mice inoculated with DOHH2 tumor cells by intravenous (i.v.) injection 2 days before a single i.v. dose of CAR-modified T-cells. Enhanced long-term survival was demonstrated in mice treated with 1928z/CD40L T-cells (n=10) as compared to a panel of control T cells (1928z group n=8; Pz1 and Pz1/40L group n=5). Results are representative of at least two experiments. (* denotes statistical significance).

To investigate the in vivo antitumor activity of 1928z/CD40L T-cells we utilized a xenotransplant model of systemic DOHH2 lymphoma. We have previously observed that systemic DOHH2 tumor cells are markedly refractory to CD19-targeted CAR T-cell therapy in SCID/Beige mice. To assess whether further modification of CAR T-cells with CD40L could enhance the anti-tumor efficacy in this model we inoculated and treated SCID/Beige mice bearing systemic DOHH2 tumor with CAR/CD40L T-cells. Significantly, treatment with 1928z/CD40L T-cells compared to treatment with 1928z T-cells or control T-cells (Pz1 and Pz1/CD40L T-cells) demonstrated enhanced survival and resulted in long-term survival in 30% of mice treated with 1928z/40L T-cells (FIG. 27).

Discussion

Adoptive therapy utilizing CAR T-cells has shown promising clinical responses in patients with B-cell malignancies.[2-4] These studies have demonstrated the potency of CAR T-cells as the sole anti-tumor effector cell. However, this approach may have limited success against tumors with a robust immunosuppressive tumor microenvironment.[5] Furthermore, in their current form CAR T-cells have not demonstrated the ability respond to tumor escape following target antigen loss.[6] One possible method to overcome these limitations is to further engineer CAR T-cells through the constitutive expression of CD40L in effort to improve T-cell cytolytic capacity/proliferation, augment tumor immunogenicity, and improve DC antigen presentation/function. Modification of CAR T-cells through the constitutive expression of CD40L may also further activate an endogenous immune response thereby enhancing anti-tumor efficacy.

To assess the role of constitutive expression of CD40L by T-cells we first developed a retroviral vector containing the CD40L gene alone. When transduced in T-cells both constitutive expression of CD4+ and CD8+ T-cell subsets are demonstrated (FIG. 22B). While more commonly associated with CD4+ T-cells, CD40L expression and helper function in memory CD8+ T-cells has recently been reported.[37] CD40L expression is also known to enhance T-cell proliferation and secretion of pro-inflammatory TH1 cytokines (IFN-γ, GM-CSF).[21,22] CD40L-modified T-cells demonstrate the ability to secrete pro-inflammatory cytokines and enhanced proliferation as compared to similarly activated but mock transduced T-cells from the same donor (FIGS. 22C and 22D). Arming T-cells through the constitutive expression of CD40L has the potential to enhance their anti-tumor function/activation.

Figure 2A:
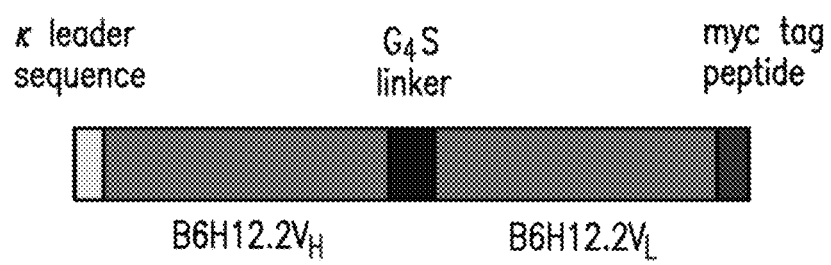
FIGS. 2A and 2B depict the structure of secretable anti-CD47 scFv constructs.
Figure 2B:
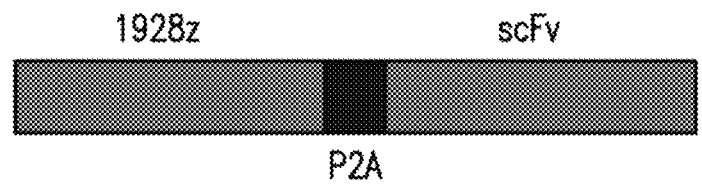

The downregulation of cell surface proteins including HLA Class I, co-stimulatory molecules and/or adhesion molecules is often employed by tumors to avoid immune recognition.[5,38,39] Apoptotic resistance can also occur with the loss of the Fas death receptor on the surface of malignant cells.[40] To counteract this, CD40L can interact with CD40 on malignant cells to mediate the up-regulation of co-stimulatory molecules (CD80 and CD86), adhesion molecules (CD54, CD58, and CD70), HLA molecules (HLA Class I and HLA-DR) and facilitate apoptosis through the Fas/FasL pathway on malignant B-cell tumors.[41,42] CD40L-modified T-cells modified the phenotype of CD40+ tumor cells resulting in the upregulation of these critical surface proteins thereby counteracting the tumor cells' ability for immune evasion (FIG. 2). This effect was dependent on the expression of CD40 by the tumor cells as the phenotypic changes were absent when CD40-tumor cells were co-cultured with CD40L-modified T-cells (FIG. 23A-B). This effect was also seen in a more clinically relevant setting in which co-cultured CD40L-modified T-cells derived from CLL patients augmented the immunogenicity of autologous CLL cells (FIG. 24A-B). This finding demonstrates the retained ability of T-cells to augment the immunogenicity of autologous malignant cells through constitutive CD40L expression. Importantly, cell to cell contact is not a requisite to modify the tumor cell phenotype as media containing elevated levels of sCD40L led to similar phenotypic changes (FIG. 28). Augmenting the immunogenicity of cancer cells through the CD40L/CD40 pathway has been shown to induce an endogenous anti-tumor response in previously published vaccine studies using the infusion of autologous CLL tumor cells transduced with an adenovirus vector encoding CD40L (Ad-CD40L CLL cells).[27,28] Infusion of tumor-specific T cells further modified to constitutively express CD40L could also have a similar capacity to induce an endogenous anti-tumor response. This may result in epitope spreading through the recruitment of an endogenous anti-tumor T or NK cell thereby limiting the ability of tumor escape through the downregulation of a single target antigen.

Dendritic cell (DC) function is impeded within the tumor microenvironment. Normally DCs mature, migrate and present antigen within lymph nodes thereby stimulating the adaptive arm of the immune system to the presence of malignancy or pathogen.[5] However, DC's exposed to the suppressive tumor microenvironment have a paradoxical function of inducing $T_{regs}$ and tolerizing tumor-specific T-cells.[43] To counteract this, the CD40L/CD40 pathway can boost DCs antigen presentation, production of the pro-inflammatory cytokine IL-12, and promote CD8+ T-cell cytotoxic function.[19,20] Agonist CD40 antibodies have previously been shown to activate DCs and boost CD8+ T-cell response thereby replacing the need for CD4+ T-cell help.[26] Furthermore, CD40L-modified tumor-specific CD8+ T-cells have been shown to stimulate the maturation of DCs and augment the anti-tumor responses of adoptively transferred CD8+ T-cells in tumor bearing mice.[44] To test the ability of CD40L-modified T-cells to augment the function of human DCs, an in-vitro co-culturing experiment with autologous moDCs was used. Significantly CD40L-modified T-cells stimulated the secretion of IL-12p70 from moDCs (FIG. 25A-B). IL-12 is a pleiotropic cytokine with several immune-stimulatory functions including the ability to enhance T-cell proliferation, cytotoxic capacity, and mediate resistance to Treg suppression as we and others have previously shown.[7,45] The ability of CAR/40L T-cells to stimulate IL-12 production from DCs may translate into an improved anti-tumor effect of adoptively transferred CAR T-cells as well as recruitment and activation of endogenous tumor specific T-cells and natural killer (NK) cells. By promoting IL-12 production in close proximity to the tumor we anticipate minimal IL-12 related toxicity in contrast to prior studies showing severe toxicity following systemic IL-12 administration. In addition to stimulating IL-12 production, CD40L-modified T-cells promote DC maturation which in the context of CAR T-cell cytotoxicity should further enhance DC tumor antigen uptake and presentation resulting in recruitment/activation of an endogenous anti-tumor response by effector T-cells and NK cells (FIG. 25A-B). Taken together enhanced DC function should translate into enhanced anti-tumor efficacy of genetically modified tumor specific T-cells through recruitment of an endogenous anti-tumor immune response.

The ability of CAR T-cells to redirect the specificity of T-cells has been the demonstrated in a number of pre-clinical and clinical reports.[1] We developed a retroviral vector containing the anti-CD19 CAR (1928z) and the CD40L gene (FIG. 28A). Constitutive expression of both 1928z and CD40L by T-cells is readily achievable (FIG. 28B). Significantly when testing the cytotoxic potential of 1928z/40L T-cells against a panel of CD19+ targets we noted increased cytotoxicity compared to T-cells modified with the 1928z CAR alone (FIG. 28C). Recently, Laurin and colleagues reported enhanced cytotoxicity by CAR T-cells against tumor cell lines following CD40/IL-4 dependent upregulation of surface adhesion molecules which could also explain the increased cytotoxicity seen in our experiments.[46] To test the in vivo potential of CAR/CD40L T-cells a xenotransplant model using the aggressive transformed follicular lymphoma cell line DOHH2 was used. This model has been historically resistant to eradiation by 1928z T-cells (FIG. 27). However, with the added modification of CD40L our 1928z/CD40L T-cells extend the survival of tumor bearing mice when compared to mice treated with 1928z T-cells alone and result in 30% long-term survival in the 1928z/CD40L T-cell treated group (FIG. 27). While this model demonstrates a survival difference, the lack of a competent immune system by SCID/Beige mice makes this model unsuitable to investigate the full benefit which constitutive CD40L expression by CAR T-cells may have in eradicating established tumors. While we observe enhanced anti-tumor efficacy in our model, this is likely related to enhanced cytotoxicity of CAR T-cells by an autocrine/paracrine CD40/CD40L pathway, and not through the recruitment/activation of an endogenous immune response by CD40L-modified CAR T-cells. An immune-competent syngeneic tumor model may be used to investigate the full effect of constitutive expression of CD40L by CAR T cells on the tumor microenvironment and recruitment of endogenous anti-tumor immune responses. An immune-competent syngeneic model of human CD19+ B-cell malignancy has recently been developed and is being utilized to assess 1928z/CD40L T-cells in the context of a competent immune system.

The constitutive expression of CD40L on bone marrow or thymic cells has been shown to result in T-lymphoproliferative disorders following infusion into CD40L-deficient mice.[47] The clonal populations which arose within the thymus following unremitting CD40L stimulation of thymocytes may have led to malignant transformation (rather than the insertional oncogenesis of CD40L-modified cells). While we have noted minimal toxicity and the absence of malignant transformation following infusion of CAR/CD40L T-cells, given the concerns regarding malignant T-cell transformation, an effective suicide gene, such as iCasp9, may be desirably included within the retroviral vector.[48]

REFERENCES FOR EXAMPLE 6

1. Curran K J, Pegram H J, Brentjens R J. Chimeric antigen receptors for T cell immunotherapy: current understanding and future directions. J Gene Med. 2012; 14(6):405-415.
2. Brentjens R J, Davila M L, Riviere I, et al. CD19-Targeted T Cells Rapidly Induce Molecular Remissions in Adults with Chemotherapy-Refractory Acute Lymphoblastic Leukemia. Sci Transl Med. 2013; 5(177):177ra138.
3. Brentjens R J, Riviere I, Park J H, et al. Safety and persistence of adoptively transferred autologous CD19-targeted T cells in patients with relapsed or chemotherapy refractory B-cell leukemias. Blood. 2011; 118(18):4817-4828.
4. Porter D L, Levine B L, Kalos M, Bagg A, June C H. Chimeric antigen receptor-modified T cells in chronic lymphoid leukemia. N Engl J Med. 2011; 365(8):725-733.
5. Vesely M D, Kershaw M H, Schreiber R D, Smyth M J. Natural innate and adaptive immunity to cancer. Annu Rev Immunol. 2011; 29:235-271.
6. Grupp S A, Kalos M, Barrett D, et al. Chimeric antigen receptor-modified T cells for acute lymphoid leukemia. N Engl J Med. 2013; 368(16):1509-1518.
7. Pegram H J, Lee J C, Hayman E G, et al. Tumor-targeted T cells modified to secrete IL-12 eradicate systemic tumors without need for prior conditioning. Blood. 2012; 119(18):4133-4141.
8. Armitage R J, Fanslow W C, Strockbine L, et al. Molecular and biological characterization of a murine ligand for CD40. Nature. 1992; 357(6373):80-82.
9. Schonbeck U, Libby P. The CD40/CD154 receptor/ligand dyad. Cell Mol Life Sci. 2001; 58(1):4-43.
10. Uckun F M, Gajl-Peczalska K, Myers D E, Jaszcz W, Haissig S, Ledbetter J A. Temporal association of CD40 antigen expression with discrete stages of human B-cell ontogeny and the efficacy of anti-CD40 immunotoxins against clonogenic B-lineage acute lymphoblastic leukemia as well as B-lineage non-Hodgkin's lymphoma cells. Blood. 1990; 76(12):2449-2456.
11. Gruss H J, Ulrich D, Braddy S, Armitage R J, Dower S K. Recombinant CD30 ligand and CD40 ligand share common biological activities on Hodgkin and Reed-Sternberg cells. Eur J Immunol. 1995; 25(7):2083-2089.
12. Zong Y S, Lin H, Choy D T, et al. Nasopharyngeal carcinoma and lymphoinfiltration. Oncology. 1991; 48(4): 290-296.
13. Lollini P L, Landuzzi L, Frabetti F, et al. Expression of functional CD40 on human osteosarcoma and Ewing's sarcoma cells. Clin Cancer Res. 1998; 4(8):1843-1849.
14. van den Oord J J, Maes A, Stas M, et al. CD40 is a prognostic marker in primary cutaneous malignant melanoma. Am J Pathol. 1996; 149(6):1953-1961.
15. Wingett D G, Vestal R E, Forcier K, Hadjokas N, Nielson C P. CD40 is functionally expressed on human breast carcinomas: variable inducibility by cytokines and enhancement of Fas-mediated apoptosis. Breast Cancer Res Treat. 1998; 50(1):27-36.
16. Ciaravino G, Bhat M, Manbeian C A, Teng N N. Differential expression of CD40 and CD95 in ovarian carcinoma. Eur J Gynaecol Oncol. 2004; 25(1):27-32.
17. Altenburg A, Baldus S E, Smola H, Pfister H, Hess S. CD40 ligand-CD40 interaction induces chemokines in cervical carcinoma cells in synergism with IFN-gamma. J Immunol. 1999; 162(7):4140-4147.
18. Grewal I S, Flavell R A. CD40 and CD154 in cell-mediated immunity. Annu Rev Immunol. 1998; 16:111-135.
19. Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med. 1996; 184(2): 747-752.
20. Clarke S R. The critical role of CD40/CD40L in the CD4-dependent generation of CD8+ T cell immunity. J Leukoc Biol. 2000; 67(5):607-614.
21. Cayabyab M, Phillips J H, Lanier L L. CD40 preferentially costimulates activation of CD4+ T lymphocytes. J Immunol. 1994; 152(4):1523-1531.
22. Peng X, Kasran A, Warmerdam P A, de Boer M, Ceuppens J L. Accessory signaling by CD40 for T cell activation: induction of Th1 and Th2 cytokines and synergy with interleukin-12 for interferon-gamma production. Eur J Immunol. 1996; 26(7):1621-1627.
23. Bhadra R, Gigley J P, Khan I A. Cutting edge: CD40-CD40 ligand pathway plays a critical CD8-intrinsic and -extrinsic role during rescue of exhausted CD8 T cells. J Immunol. 2011; 187(9):4421-4425.
24. Bourgeois C, Rocha B, Tanchot C. A role for CD40 expression on CD8+ T cells in the generation of CD8+ T cell memory. Science. 2002; 297(5589):2060-2063.
25. Khong A, Nelson D J, Nowak A K, Lake R A, Robinson B W. The use of agonistic anti-CD40 therapy in treatments for cancer. Int Rev Immunol. 2012; 31(4):246-266.
26. Vonderheide R H, Glennie M J. Agonistic CD40 antibodies and cancer therapy. Clin Cancer Res. 2013; 19(5): 1035-1043.
27. Wierda W G, Cantwell M J, Woods S J, Rassenti L Z, Prussak C E, Kipps T J. CD40-ligand (CD154) gene therapy for chronic lymphocytic leukemia. Blood. 2000; 96(9):2917-2924.
28. Wierda W G, Castro J E, Aguillon R, et al. A phase I study of immune gene therapy for patients with CLL using a membrane-stable, humanized CD154. Leukemia. 2010; 24(11):1893-1900.
29. Ghani K, Wang X, de Campos-Lima P O, et al. Efficient human hematopoietic cell transduction using RD114- and GALV-pseudotyped retroviral vectors produced in suspension and serum-free media. Hum Gene Ther. 2009; 20(9):966-974.
30. Brentjens R J, Latouche J B, Santos E, et al. Eradication of systemic B-cell tumors by genetically targeted human T lymphocytes co-stimulated by CD80 and interleukin-15. Nat Med. 2003; 9(3):279-286.
31. Ratzinger G, Reagan J L, Heller G, Busam K J, Young J W. Differential CD52 expression by distinct myeloid dendritic cell subsets: implications for alemtuzumab activity at the level of antigen presentation in allogeneic graft-host interactions in transplantation. Blood. 2003; 101(4):1422-1429.
32. Riviere I, Brose K, Mulligan R C. Effects of retroviral vector design on expression of human adenosine deaminase in murine bone marrow transplant recipients engrafted with genetically modified cells. Proc Natl Acad Sci USA. 1995; 92(15):6733-6737.
33. Brentjens R J, Santos E, Nikhamin Y, et al. Genetically targeted T cells eradicate systemic acute lymphoblastic leukemia xenografts. Clin Cancer Res. 2007; 13(18 Pt 1):5426-5435.
34. Gong M C, Latouche J B, Krause A, Heston W D, Bander N H, Sadelain M. Cancer patient T cells genetically targeted to prostate-specific membrane antigen specifically lyse prostate cancer cells and release cytokines in response to prostate-specific membrane antigen. Neoplasia. 1999; 1(2):123-127.
35. Santos E B, Yeh R, Lee J, et al. Sensitive in vivo imaging of T cells using a membrane-bound *Gaussia princeps* luciferase. Nat Med. 2009; 15(3):338-344.
36. Quintas-Cardama A, Yeh R K, Hollyman D, et al. Multifactorial optimization of gammaretroviral gene transfer into human T lymphocytes for clinical application. Hum Gene Ther. 2007; 18(12):1253-1260.
37. Frentsch M, Stark R, Matzmohr N, et al. CD40L expression permits CD8+ T cells to execute immunologic helper functions. Blood. 2013; 122(3):405-412.
38. Greaves P, Gribben J G. The role of B7 family molecules in hematologic malignancy. Blood. 2013; 121(5):734-744.
39. Geijtenbeek T B, van Kooyk Y, van Vliet S J, Renes M R, Raymakers R A, Figdor C G. High frequency of adhesion defects in B-lineage acute lymphoblastic leukemia. Blood. 1999; 94(2):754-764.
40. Rieux-Laucat F, Le Deist F, Hivroz C, et al. Mutations in Fas associated with human lymphoproliferative syndrome and autoimmunity. Science. 1995; 268(5215): 1347-1349.
41. Schultze J L, Cardoso A A, Freeman G J, et al. Follicular lymphomas can be induced to present alloantigen efficiently: a conceptual model to improve their tumor immunogenicity. Proc Natl Acad Sci USA. 1995; 92(18):8200-8204.
42. Schattner E J, Mascarenhas J, Bishop J, et al. CD4+ T-cell induction of Fas-mediated apoptosis in Burkitt's lymphoma B cells. Blood. 1996; 88(4):1375-1382.
43. O'Neill D W, Adams S, Bhardwaj N. Manipulating dendritic cell biology for the active immunotherapy of cancer. Blood. 2004; 104(8):2235-2246.
44. Higham E M, Wittrup K D, Chen J. Activation of tolerogenic dendritic cells in the tumor draining lymph nodes by CD8+ T cells engineered to express CD40 ligand. J Immunol. 2010; 184(7):3394-3400.
45. Trinchieri G. Interleukin-12 and the regulation of innate resistance and adaptive immunity. Nat Rev Immunol. 2003; 3(2):133-146.

46. Laurin D, Marin V, Biagi E, et al. Upregulation of Adhesion Molecules on Leukemia Targets Improves the Efficacy of Cytotoxic T Cells Transduced With Chimeric Anti-CD19 Receptor. J Immunother. 2013; 36(3): 181-189.
47. Brown M P, Topham D J, Sangster M Y, et al. Thymic lymphoproliferative disease after successful correction of CD40 ligand deficiency by gene transfer in mice. Nat Med. 1998; 4(11):1253-1260.
48. Di Stasi A, Tey S K, Dotti G, et al. Inducible apoptosis as a safety switch for adoptive cell therapy. N Engl J Med. 2011; 365(18):1673-1683.

Embodiments of the Invention

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Some of the subject matter of this application may be related to U.S. patent application Ser. No. 12/593,751, which is the U.S. national phase application, pursuant to 35 U.S.C. § 371, of International Patent Application No.: PCT/US2008/004251, filed Mar. 8, 2010, which claims the benefit of U.S. Provisional Application Ser. No. 60/921,144, filed Mar. 30, 2007, the disclosures of which are hereby incorporated herein in their entireties by reference.

All patents and publications mentioned in this specification are herein incorporated by reference to the same extent as if each independent patent and publication was specifically and individually indicated to be incorporated by reference.

What is claimed is:

1. A method of increasing immune-activating cytokine production in response and/or increasing a CD8+cytotoxic T cell response to a cancer cell in a subject, comprising administering, to the subject, a T cell comprising: a) a chimeric antigen receptor (CAR) that binds to ROR1; and b) a nucleic acid encoding a recombinant CD40L, wherein the CAR comprises an intracellular signaling domain that comprises an intracellular domain of CD3ζ and an intracellular domain of a co-stimulatory receptor.

2. The method of claim 1, wherein the T cell is selected from the group consisting of cytotoxic T cells, regulatory T cells, and combinations thereof.

3. The method of claim 1, wherein the cytokine is IL-12.

4. The method of claim 1, wherein the co-stimulatory receptor is CD28, 4-1BB, or OX40.

5. The method of claim 1, wherein the nucleic acid is comprised in a vector.

6. The method of claim 5, wherein the vector is a viral vector.

7. The method of claim 6, wherein the viral vector is a retroviral vector.

8. A method of increasing dendritic cell maturation in a subject having a cancer, comprising administering, to the subject, a T cell comprising: a) a chimeric antigen receptor (CAR) that binds to ROR1; and b) a nucleic acid encoding a recombinant CD40L, wherein the CAR comprises an intracellular signaling domain that comprises an intracellular domain of CD3ζ and an intracellular domain of a co-stimulatory receptor.

9. The method of claim 8, wherein the T cell is selected from the group consisting of cytotoxic T cells, regulatory T cells, and combinations thereof.

10. The method of claim 8, wherein the co-stimulatory receptor is CD28, 4-1BB, or OX40.

11. The method of claim 8, wherein the nucleic acid is comprised in a vector.

12. The method of claim 11, wherein the vector is a viral vector.

13. The method of claim 12, wherein the viral vector is a retroviral vector.

14. A method of reducing tumor burden in a subject, and/or lengthening survival of a subject having a tumor, and/or treating a tumor in a subject, comprising administering, to the subject, an effective amount of a T cell comprising:
a) a chimeric antigen receptor (CAR) that binds to ROR1; and b) a nucleic acid encoding a recombinant CD40L, wherein the tumor expresses ROR1, and the CAR comprises an intracellular signaling domain that comprises an intracellular domain of CD3ζ and an intracellular domain of a co-stimulatory receptor.

15. The method of claim 14, wherein the T cell is selected from the group consisting of cytotoxic T cells, regulatory T cells, and combinations thereof.

16. The method of claim 14, wherein the co-stimulatory receptor is CD28, 4-1BB, or OX40.

17. The method of claim 14, wherein the nucleic acid is comprised in a vector.

18. The method of claim 17, wherein the vector is a viral vector.

19. The method of claim 18, wherein the viral vector is a retroviral vector.

* * * * *